(12) United States Patent
Goldfarb et al.

(10) Patent No.: US 9,089,258 B2
(45) Date of Patent: *Jul. 28, 2015

(54) ENDOSCOPIC METHODS AND DEVICES FOR TRANSNASAL PROCEDURES

(75) Inventors: Eric Goldfarb, Belmont, CA (US); Thomas R. Jenkins, Oakland, CA (US); Isaac J. Kim, San Jose, CA (US); Tom T. Vo, Mountain View, CA (US); Thomas J. Wisted, San Francisco, CA (US)

(73) Assignee: Acclarent, Inc., Menlo Park, CA (US)

( * ) Notice: Subject to any disclaimer, the term of this patent is extended or adjusted under 35 U.S.C. 154(b) by 1423 days.

This patent is subject to a terminal disclaimer.

(21) Appl. No.: 11/725,151

(22) Filed: Mar. 15, 2007

(65) Prior Publication Data

US 2007/0249896 A1    Oct. 25, 2007

(51) Int. Cl.
*A61M 31/00* (2006.01)
*A61B 1/005* (2006.01)
*A61B 1/00* (2006.01)
*A61B 1/01* (2006.01)
*A61B 1/233* (2006.01)
*A61B 17/24* (2006.01)
*A61B 5/00* (2006.01)
*A61B 5/06* (2006.01)
*A61M 25/09* (2006.01)

(52) U.S. Cl.
CPC .............. *A61B 1/0051* (2013.01); *A61B 1/0014* (2013.01); *A61B 1/00154* (2013.01); *A61B 1/01* (2013.01); *A61B 1/233* (2013.01); *A61B 17/24* (2013.01); *A61B 5/0084* (2013.01); *A61B 5/061* (2013.01); *A61B 2017/246* (2013.01); *A61M 2025/09083* (2013.01)

(58) Field of Classification Search
USPC .................................. 600/115, 121–125, 151
See application file for complete search history.

(56) References Cited

U.S. PATENT DOCUMENTS

| | | |
|---|---|---|
| 446,173 A | 2/1891 | Hancock |
| 504,424 A | 9/1893 | De Pezzer |
| 513,667 A | 1/1894 | Buckingham |
| 705,346 A | 7/1902 | Hamilton |
| 798,775 A | 9/1905 | Forsyth |
| 816,792 A | 4/1906 | Green et al. |
| 1,080,934 A | 12/1913 | Shackleford |
| 1,200,267 A | 10/1916 | Sunnergren |
| 1,650,959 A | 11/1927 | Pitman |

(Continued)

FOREIGN PATENT DOCUMENTS

| | | |
|---|---|---|
| CA | 2013323 | 9/1990 |
| CH | 668188 | 12/1988 |

(Continued)

OTHER PUBLICATIONS

Binner et al. 'Fibre-Optic Transillumination of the Sinuses: A Comparison of the Value of Radiography and Transillumination in Antral Disease' Clinical Otolaryngology. (1978) vol. 3 pp. 1-11.*

(Continued)

*Primary Examiner* — Matthew J Kasztejna
(74) *Attorney, Agent, or Firm* — Frost Brown Todd LLC

(57) ABSTRACT

Medical devices, systems and methods that are useable to facilitate transnasal insertion and positioning of guidewires and various other devices and instruments at desired locations within the ear, nose, throat, paranasal sinuses or cranium. Direct viewing of such placements via an endoscope.

5 Claims, 21 Drawing Sheets

(56) References Cited

U.S. PATENT DOCUMENTS

| | | |
|---|---|---|
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,525,183 A | 3/1947 | Robison |
| 2,493,326 A | 1/1950 | Trinder |
| 2,847,997 A | 8/1958 | Tibone |
| 2,899,227 A | 8/1959 | Gschwend |
| 2,906,179 A | 9/1959 | Bower |
| 2,995,832 A | 8/1961 | Alderson |
| 3,009,265 A | 11/1961 | Bezark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,447,061 A | 5/1969 | Russell et al. |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow et al. |
| 3,731,963 A | 5/1973 | Pond |
| 3,766,924 A | 10/1973 | Pidgeon |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,847,145 A | 11/1974 | Grossan |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,705,801 A | 11/1987 | Martin et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,009,655 A | 4/1991 | Daignault, Jr. et al. |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |

(56) References Cited

U.S. PATENT DOCUMENTS

| | | |
|---|---|---|
| 5,060,660 A | 10/1991 | Gambale et al. |
| 5,067,489 A | 11/1991 | Lind |
| 5,069,226 A | 12/1991 | Yamauchi et al. |
| 5,087,244 A | 2/1992 | Wolinsky et al. |
| 5,087,246 A | 2/1992 | Smith |
| 5,090,595 A | 2/1992 | Vandoninck |
| 5,090,910 A | 2/1992 | Narlo |
| 5,102,402 A | 4/1992 | Dror et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Olivier |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Shockey |
| 5,169,043 A | 12/1992 | Catania |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,197,457 A | 3/1993 | Adair |
| 5,207,695 A | 5/1993 | Trout, III |
| 5,211,952 A | 5/1993 | Spicer et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,238,004 A | 8/1993 | Sahatjian et al. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deniega |
| 5,269,752 A | 12/1993 | Bennett |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,312,430 A | 5/1994 | Rosenbluth et al. |
| 5,313,967 A | 5/1994 | Lieber et al. |
| 5,314,408 A | 5/1994 | Salmon et al. |
| 5,314,417 A | 5/1994 | Stephens et al. |
| 5,315,618 A | 5/1994 | Yoshida |
| 5,318,528 A | 6/1994 | Heaven et al. |
| 5,324,306 A | 6/1994 | Makower et al. |
| 5,333,620 A | 8/1994 | Moutafis et al. |
| 5,334,167 A | 8/1994 | Cocanower |
| 5,334,187 A | 8/1994 | Fischell et al. |
| 5,335,671 A | 8/1994 | Clement |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,445,646 A | 8/1995 | Euteneuer et al. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,459,700 A | 10/1995 | Jacobs |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,507,795 A | 4/1996 | Chiang et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wong |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,582,575 A | 12/1996 | Heckele et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim, III |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |

(56) References Cited

U.S. PATENT DOCUMENTS

| | | | |
|---|---|---|---|
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,376 A | 1/1998 | Kavteladze et al. |
| 5,707,389 A | 1/1998 | Louw et al. |
| 5,708,175 A | 1/1998 | Koyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,879,324 A | 3/1999 | von Hoffmann |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | Becker |
| 6,117,105 A | 9/2000 | Bresnaham et al. |
| 6,122,541 A | 9/2000 | Cosman et al. |
| 6,123,697 A | 9/2000 | Shippert |
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedelmayer |
| 6,249,180 B1 | 6/2001 | Maalej et al. |
| 6,254,550 B1 | 7/2001 | McNamara et al. |
| 6,268,574 B1 | 7/2001 | Edens |
| 6,270,477 B1 | 8/2001 | Bagaoisan et al. |
| 6,290,689 B1 | 9/2001 | Delaney et al. |
| 6,293,957 B1 | 9/2001 | Peters et al. |

(56) References Cited

U.S. PATENT DOCUMENTS

| | | |
|---|---|---|
| 6,295,990 B1 | 10/2001 | Lewis et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,344,028 B1 | 2/2002 | Barry |
| 6,348,041 B1 | 2/2002 | Klint |
| 6,352,503 B1 | 3/2002 | Matsui et al. |
| 6,364,856 B1 | 4/2002 | Ding et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,488,653 B1 | 12/2002 | Lombardo |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,514,249 B1 | 2/2003 | Maguire et al. |
| 6,517,478 B2 | 2/2003 | Khadem |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,223 B1 | 4/2003 | Kokish |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,718 B2 | 7/2003 | Hayzelden et al. |
| 6,585,794 B2 | 7/2003 | Shimoda et al. |
| 6,589,164 B1 | 7/2003 | Flaherty |
| 6,589,237 B2 | 7/2003 | Woloszko et al. |
| 6,596,009 B1 | 7/2003 | Jelic |
| 6,607,546 B1 | 8/2003 | Murken |
| 6,610,059 B1 | 8/2003 | West, Jr. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,652,472 B2 | 11/2003 | Jafari et al. |
| 6,652,480 B1 | 11/2003 | Imran et al. |
| 6,659,106 B1 | 12/2003 | Hovda et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,738,656 B1 | 5/2004 | Ferre et al. |
| 6,755,812 B2 | 6/2004 | Peterson et al. |
| 6,776,772 B1 | 8/2004 | Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,817,976 B2 | 11/2004 | Rovegno |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,927,478 B2 | 8/2005 | Paek |
| 6,939,361 B1 | 9/2005 | Kleshinski |
| 6,955,657 B1 | 10/2005 | Webler |
| 6,966,906 B2 | 11/2005 | Brown |
| 6,979,290 B2 | 12/2005 | Mourlas et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,176 B2 | 2/2006 | Lau |
| 7,011,654 B2 | 3/2006 | Dubrul et al. |
| 7,022,105 B1 | 4/2006 | Edwards |
| 7,043,961 B2 | 5/2006 | Pandey |
| 7,044,964 B2 | 5/2006 | Jang et al. |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,207,981 B2 | 4/2007 | Quinn et al. |
| 7,233,820 B2 | 6/2007 | Gilboa |

(56) References Cited

U.S. PATENT DOCUMENTS

| | | |
|---|---|---|
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,292,885 B2 | 11/2007 | Scott et al. |
| 7,294,345 B2 | 11/2007 | Haapakumpu et al. |
| 7,294,365 B2 | 11/2007 | Hayakawa et al. |
| 7,303,533 B2 | 12/2007 | Johansen et al. |
| 7,316,168 B2 | 1/2008 | van der Knokke et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,347,868 B2 | 3/2008 | Burnett et al. |
| 7,361,168 B2 | 4/2008 | Makower et al. |
| 7,366,562 B2 | 4/2008 | Dukesherer et al. |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,559,925 B2 | 7/2009 | Goldfarb et al. |
| 7,610,104 B2 | 10/2009 | Kaplan et al. |
| 7,618,450 B2 | 11/2009 | Zarowski et al. |
| 7,625,335 B2 | 12/2009 | Deichmann et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,691,120 B2 | 4/2010 | Shluzas et al. |
| 7,717,933 B2 | 5/2010 | Becker |
| 7,740,642 B2 | 6/2010 | Becker |
| 7,753,929 B2 | 7/2010 | Becker |
| 7,785,315 B1 | 8/2010 | Muni et al. |
| 7,799,048 B2 | 9/2010 | Hudson et al. |
| 7,799,337 B2 | 9/2010 | Levin |
| 7,833,282 B2 | 11/2010 | Mandpe |
| 7,837,672 B2 | 11/2010 | Intoccia |
| 7,840,254 B2 | 11/2010 | Glossop |
| D630,321 S | 1/2011 | Hamilton, Jr. |
| 7,875,050 B2 | 1/2011 | Samson et al. |
| D632,791 S | 2/2011 | Murner |
| 7,881,769 B2 | 2/2011 | Sobe |
| 7,988,705 B2 | 8/2011 | Galdonik et al. |
| 8,014,849 B2 | 9/2011 | Peckham |
| 8,016,752 B2 | 9/2011 | Armstrong et al. |
| 8,146,400 B2 | 4/2012 | Goldfarb et al. |
| 8,147,545 B2 | 4/2012 | Avior |
| 8,172,828 B2 | 5/2012 | Chang et al. |
| 8,197,433 B2 | 6/2012 | Cohen |
| 8,197,552 B2 | 6/2012 | Mandpe |
| 8,249,700 B2 | 8/2012 | Clifford et al. |
| 8,403,954 B2 | 3/2013 | Santin et al. |
| 8,414,473 B2 | 4/2013 | Jenkins et al. |
| 8,425,457 B2 | 4/2013 | John et al. |
| 2001/0004644 A1 | 6/2001 | Levin |
| 2001/0005785 A1 | 6/2001 | Sachse |
| 2001/0016684 A1 | 8/2001 | Shahidi |
| 2001/0023332 A1 | 9/2001 | Hahnen |
| 2001/0027307 A1 | 10/2001 | Dubrul et al. |
| 2001/0029317 A1 | 10/2001 | Hayakawa |
| 2001/0034530 A1 | 10/2001 | Malackowski et al. |
| 2001/0051761 A1 | 12/2001 | Khadem |
| 2002/0002349 A1 | 1/2002 | Flaherty et al. |
| 2002/0006961 A1 | 1/2002 | Katz et al. |
| 2002/0010384 A1 | 1/2002 | Shahidi et al. |
| 2002/0010426 A1 | 1/2002 | Clayman et al. |
| 2002/0016564 A1 | 2/2002 | Courtney et al. |
| 2002/0026155 A1 | 2/2002 | Mangosong |
| 2002/0029030 A1 | 3/2002 | Lurie et al. |
| 2002/0031941 A1 | 3/2002 | Cote et al. |
| 2002/0055746 A1 | 5/2002 | Burke et al. |
| 2002/0062133 A1 | 5/2002 | Gilson et al. |
| 2002/0077593 A1 | 6/2002 | Perkins et al. |
| 2002/0077852 A1 | 6/2002 | Ford et al. |
| 2002/0082583 A1 | 6/2002 | Lerner |
| 2002/0090388 A1 | 7/2002 | Humes et al. |
| 2002/0103459 A1 | 8/2002 | Sparks et al. |
| 2002/0107475 A1 | 8/2002 | Maginot |
| 2002/0116043 A1 | 8/2002 | Garibaldi et al. |
| 2002/0165521 A1 | 11/2002 | Cioanta et al. |
| 2003/0013985 A1 | 1/2003 | Saadat |
| 2003/0014036 A1 | 1/2003 | Varner et al. |
| 2003/0017111 A1 | 1/2003 | Rabito |
| 2003/0018291 A1 | 1/2003 | Hill et al. |
| 2003/0032942 A1 | 2/2003 | Theeuwes et al. |
| 2003/0040697 A1 | 2/2003 | Pass et al. |
| 2003/0069521 A1 | 4/2003 | Reynolds et al. |
| 2003/0069549 A1 | 4/2003 | MacMahon et al. |
| 2003/0073900 A1 | 4/2003 | Senarith et al. |
| 2003/0073955 A1 | 4/2003 | Otawara |
| 2003/0073972 A1 | 4/2003 | Rosenman et al. |
| 2003/0083608 A1 | 5/2003 | Evans et al. |
| 2003/0083613 A1 | 5/2003 | Schaer |
| 2003/0100886 A1 | 5/2003 | Segal et al. |
| 2003/0109810 A1 | 6/2003 | Brennan et al. |
| 2003/0114732 A1 | 6/2003 | Webler et al. |
| 2003/0120339 A1 | 6/2003 | Banik et al. |
| 2003/0130598 A1 | 7/2003 | Manning et al. |
| 2003/0163154 A1 | 8/2003 | Miyata et al. |
| 2003/0164952 A1 | 9/2003 | Deichmann et al. |
| 2003/0171650 A1 | 9/2003 | Tartaglia et al. |
| 2003/0181827 A1 | 9/2003 | Hojeibane et al. |
| 2003/0185872 A1 | 10/2003 | Kochinke |
| 2003/0208194 A1 | 11/2003 | Hovda et al. |
| 2003/0209096 A1 | 11/2003 | Pandey et al. |
| 2003/0220551 A1 | 11/2003 | Kimball et al. |
| 2003/0225329 A1 | 12/2003 | Rossner et al. |
| 2004/0015150 A1 | 1/2004 | Zadno-Azizi |
| 2004/0018980 A1 | 1/2004 | Gurney et al. |
| 2004/0020492 A1 | 2/2004 | Dubrul et al. |
| 2004/0034311 A1 | 2/2004 | Mihalcik |
| 2004/0043052 A1 | 3/2004 | Hunter et al. |
| 2004/0058992 A1 | 3/2004 | Marinello et al. |
| 2004/0064083 A1 | 4/2004 | Becker |
| 2004/0064105 A1 | 4/2004 | Capes et al. |
| 2004/0064150 A1 | 4/2004 | Becker |
| 2004/0098017 A1 | 5/2004 | Saab et al. |
| 2004/0116958 A1 | 6/2004 | Gopferich et al. |
| 2004/0122471 A1 | 6/2004 | Toby et al. |
| 2004/0127820 A1 | 7/2004 | Clayman et al. |
| 2004/0158229 A1 | 8/2004 | Quinn |
| 2004/0167440 A1 | 8/2004 | Sharrow |
| 2004/0167442 A1 | 8/2004 | Shireman et al. |
| 2004/0167443 A1 | 8/2004 | Shireman et al. |
| 2004/0181175 A1 | 9/2004 | Clayman et al. |
| 2004/0193073 A1 | 9/2004 | DeMello et al. |
| 2004/0220516 A1 | 11/2004 | Solomon et al. |
| 2004/0230095 A1 | 11/2004 | Stefanchik et al. |
| 2004/0230131 A1 | 11/2004 | Kassab et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0249267 A1 | 12/2004 | Gilboa |
| 2004/0254625 A1 | 12/2004 | Stephens et al. |
| 2004/0267347 A1 | 12/2004 | Cervantes |
| 2005/0027249 A1 | 2/2005 | Reifart et al. |
| 2005/0043706 A1 | 2/2005 | Eaton et al. |
| 2005/0049486 A1 | 3/2005 | Urquhart et al. |
| 2005/0055077 A1 | 3/2005 | Marco et al. |
| 2005/0059930 A1 | 3/2005 | Garrison et al. |

(56) References Cited

U.S. PATENT DOCUMENTS

| | | |
|---|---|---|
| 2005/0059931 A1 | 3/2005 | Garrison et al. |
| 2005/0089670 A1 | 4/2005 | Large et al. |
| 2005/0107720 A1 | 5/2005 | Burmeister et al. |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0124856 A1 | 6/2005 | Fujikura et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0228260 A1 | 10/2005 | Burwell et al. |
| 2005/0228412 A1 | 10/2005 | Surti |
| 2005/0234507 A1 | 10/2005 | Geske et al. |
| 2005/0240147 A1 | 10/2005 | Makower et al. |
| 2005/0244472 A1 | 11/2005 | Hughes et al. |
| 2005/0245906 A1 | 11/2005 | Makower et al. |
| 2005/0261607 A1 | 11/2005 | Johansen et al. |
| 2005/0283221 A1 | 12/2005 | Mann et al. |
| 2005/0288549 A1 | 12/2005 | Mathis |
| 2005/0288759 A1 | 12/2005 | Jones et al. |
| 2006/0004286 A1 | 1/2006 | Chang et al. |
| 2006/0004323 A1 | 1/2006 | Chang et al. |
| 2006/0047261 A1 | 3/2006 | Joshi |
| 2006/0063973 A1 | 3/2006 | Makower et al. |
| 2006/0067982 A1 | 3/2006 | Haapakumpu et al. |
| 2006/0074318 A1 | 4/2006 | Ahmed et al. |
| 2006/0085027 A1 | 4/2006 | Santin et al. |
| 2006/0095066 A1 | 5/2006 | Chang et al. |
| 2006/0106361 A1 | 5/2006 | Muni et al. |
| 2006/0107957 A1 | 5/2006 | Djupesland |
| 2006/0116749 A1 | 6/2006 | Willink et al. |
| 2006/0149310 A1 | 7/2006 | Becker |
| 2006/0173382 A1 | 8/2006 | Schreiner |
| 2006/0189844 A1 | 8/2006 | Tien |
| 2006/0190022 A1 | 8/2006 | Beyar et al. |
| 2006/0210605 A1 | 9/2006 | Chang et al. |
| 2006/0211752 A1 | 9/2006 | Kohn et al. |
| 2006/0271024 A1 | 11/2006 | Gertner et al. |
| 2006/0284428 A1 | 12/2006 | Beadle et al. |
| 2007/0005094 A1 | 1/2007 | Eaton et al. |
| 2007/0020196 A1 | 1/2007 | Pipkin et al. |
| 2007/0049929 A1 | 3/2007 | Catanese, III et al. |
| 2007/0073269 A1 | 3/2007 | Becker |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0250105 A1 | 10/2007 | Ressemann et al. |
| 2007/0269385 A1 | 11/2007 | Yun et al. |
| 2007/0293727 A1 | 12/2007 | Goldfarb et al. |
| 2007/0293946 A1 | 12/2007 | Gonzales et al. |
| 2008/0015540 A1 | 1/2008 | Muni et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0082045 A1 | 4/2008 | Goldfarb et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0103361 A1 | 5/2008 | Makower et al. |
| 2008/0103521 A1 | 5/2008 | Makower et al. |
| 2008/0119693 A1 | 5/2008 | Makower et al. |
| 2008/0125046 A1 | 5/2008 | Deng et al. |
| 2008/0125626 A1 | 5/2008 | Chang et al. |
| 2008/0154250 A1 | 6/2008 | Makower et al. |
| 2008/0154345 A1 | 6/2008 | Taylor |
| 2008/0172033 A1 | 7/2008 | Keith et al. |
| 2008/0187098 A1 | 8/2008 | Gertner et al. |
| 2008/0188803 A1 | 8/2008 | Jang |
| 2008/0188870 A1 | 8/2008 | Andre et al. |
| 2008/0195041 A1 | 8/2008 | Goldfarb et al. |
| 2008/0208242 A1 | 8/2008 | Becker |
| 2008/0208243 A1 | 8/2008 | Becker |
| 2008/0215082 A1 | 9/2008 | Becker |
| 2008/0215083 A1 | 9/2008 | Becker |
| 2008/0228085 A1 | 9/2008 | Jenkins et al. |
| 2008/0234720 A1 | 9/2008 | Chang et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0017090 A1 | 1/2009 | Arensdorf et al. |
| 2009/0028923 A1 | 1/2009 | Muni et al. |
| 2009/0030274 A1 | 1/2009 | Goldfarb et al. |
| 2009/0047326 A1 | 2/2009 | Eaton et al. |
| 2009/0088728 A1 | 4/2009 | Dollar et al. |
| 2009/0093823 A1 | 4/2009 | Chang et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0192492 A1 | 7/2009 | Eaton et al. |
| 2009/0227945 A1 | 9/2009 | Eaton et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0042046 A1 | 2/2010 | Chang et al. |
| 2010/0087811 A1 | 4/2010 | Herrin et al. |
| 2010/0114066 A1 | 5/2010 | Makower et al. |
| 2010/0121308 A1 | 5/2010 | Muni et al. |
| 2010/0174138 A1 | 7/2010 | Chang et al. |
| 2010/0174308 A1 | 7/2010 | Chang et al. |
| 2010/0198191 A1 | 8/2010 | Clifford et al. |
| 2010/0198247 A1 | 8/2010 | Chang et al. |
| 2010/0198302 A1 | 8/2010 | Shalev |
| 2010/0210901 A1 | 8/2010 | Makower et al. |
| 2010/0268245 A1 | 10/2010 | Chang et al. |
| 2010/0274188 A1 | 10/2010 | Chang et al. |
| 2010/0290244 A1 | 11/2010 | Nath |
| 2010/0298862 A1 | 11/2010 | Chang et al. |
| 2011/0004057 A1 | 1/2011 | Goldfarb et al. |
| 2011/0015482 A1 | 1/2011 | Carrillo, Jr. |
| 2011/0060214 A1 | 3/2011 | Makower |
| 2011/0112512 A1 | 5/2011 | Muni et al. |
| 2011/0166190 A1 | 7/2011 | Anderson et al. |
| 2012/0071710 A1 | 3/2012 | Gazdzinski |
| 2012/0071824 A1 | 3/2012 | Chang et al. |
| 2012/0136207 A1 | 5/2012 | Goldfarb et al. |
| 2012/0184983 A1 | 7/2012 | Chang et al. |
| 2012/0245419 A1 | 9/2012 | Makower et al. |
| 2012/0265094 A1 | 10/2012 | Goldfarb et al. |
| 2013/0231529 A1 | 9/2013 | Chang et al. |
| 2013/0245608 A1 | 9/2013 | Muni et al. |
| 2013/0261388 A1 | 10/2013 | Jenkins et al. |

FOREIGN PATENT DOCUMENTS

| | | |
|---|---|---|
| CN | 2151720 | 1/1994 |
| CN | 2151720 U | 1/1994 |
| CN | 2352818 | 12/1999 |
| DE | 03202878 | 8/1983 |
| DE | 101 05 592 A1 | 1/1988 |
| DE | 04032096 | 4/1992 |
| DE | 04406077 | 9/1994 |
| DE | 08810044 | 11/1998 |
| DE | 29923582 | 12/2000 |
| DE | 10104663 | 8/2002 |
| DE | 10105592 | 8/2002 |
| EP | 0 129 634 A1 | 1/1985 |
| EP | 0129634 | 1/1985 |
| EP | 0200430 | 11/1986 |
| EP | 0257605 | 3/1988 |
| EP | 0355996 | 2/1990 |
| EP | 0418391 | 3/1991 |
| EP | 0427852 | 5/1991 |

(56) References Cited

FOREIGN PATENT DOCUMENTS

| | | |
|---|---|---|
| EP | 0 418 391 B1 | 7/1991 |
| EP | 0515201 | 11/1992 |
| EP | 0 585 757 A1 | 3/1994 |
| EP | 0 624 349 A1 | 5/1994 |
| EP | 0623582 | 11/1994 |
| EP | 0624349 | 11/1994 |
| EP | 0744400 | 11/1996 |
| EP | 0585757 | 6/1997 |
| EP | 0893426 | 1/1999 |
| EP | 0920882 | 6/1999 |
| EP | 0974936 | 1/2000 |
| EP | 01042998 | 10/2000 |
| EP | 1086664 | 3/2001 |
| EP | 01166710 | 1/2002 |
| EP | 01413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | 5367935 | 6/1978 |
| JP | 10-24098 | 1/1989 |
| JP | 3-503011 | 7/1991 |
| JP | 3-504935 | 10/1991 |
| JP | 4-221313 | 8/1992 |
| JP | 4-224766 | 8/1992 |
| JP | 5-503650 | 6/1993 |
| JP | 5-211985 | 8/1993 |
| JP | 6-277296 | 10/1994 |
| JP | 07-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | 90/11053 | 10/1990 |
| WO | WO 90/11053 | 10/1990 |
| WO | 90/14865 | 12/1990 |
| WO | WO 90/14865 | 12/1990 |
| WO | 91/17787 | 11/1991 |
| WO | WO 91/17787 | 11/1991 |
| WO | WO 92/15286 | 2/1992 |
| WO | 92/15286 | 9/1992 |
| WO | 92/22350 | 12/1992 |
| WO | 94/12095 | 6/1994 |
| WO | WO 94/21320 | 9/1994 |
| WO | WO 95/02430 | 1/1995 |
| WO | 96/29071 | 9/1996 |
| WO | WO 96/29071 | 9/1996 |
| WO | WO 97/21461 | 6/1997 |
| WO | WO 98/55174 | 12/1998 |
| WO | WO 99/00064 | 1/1999 |
| WO | 99/24106 | 5/1999 |
| WO | 99/30655 | 6/1999 |
| WO | WO 00/53252 | 6/1999 |
| WO | WO 99/26692 | 6/1999 |
| WO | WO 99/30655 | 6/1999 |
| WO | 99/32041 | 7/1999 |
| WO | WO 99/59649 | 11/1999 |
| WO | 00/09192 | 2/2000 |
| WO | WO 00/09190 | 2/2000 |
| WO | WO 00/23009 | 4/2000 |
| WO | 00/53252 | 9/2000 |
| WO | WO 00/51672 | 9/2000 |
| WO | WO 01/05462 | 1/2001 |
| WO | 01/45572 | 6/2001 |
| WO | WO 01/45572 | 6/2001 |
| WO | 01/54558 | 8/2001 |
| WO | 01/56481 | 8/2001 |
| WO | WO 01/70325 | 9/2001 |
| WO | 01/74266 | 10/2001 |
| WO | 01/97895 | 12/2001 |
| WO | 02/062269 | 8/2002 |
| WO | WO 02/062269 | 8/2002 |
| WO | WO 02/089899 | 11/2002 |
| WO | WO 03/049603 | 6/2003 |
| WO | WO 03/063703 | 8/2003 |
| WO | 03/105657 | 12/2003 |
| WO | WO 03/105657 | 12/2003 |
| WO | 2004/006788 | 1/2004 |
| WO | WO 2004/006788 | 1/2004 |
| WO | 2004/018980 | 3/2004 |
| WO | 2004/026391 | 4/2004 |
| WO | 2004/082525 A2 | 9/2004 |
| WO | 2004/082525 A3 | 9/2004 |
| WO | 2005/018730 | 3/2005 |
| WO | 2005/077450 | 8/2005 |
| WO | 2005/089670 | 9/2005 |
| WO | WO 2005/117755 | 12/2005 |
| WO | 2006/034008 | 3/2006 |
| WO | 2006/078884 | 7/2006 |
| WO | 2006/107957 | 10/2006 |
| WO | 2006/116597 | 11/2006 |
| WO | 2006/118737 | 11/2006 |
| WO | 2006/135853 | 12/2006 |
| WO | WO 2007/035204 | 3/2007 |
| WO | 2007/111636 | 10/2007 |
| WO | 2007/124260 | 11/2007 |
| WO | 2008/036149 | 3/2008 |
| WO | 2008/045242 | 4/2008 |
| WO | 2008/051918 | 5/2008 |
| WO | 2008/134382 | 11/2008 |

OTHER PUBLICATIONS

Friedman, M. M.D., et al 'Frontal Sinus Surgery: Endoscopic Technique' Operative Techniques in Otolarynology-Head and Neck Surgery. (Jun. 2001) vol. 12, No. 2 pp. 60-65.*

Friedman, et al 'Intraoperative and Postoperative Assessment of Frontal Sinus Patency by Transillumination' Laryngoscope. (Apr. 2000) vol. 110 pp. 683-684.*

Barrett, S., Be Wary of Neurocranial Restructuring (NCR), Chirobase (available at http://www.chirobase,org/06DD/ncr.html), Jul. 2003.

Benninger, et al.; Adult Chronic Rhinosinustis: definitions, diagnosis, epidemiology, and pathophysiology; Arch Otolaryol Head and Neck Surg; vol. 129, p. S1-S22; Sep. 2003.

Croix, et al.; "Genes Expressed in Human Tumor Endothelium", May 15, 2000; Science vol. 289 pp. 1197-1202.

Davis, Greg E., et al., A Complication from Newrocranical Restructuring; Arch Otolaryngol Head Neck Surg; vol. 129, p. 472-474; Apr. 2003.

Friedman, et al., Intraoperative and Postoperative Assessment of Frontal Sinus Patency by Transillumination. Laryngoscope 110: Apr. 2000, pp. 683-684.

Gottman, et al.; Balloon Dilation of Recurrent Ostial Occlusion of the frontal sinus; Abstract No. B-04353, European Congress of Radiology, Mar. 2001.

Gottman, et al.; Balloon Dilatation of Recurrent Ostial Occlusion of the frontal sinus; ECR, Mar. 2, 2001.

Gottman, et al.; Successful Treatment of Recurrent Post-operative Frontal sinus Stenoses by Balloon Dilatation; CIRSE, Oct. 5, 2002.

Gottman, et al.; Balloon Dilatation in the nasal cavity and paranasal sinuses; CIRSE, Sep. 25, 2004.

Hospital Corpsman Sickcall Screener's Handbook Naval Hospital Great Lakes. http://www.brooksidepress.org/Products/OperationaMedicine/DATA.. 2001, pp. 1-6.

Medtronic, xomed.com-MicroFrance Catalog Browser. http://www.xomcat.com/xomfrance/index.php?zone=dom&cat-18&s... Dec. 31, 2003, pp. 1-2.

(56) References Cited

OTHER PUBLICATIONS

Single-Pole and Multi-Pole Lightguides for UV Spot Light Curing Systems. http://www.dymax.com/products/curing_equipment/lightguids /light..2004, pp. 1-2.
Strohm et al.; Die Behandlung von Stenosen der oberen Luftwege mittels rontgenologisch gesteuerter Ballondilation Sep. 25, 1999.
Sinusitis, Maxillary, Acute Surgical Treatment. http://www.emedicine.com/ent/topic340.htm.. Aug. 29, 2006, pp. 1-11.
Robison, J. Mathews, M.D., Pressure Treatment of Purulent Maxillary Sinusitis, Texas State Journal of Medicine, May 1951, pp. 281-288.
Robison, J. Mathews, M.D., Pressure Treatment of Maxillary Sinusitis, J.A.M.A., May 31, 1952, pp. 436-440.
Argon Medical. Maxxim Medical. Ad for Sniper EliteTM Hydrophilic Ni—Ti Alloy Guidewire (2001).
Aust, R., et al 'The Functional Size of the Human Maxillary Ostium in Vivo' Acta. Otolaryn. (1978) vol. 78 pp. 432-435.
Baim, D.S., MD Grossman's Cardiac Catheterization, Angiography, and Intervention (2000) Lippincott Williams & Wilkins pp. 76, 84 & 214.
Barrett, S. 'Be Wary of Neurocranial Restructuring (NCR)' Chirobase (available at: http://www.chirobase.org/06DD/ncr.html) (Jul. 2003.).
Bartal, N. 'An Improved Stent for Use in the Surgical Management of Congenital Posterior Choanal Atresia' J. Laryngol. Otol. (1988) vol. 102 pp. 146-147.
Becker, A.E. 'Restenosis After Angioplasty' The Lancet (1988) vol. 331, No. 8584 p. 532.
Bellis, M. History of the Catheter-Balloon Catheter—Thomas Fogarty. http://inventors.about.com/library/inventors/blcatheter.htm?p=1.
Benninger et al. Adult Chronic Rhinosinusitis: Definitions, Diagnosis, Epidemiology, and Pathophysiology' Arch Otolarygol Head and Neck Surg. (Sep. 2003) vol. 129 pp. S1-S32.
Bent et al. 'The Frontal Cell as a Cause of Frontal Sinus Obstruction' American Journal of Rhinology. (1994) vol. 8, No. 4 pp. 185.
Brown, C.L. et al 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Bumm, P., H. Kaiser et al 'Cortizontherapie, Corticoide in Klinik and Praxis' Thieme, Stuggart (1992) pp. 390-401 [Summary of textbook].
Casiano et al. 'Endoscopic Lothrop Procedure: The University of Miami Experience' American Journal of Rhinology (1998) vol. 12, No. 5 pp. 335-339.
Casserly, I.P. et al Chapter 7. 'Guides and Wires in Percutaneous Coronary Intervention' Strategic Approaches in Coronary Intervention (2006) Lippincott Williams & Wilkins pp. 91-99.
Chien, Y.W. et al. Nasal Systemic Drug Delivery, Drugs and the Pharmaceutical Sciences (1989) Marcel Dekker, Inc. Chapter 3, pp. 39-88.
Cohen et al 'Endoscopic Sinus Surgery: Where we are and where we're going' Current Opinion in Otolaryngology & Head and Neck Surgery (2005) vol. 13 pp. 32-38.
Colla, A. et al 'Trihaloacetylated Enol Ethers-General Synthetic Procedure and Heterocyclic Ring Closure Reactions with Hydroxylamine' Synthesis. (Jun. 1991) pp. 483-486.
Costa, M.N. et al 'Endoscopic Study of the Intranasal Ostium in External Dacryocystorhinostomy Postoperative. Influence of Saline Solution and 5-Flurorouracil' Clinics. (2007) vol. 62, Issue 1 pp. 41-46. http://www.scielo.br/scielo.php?pid=S1807-59322007000100007&script=sci arttext.
Cussler, E.L. *Diffusion: Mass Transfer in Fluid Systems* Cambridge University Press (1996) [Summary of textbook].
Davis, G.E. et al., 'A Complication From Neurocranial Restructuring' Arch Otolaryngology Head Neck Surg. (Apr. 2003) vol. 129 pp. 472-474.
Deutschmann, R. et al. 'A Contribution to the Topical Treatment of [Maxillary] Sinusitis Preliminary Communication' Stomat DDR 26, (1976) pp. 585-592.

Domb, A. et al *Handbook of Biodegradable Polymers* Harwood Academic Publishers (1997) [Summary of textbook].
Draf, W. 'Endonasal Micro-Endoscopic Frontal Sinus Surgery: the Fulda Concept' Op Tech Otolaryngol Head Neck Surg. (1991) vol. 2 pp. 234-240.
Edmond et al 'ENT Surgical Stimulator' Nov. 1998 Final Report Cooperative Agreement No. DAMD17-95-2-5023.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54-55.
Feldman, R.L. et al 'New Steerable, Ultra-Low-Profile, Fixed Wire Angioplasty Catheter: Initial Experience With the Cordis Orion™ Steerable PTCA Balloon Catheter' Cathet. Cardiovasc. Diagn. (1990) vol. 19, No. 2 pp. 142-145.
Fletcher I.E. 'New Operation and Instruments for Draining the Frontal Sinus' Ann. Otol Rhinol Laryngol. (1905) vol. 14 pp. 515-519.
Ford, C.N. 'A Multipurpose Laryngeal Injector Device' Otolaryngol. Head Neck Surg. (1990) vol. 103, No. 1 pp. 135-137.
Friedman et al 'Middle Turbinate Medialization and Preservation in Endoscopic Surgery' Otolaryngol. Head Neck Surg. (2000) vol. 123, No. 1, Part 1. pp. 76-80.
Fung, M.K.T. 'How I Do It—Head and Neck and Plasic Surgery. A Targeted Problem and its Solution. Template for Frontal Osteoplastic Flap' Laryngoscope. (1986) vol. 96 pp. 578-579.
Gatot, A. et al., 'Early Treatment of Orbital Floor Fractures with Catheter Balloon in Children' Int. J. Pediatric Otorhinolaryngol (1991) vol. 21 pp. 97-101.
Gerus, I.I. et al 'β-Ethoxyvinyl Polyfluroroalkyl Ketones—Versatile Synthones in Fluoroorganic Chemistry' Journal of Fluorine Chemistry. (1994) vol. 69 pp. 195-198. Elsevier Science S.A.
Good, R.H. 'An Intranasal Method for Opening the Frontal Sinus Establishing the Largest Possible Drainage' Laryngoscope. (1908) vol. 18 pp. 266-274.
Gopferich 'Polymer Degradation and Erosion: Mechanisms and Applications' Eur. J. Pharm. Biophar. (1996) vol. 42 pp. 1-11.
Gorlov, D.V. et al 'Acylation of 2-Methoxypropene with Anhydrides and Halides of Perflurocarboxylic Acids in the Presence of Tertiary Amines' Russian Chemical Bulletin. (Sep. 1999) vol. 48 No. 9 pp. 1791-1792. Kluwer Academic/Plenum Publishers.
Gottman, et al. 'Balloon Dilatation in the Nasal Cavity and Paranasal Sinuses' CIRSE. (Sep. 25, 2004) pp. 1-27.
Gottman, et al. 'Balloon Dilatation of Recurrent Ostial Occlusion of the Front Sinus' Abstract No. B-04353. European Congress of Radiology. (Mar. 2, 2001).
Gottman, et al. 'Successful Treatment of Recurrent Post-Operative Frontal Sinus Stenoses by Balloon Dilatation' CIRSE. (Oct. 5, 2002).
Gupta, D. et al 'Dacryocystitis Secondary to an Iatrogenic Foreign Body in the Lacrimal Apparatus' Ear, Nose & Throat Journal (2009) http://findarticles.com/p/articles/mi_m0BUM/is_7_88/ai_n32428620/.
Hashim, et al 'Balloon Compression of the Intermaxillary Sinus for Intractable Post Traumatic Bleeding from the Maxillary Artery' Scandinavian Journal of Plastic and Reconstructive Surgery and Hand Surgery (1999) vol. 33 pp. 321-324.
Hojo, M. et al 'Electrophilic Substitutions of Olefinic Hydrogens II. Acylation of Vinyl Ethers and N Vinyl Amides' Chemistry Letters (1976) pp. 499-502.
Hopf, J.U.G. et al 'Miniature Endoscopes in Otorhinolaryngologic Applications' Min Invas Ther & Allied Technol. (1998) vol. 7, No. 3 pp. 209-218.
Hosemann, W. et al *A Dissection Course on Endoscopic Endonasal Sinus Surgery* (2005) Endo-Press, Tuttlingen pp. 4-37.
Hosemann, W. et al 'Endonasal Frontal Sinusotomy in Surgical Management of Chronic Sinusitis: A Critical Evaluation' American Journal of Rhinology (1997) vol. 11, No. 1 pp. 1-9.
Hosemann, M.E. et al 'Experimentelle Untersuchungen zur Wundheilung in den Nasennebenholhlen. II. Spontaner Wundschluss and medikamentose Effekte im standardisierten Wundmodell.' HNO 39 (1991) pp. 48-54.
Hosemann W.G. et al *Minimally Invasive Endonasal Sinus Surgery* Thieme, Stuttgart, New York (2000) [Summary of textbook].

(56) References Cited

OTHER PUBLICATIONS

Hosemann, M.E. et al 'Normal Wound Healing of the Paranasal Sinuses—Clinical and Experimental Investigations' Eur Arch Otorhinolarygol. (1991) vol. 248 pp. 390-394.

Hosemann, W. et al 'Weiterbehandlung nach Nasennebenhohleneingriffen, Part 2: Theapeutische Maβnahmen' HNO akutell 7 (1999) pp. 291-302.

Hospital Corpsman Sickcall Screener's Handbook. Naval Hospital Great Lakes (Apr., 1999) http://www.brooksidepress.org/Products/Operationa.Medicine/DATA. 2001 pp. 1-6.

Hybels, R.L. 'Transillumination During Osteoplastic Frontal Sinusotomy' The Laryngoscope (Sep. 1981) vol. 91 pp. 1560.

Ijaduola, T.G.A. 'Use of a Foley Catheter for Short-Term Drainage in Frontal Sinus Surgery' The Journal of Laryngology and Otology. (1989) vol. 103 pp. 375-378.

Iro, H. et al 'A New Device for Frontal Sinus Endoscopy: First Clinical Report' Otolaryngol. Head Neck Surg. (2001) vol. 125 No. 6 pp. 613-616.

Jacobs, J.B. '100 Years of Frontal Sinus Surgery' Laryngoscope. (1997) vol. 107 pp. 1-36.

Kennedy, D.W., M.D. et al *Diseases of the Sinuses Diagnosis and Management* (Copyright 2001) by B.C. Decker Inc.

Khomutov, S.M. et al 'Dissolution of a Mixture of Steroids in Cyclodextrin Solutions: a Model Description' Pharmaceutical Chemistry Journal. (Nov. 2001) vol. 35, No. 11 pp. 627-629.

Kingdom, T.T. et al 'Image-Guided Surgery of the Sinuses: Current Technology and Applications' Otolaryngol. Clin. North Am. (Apr. 2004) vol. 37, No. 2 pp. 381-400.

Klossek, J.M. et al 'Local Safety of Intranasal Triamcinolone Acetonide: Clinical and Histological Aspects of Nasal Mucosa in the Long-Term Treatment of Perennial Allergic Rhinitis' Rhinology (2001) vol. 39, No. 1 pp. 17-22.

Kozlov et al 'Diagnosis and Treatment of Sinusitis by YAMIK Sinus Catheters' Rhinology (1996) vol. 34. pp. 123-124.

Kuhn, et al. 'The Agger Nasi Cell in Frontal Recess Obstruction: An Anatomic, Radiology and Clinical Correlation' Operative Techniques in Otolaryngology-Head and Neck Surgery (1991) vol. 2, No. 4 pp. 226-231.

Laliberte F. et al 'Clinical and Pathologic Methods to Assess the Long-Term Safety or Nasal Corticosteroids' Allergy (2000) vol. 55, No. 8 pp. 718-722.

Lang, E.V. et al 'Access Systems for Puncture at an Acute Angle' J. Vasc. Interv. Radiol. (1995) vol. 6, No. 5 pp. 711-713.

Lanza, D.C. 'Postoperative Care and Avoiding Frontal Recess Stenosis' International Advanced Sinus Symposium. General Session Abstracts. (1993) Jul. 21-24.

Large, G.C. 'Crystalline Tetracycline Hydrochloride in the Treatment of Acute and Chronic Maxillary Sinusitis' Canad. M. A. J. (1958) vol. 79 pp. 15-16.

Lund, V.J. 'Maximal Medical Therapy for Chronic Rhinosinusitis' Otolaryngol Clin N Am. (2005) vol. 38 pp. 1301-1310.

Maran, A.G.D. et al 'The Use of the Foley Catheter in the Tripod Fracture' J. Laryngol. Otol (1971) vol. 85, Issue 9 pp. 897-902.

May, M. et al 'Frontal Sinus Surgery: Endonasal Drainage Instead of an External Osteopolstic Approach' Op Tech Otolaryngo Head Neck Surgery (1995) vol. 6, No. 3 pp. 184-192.

Medtronic, xomed.com-MicroFrance Catalog Browser. http://www.xomcat.com/xomfrance/index.php?zone=both&cat=18&sub=58&prodline=1272 (Dec. 31, 2003) pp. 1-2.

Mehan, V.K. et al 'Coronary Angioplasty through 4 French Diagnostic Catheters' Cathet. Cardiovasc. Diagn. (1993) vol. 30, No. 1 pp. 22-26.

Mellor, J.M. et al 'Synthesis of Trifluromethylnaphthalenes' Tetrahedron (2000) vol. 56 pp. 10067-10074. Elseview Science Ltd.

Metson, R. et al 'Endoscopic Treatment of Sphenoid Sinusitis' Otolaryngol. Head Neck Surg. (1996) vol. 114, No. 6 pp. 736-744.

Metson, R. 'Holmium: YAG Laser Endoscopic Sinus Surgery: A Randomized Controlled Study' Laryngoscope (Jan. 1996) vol. 106, Issue 1, Supplement 77 pp. 1-18.

Miller et al. 'Management of Fractures of the Supraorbital Rim' Journal of Trauma (Jul. 1978) vol. 18, No. 7 pp. 507-512.

Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope (Aug. 1995) vol. 105 pp. 835-842.

Mols, B. 'Moveable Tool Tip for Keyhole Surgery' Delft Outlook (2005) vol. 3 pp. 13-17.

Mooney, M.R. et al 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.

Moriguchi, T. et al 'Addition-Elimination Reaction in the Trifluoroacetylation of Electron-Rich Olefins' J. Org. Chem. (1995) vol. 60, No. 11 pp. 3523-3528. American Chemical Society.

Park, K. et al *Biodegreadable Hydrogels for Medicinal Substance Delivery* (1993) Technomic Publishing Inc. Lancaster.

Piccirillo, J.F. et al 'Psychometric and Clinimetric Validity of the 20-Item Sino-Nasal Outcome Test (SNOT-20)' Otolaryngol. Head Neck Surg (2002) vol. 126, No. 1 pp. 41-47.

Piers, et al 'A Flexible Distal Tip with Two Degrees of Freedom for Enhanced Dexterity in Endoscopic Robot Surgery' Proceedings 13th Micromechanics Europe Workshop (2002) pp. 271-274.

Podoshin, L. et al 'Balloon Technique for Treatment of Frontal Sinus Fractures' The Journal of Laryngology & Otology (1967), vol. 81. pp. 1157-1161.

Pownell, P.H. et al 'Diagnostic Nasal Endoscopy' Plastic & Reconstructive Surgery (1997) vol. 99, Iss. 5 pp. 1451-1458.

Prince et al 'Analysis of the Intranasal Distribution of Ointment' J Otolaryngol. (1997) vol. 26 pp. 357-360.

Ramsdale, D.R. *Illustrated Coronary Intervention A case—oriented approach* (2001) Martin Dunitz Ltd. pp. 1-5.

Ritter, F.N. et al *Atlas of Paranasal Sinus Surgery* (1991) Igaku-Shoin Medical Pub. pp. 1-81.

Robison, J. Mathews, M.D. 'Pressure Treatment of Maxillary Sinusitis' J.A.M.A. (May 31, 1952) pp. 436-440.

Robison, J. Mathews, M.D. 'Pressure Treatment of Purulent Maxillary Sinusitis' TEXAS State Journal of Medicine. (May 1951) pp. 281-288.

Sama, A. et al 'Current Opinions on the Surgical Management of Frontal Sinus Disease' ENT News. www.pinpointmendical.com/ent-news (2009) vol. 17 No. 6 pp. 60-63.

Sanborn, T.A., et al 'Percutaneous Endocardial Transfer and Expression of Genes to the Myocardium Utilizing Fluropscopic Guidance' Catheter Cardiovasc. Interv. (2001) vol. 52, No. 2 pp. 260-266.

*Sawbones Catalog* 2001, Pacific Research Laboratories, Inc., Vashon, Washington 98070 USA.

Saxon, R.R., et al 'Technical Aspects of Accessing the Portal Vein During the TIPS Procedure' J. Vasc. Interv. Radiol. (1997) vol. 8, No. 5 pp. 733-744.

Schaefer, S.D., M.D. *Rhinology and Sinus Disease a Problem-Oriented Approach* (Copyright 1998) by Mosby, Inc.

Schneider. Pfizer Ad for Softip [date of publication unknown].

Shah, N. J. et al 'Endoscopic Pituitary Surgery—A Beginner's Guide' Indian Journal of Otolaryngology and Head and Neck Surgery (2004) vol. 56, No. 1 pp. 71-78.

Shah, N. J. 'Functional Endoscopic Sinus Surgery' (1999); found at www.bhj.org/journal/1999_4104_oct99/sp_659.htm.

Single-Pole and Multi-Pole Lightguides for UV Spot Light Curing Systems. http://www.dymax.com/products/curing_equipment/lightguids/light. (2004) pp. 1-2.

Sobol, et al 'Sinusitis, Maxillary, Acute Surgical Treatment.' eMedicine. Retrieved from the Internet: <<http://emedicine.medscape.com/article/862030-print>> (Nov. 16, 2010) pp. 1-11.

St. Croix, et al 'Genes Expressed in Human Tumor Endothelium' Science (May 15, 2000) vol. 289 pp. 1197-1202.

Stammberger H. 'Komplikationen entzundlicher Nasennebenhohlenerkrankungen eischließlich iatrogen bedingter Komplikationen.' Eur Arch Oti-Rhino-Laryngol Suppl. (Jan. 1993) pp. 61-102.

Stammberger, et al 'Special Endoscopic Anatomy of the Lateral Nasal Wall and Ethmoidal Sinuses' Functional Endoscopic Sinus Surgery. (1991) Ch. 3, pp. 49-87.

(56) References Cited

OTHER PUBLICATIONS

Strohm et al 'Die Behandlung von Stenosen der oberen Luftwege mittels rontgenologisch gesteuerter Ballondilation (Sep. 25, 1999).
Strohm, et al 'Le Traitenment Des Stenoses Voies Aeriennes Superieures Par Dilation Au Balloon' Sep. 25, 1999.
Strohm, et al 'Treatment of the Stenoses of the Upper Air Routes by Balloon Dilation' Sudwestdeutscher (Sep. 25, 1999) Abstract 45 pp. 1-3.
SurgTrainer Product Information 'Incisive Human Nasal Model for ESS Training' Surg Trainer, Ltd. Ibaraki, Japan (2004) http://www1.accsnet.ne.jp/~juliy/st/partslist.html.
Tabor, M.H. et al 'Symptomatic Bilateral Nasolacrimal Duct Cysts in a Newborn-Rhinoscopic Clinic' Ear, Nost & Throat Journal (2003) http://findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinolaringol. (1978) vol. 6 pp. 45-47.
Terumo. Medi-Tech. Boston Scientific. (1993) Ad for Glidewire.
The Operating Theatre Journal (www.otjonline.com) 'Disposable Medical Device for Wound Disclosure/The Tristel Purple Promotion—A Collaboration between Tristel plc and Karl Storz Endoscopy (UK) Ltd.' pp. 4 [retrieved on Nov. 30, 2010]. Retrieved from the Internet.
Weber, R. et al 'Endonasale Stirnhohlenchirugie mit Langzeiteinlage eines Platzhalters' Laryngol. Rhinol. Otol. (1997) vol. 76 pp. 728-734. (English Abstract).
Weber, R. et al 'Videoendscopic Analysis of Nasal Steroid Distribution' Rhinology (1999) vol. 37 pp. 69-73.
Weiner, R.I., D.O. et al 'Development and Application of Transseptal Left Heart Catheterization' Cathet. Cardiovasc. Diagn. (1988) vol. 15, No. 2 pp. 112-120.
Wiatrak, B.J. et al 'Unilateral Choanal Atresia: Initial Presentation and Endoscopic Repair' International Journal of Pediatric Otorhinolaryngology (1998) vol. 46 pp. 27-35.
Woog, et al. 'Paranasal Sinus Endoscopy and Orbital Fracture Repair' Arch Ophthalmol. (May 1998) vol. 116 pp. 688-691.
Wormald, P.J. et al 'The 'Swing-Door' Technique for Uncinectomy in Endoscopic Sinus Surgery' The Journal of Laryngology and Otology (1998) vol. 112 pp. 547-551.
Xomed-Treace. Bristol-Myers Squibb. Ad for Laser Shield II. Setting the Standards for Tomorrow [date of publication unknown].
Yamauchi, Y. et al 'Development of a Silicone Model for Endoscopic Sinus Surgery' proc International Journal of Computer Assisted Radiology and Surgery (1999) vol. 99 pp. 1039.
Yamauchi, Y. et al 'A Training System for Endoscopic Sinus Surgery with Skill Evaluation' Computer Assisted Radiology and Surgery (2001) with accompanying copy of poster presentation.
Yanagisawa et al 'Anterior and Posterior Fontanelles.' Ear, Nose & Throat Journal (2001) vol. 80. p. 10-12.
Zimarino, M., MD et al 'Initial Experience with the Europass™: A New Ultra-Low Profile Monorail Balloon Catheter' Cathet. Cardiovasc. Diagn. (1994) vol. 33, No. 1 pp. 76-79.
http://www.invotec.net/rhinology/ksplint.html. K-Splint Internal Nasal Splints; Jan. 25, 2007.
http://www.doylemedical.com/nasalsplints.htm; Doyle Nasal Splints; Jan. 25, 2007.
http://www.technologyforlife.com.au/ent/nasal.html; Nasal Surgery and Accessories; Jan. 25, 2007.
EP Communication dated Sep. 4, 2008 re: EP 05773189.
EP Communication dated Jun. 19, 2009 re: EP 05773189.
Examination Report dated Feb. 22, 2006 re: 02716734.5.
Examination Report dated Feb. 8, 2007 re: 02716734.5.
Examiners First Report dated Apr. 8, 2010 re: AU2005274794.
European Search Report and Search Opinion dated Sep. 11, 2009 from EP06815174.
International Preliminary Report on Patentability dated Aug. 25, 2006 from PCT/US05/25371.
International Preliminary Report on Patentability dated Oct. 4, 2007 from PCT/US06/002004.
International Preliminary Report dated Feb. 15, 2008 from PCT/US05/13617.
International Preliminary Report on Patentability dated Nov. 27, 2008 from PCT/US07/11449.
International Preliminary Report on Patentability dated Apr. 16, 2009 from PCT/US07/021170.
International Preliminary Report on Patentability dated May 14, 2009 from PCT/US06/36960.
International Preliminary Report on Patentability dated Oct. 22, 2009 from PCT/US08/059786.
International Preliminary Report on Patentability dated Nov. 5, 2009 from PCT/US08/061343.
International Search Report dated May 23, 2002 from PCT/EP02/01228.
International Search Report and Written Opinion dated Apr. 10, 2006 from PCT/US05/25371.
International Search Report dated May 8, 2007 from PCT/US2006/16026.
International Search Report and Written Opinion dated Aug. 17, 2007 from PCT/US05/13617.
International Search Report and Written Opinion dated Aug. 29, 2007 from PCT/US06/002004.
International Search Report dated Aug. 29, 2007 re: PCT/US06/02004.
International Search Report dated Sep. 25, 2007 from PCT/US06/37167.
International Search Report dated Oct. 19, 2007 from PCT/US07/03394.
International Search Report and Written Opinion dated May 29, 2008 from PCT/US07/021170.
International Search Report dated May 29, 2008 from PCT/US07/21922.
International Search Report and Written Opinion dated Jul. 1, 2008 from PCT/US06/22745.
International Search Report dated Jul. 3, 2008 from PCT/US2006/029695.
International Search Report dated Jul. 7, 2008 from PCT/US07/16213.
International Search Report dated Jul. 8, 2008 from PCT/US07/11474.
International Search Report and Written Opinion dated Jul. 17, 2008 from PCT/US06/36960.
International Search Report and Written Opinion dated Jul. 21, 2008 from PCT/US05/33090.
International Search Report dated Aug. 25, 2008 from PCT/US2008/000911.
International Search Report dated Sep. 10, 2008 dated PCT/US07/16212.
International Search Report and Written Opinion dated Sep. 12, 2008 from PCT/US07/16214.
International Search Report and Written Opinion dated Sep. 17, 2008 from PCT/US08/059786.
International Search Report and Written Opinion dated Sep. 17, 2008 from PCT/US08/061343.
International Search Report and Written Opinion dated Oct. 1, 2008 from PCT/US07/11449.
International Search Report dated Oct. 15, 2008 from PCT/US2008/061048.
International Search Report dated Nov. 30, 2009 re: PCT/US2009/057203.
International Search Report from PCT Application No. PCT/US2009/057203 dated Nov. 30, 2009 as issued by the European Patent Office as searching authority.
International Search Report dated Dec. 10, 2009 re: PCT/US2009/052236.
International Search Report dated Dec. 16, 2009 re: PCT/US2009/050800.
International Search Report dated Jul. 8, 2010 re: PCT/US2010/027837.
International Search Report dated Oct. 6, 2010 re: PCT/US2010/040548.
International Search Report dated Mar. 25, 2011 re: PCT/US2010/062161.

(56) References Cited

OTHER PUBLICATIONS

International Search Report dated Mar. 28, 2011 re: PCT/US2010/061850.
International Search Report dated Mar. 31, 2011 re: PCT/US2010/060898.
International Search Report dated Mar. 31, 2011 re: PCT/US2009/069143.
International Search Report dated Aug. 9, 2011 re: PCT/US2011/038751.
Partial European Search Report dated Sep. 20, 2007 re: 07252018.
Partial European Search Report dated Mar. 25, 2008 re: 07252018.
Supplemental European Search Report dated Jun. 2, 2008 re: EP05773189.
Supplemental European Search Report dated Jul. 1, 2009 re: EP06815285.
Supplemental European Search Report dated Jan. 29, 2010 from EP07836108.
Supplemental European Search Report dated Feb. 2, 2010 re: EP07836109.
Supplemental European Search Report dated Feb. 17, 2010 re: EP07836110.
Supplemental European Search Report dated Mar. 1, 2010 re: EP05778834.
Supplemental European Search Report dated Mar. 16, 2010 from EP06718986.
Supplemental European Search Report dated Jun. 22, 2010 re: EP06784759.
Supplemental European Search Report dated Sep. 23, 2010 re: EP08746715.
Supplemental Partial European Search Report dated Nov. 19, 2010 re: EP06751637.
Supplemental European Search Report dated Jan. 28, 2011 re: 07777004.
Supplemental European Search Report dated Mar. 31, 2011 re: EP05798331.
U.S. Appl. No. 10/259,300, filed Sep. 30, 2002.
U.S. Appl. No. 10/259,630, filed Sep. 30, 2002.
U.S. Appl. No. 10/470,881, filed Feb. 4, 2004.
U.S. Appl. No. 10/829,917, filed Apr. 21, 2004.
U.S. Appl. No. 10/912,578, filed Aug. 4, 2004.
U.S. Appl. No. 10/944,270, filed Sep. 17, 2004.
U.S. Appl. No. 10/037,548, filed Jan. 18, 2005.
U.S. Appl. No. 11/116,118, filed Apr. 26, 2005.
U.S. Appl. No. 11/150,847, filed Jun. 10, 2005.
U.S. Appl. No. 11/193,020, filed Jul. 29, 2005.
U.S. Appl. No. 11/234,395, filed Sep. 23, 2005.
U.S. Appl. No. 11/347,147, filed Feb. 2, 2006.
U.S. Appl. No. 11/355,512, filed Feb. 16, 2006.
U.S. Appl. No. 11/436,892, filed May 17, 2006.
U.S. Appl. No. 11/436,897, filed May 17, 2006.
U.S. Appl. No. 11/438,090, filed May 18, 2006.
U.S. Appl. No. 11/522,497, filed Sep. 15, 2006.
U.S. Appl. No. 11/527,773, filed Sep. 25, 2006.
U.S. Appl. No. 11/544,009, filed Oct. 4, 2006.
U.S. Appl. No. 11/647,530, filed Dec. 27, 2006.
U.S. Appl. No. 11/648,159, filed Dec. 29, 2006.
U.S. Appl. No. 11/655,794, filed Jan. 18, 2007.
U.S. Appl. No. 11/725,151, filed Mar. 15, 2007.
U.S. Appl. No. 11/789,704, filed Apr. 24, 2007.
U.S. Appl. No. 11/789,705, filed Apr. 24, 2007.
U.S. Appl. No. 11/803,695, filed May 14, 2007.
U.S. Appl. No. 11/925,540, filed Oct. 26, 2007.
U.S. Appl. No. 11/926,326, filed Oct. 29, 2007.
U.S. Appl. No. 11/926,565, filed Oct. 29, 2007.
U.S. Appl. No. 11/928,097, filed Oct. 30, 2007.
U.S. Appl. No. 11/011,100, filed Jan. 23, 2008.
U.S. Appl. No. 12/100,361, filed Apr. 9, 2008.
U.S. Appl. No. 12/117,582, filed May 8, 2008.
U.S. Appl. No. 12/117,672, filed May 8, 2008.
U.S. Appl. No. 12/117,961, filed May 9, 2008.
U.S. Appl. No. 12/118,931, filed May 12, 2008.
U.S. Appl. No. 12/120,902, filed May 15, 2008.
U.S. Appl. No. 12/122,884, filed May 19, 2008.
U.S. Appl. No. 12/340,226, filed Dec. 19, 2008.
U.S. Appl. No. 12/341,602, filed Dec. 22, 2008.
U.S. Appl. No. 12/502,101, filed Jul. 13, 2009.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
USPTO Office Action dated Sep. 16, 2005 in U.S. Appl. No. 10/259,300.
USPTO Office Action dated Jul. 7, 2006 in U.S. Appl. No. 10/259,300.
USPTO Office Action dated Feb. 13, 2007 in U.S. Appl. No. 10/259,300.
USPTO Office Action dated May 29, 2007 in U.S. Appl. No. 10/912,578.
USPTO Office Action dated Oct. 9, 2007 in U.S. Appl. No. 10/259,300.
USPTO Office Action dated Oct. 18, 2007 in U.S. Appl. No. 11/037,548.
USPTO Office Action dated Nov. 14, 2007 in U.S. Appl. No. 10/912,578.
USPTO Office Action dated Nov. 28, 2007 in U.S. Appl. No. 11/234,395.
USPTO Office Action dated Dec. 6, 2007 in U.S. Appl. No. 11/037,548.
USPTO Office Action dated Dec. 10, 2007 in U.S. Appl. No. 10/912,578.
USPTO Office Action dated Jan. 24, 2008 in U.S. Appl. No. 10/259,300.
USPTO Office Action dated Apr. 9, 2008 in U.S. Appl. No. 11/037,548.
USPTO Office Action dated Sep. 12, 2008 in U.S. Appl. No. 10/829,917.
USPTO Office Action dated Oct. 6, 2008 in U.S. Appl. No. 10/259,300.
USPTO Office Action dated Oct. 29, 2008 in U.S. Appl. No. 11/347,147.
USPTO Office Action dated Nov. 7, 2008 in U.S. Appl. No. 10/944,270.
USPTO Office Action dated Nov. 17, 2008 in U.S. Appl. No. 10/829,917.
USPTO Office Action dated Nov. 17, 2008 in U.S. Appl. No. 12/117,582.
USPTO Office Action dated Nov. 17, 2008 in U.S. Appl. No. 12/118,931.
USPTO Office Action dated Nov. 25, 2008 in U.S. Appl. No. 12/117,961, filed May 9, 2008.
USPTO Office Action dated Dec. 5, 2008 in U.S. Appl. No. 12/120,902, filed May 15, 2008.
USPTO Office Action dated Jan. 28, 2009 in U.S. Appl. No. 10/944,270.
USPTO Office Action dated Feb. 4, 2009 in U.S. Appl. No. 11/347,147.
USPTO Office Action dated Mar. 3, 2009 in U.S. Appl. No. 12/117,582.
USPTO Office Action dated Mar. 4, 2009 in U.S. Appl. No. 12/118,931.
USPTO Office Action dated Mar. 17, 2009 in U.S. Appl. No. 11/690,127.
USPTO Office Action dated Mar. 18, 2009 in U.S. Appl. No. 10/829,917.
USPTO Office Action dated Mar. 23, 2009 in U.S. Appl. No. 11/804,309.
USPTO Office Action dated Mar. 23, 2009 in U.S. Appl. No. 11/926,326.
USPTO Office Action dated Apr. 21, 2009 in U.S. Appl. No. 10/944,270.
USPTO Office Action dated Jul. 30, 2009 in U.S. Appl. No. 12/118,931.

(56) References Cited

OTHER PUBLICATIONS

USPTO Office Action dated Aug. 6, 2009 in U.S. Appl. No. 11/347,147.
USPTO Office Action dated Aug. 6, 2009 in U.S. Appl. No. 12/117,582.
USPTO Office Action dated Aug. 6, 2009 in U.S. Appl. No. 12/117,961.
USPTO Office Action dated Aug. 28, 2009 in U.S. Appl. No. 11/150,847.
USPTO Office Action dated Oct. 21, 2009 in U.S. Appl. No. 12/120,902.
USPTO Office Action dated Nov. 9, 2009 in U.S. Appl. No. 10/829,917.
European Search Report dated Sep. 27, 2011 re: EP10182961.
Gottman, et al., Balloon Dilation of Recurrent Ostial Occlusion of the Front Sinus'OASIS-Online Anstract Submission and Invitation System, 1996-2006, Coe Truman Technologies, Inc.
Gottman, D. 'Treatment of Stenoses of Upper Air Routes by Balloon Dilation' Proceedings of the 83rd Annual Convention of Association of West German ENT Physicians (1999).
Gottman, et al., Balloon Dilation of Recurrent Ostial Occlusion of the Front Sinus'OASIS-Online Abstract Submission and Invitation System, 1996-2006, Coe Truman Technologies, Inc.
Gottman, et al. 'Balloon Dilation of Recurrent Ostial Occlusion of the Frontal Sinus' CIRSE (Mar. 2001).
Ingals, E.F. 'New Operation and Instruments for Draining the Frontal Sinus' Ann. Otol. Rhinol. Layyngol. vol. 14 (1905) pp. 644-649.
Nasal Surgery and Accessories, Jan. 25, 2007; www.technologyforlife.com.au/ent/nasal.html.
Sinusitis, Maxillary, Acute Surgical Treatment. Http://www.emedicine.com/ent/topic340.htm. Aug. 29, 2006. pp. 1-11.
SurgTrainer Product Information 2003, Surg Trainer, Ltd. Ibaraki, Japan.
Australian Office Action, Examiners First Report dated Dec. 9, 2011 for Application No. AU 2006292818.
Chinese Office Action, First Office Action dated Nov. 5, 2012 for Application No. CN 200980137396.1.
Chinese Search Report dated Oct. 29, 2012 for Application No. CN 200980137396.1.
Chinese Search Report dated Jan. 11, 2013 for Application No. CN 200980152995.0.
Chinese Office Action, First Office Action dated Jan. 29, 2013 for Application No. CN 200980152995.1.
European Communication dated Aug. 1, 2012 for Application No. EP 06784759.0.
European Communication dated Aug. 24, 2012 for Application No. EP 05798331.4.
European Communication dated Nov. 9, 2012 for Application No. EP 07750248.2.
European Communication dated Apr. 19, 2012 for Application No. EP 08746715.5.
European Communication dated Jan. 7, 2013 for Application No. EP 08746715.5.
European Communication dated Apr. 11, 2013 for Application No. EP 05778834.1.
European Communication dated May 10, 2013 for Application No. EP 06751637.7.
European Search Report date Mar. 16, 2010 for Application No. EP 06718986.
European Search Report date Sep. 29, 2011 for Application No. EP 10182893.
European Search Report date Jul. 23, 2012 for Application No. EP 12162709.
European Search Report date Jul. 24, 2012 for Application No. EP 12162712.
European Search Report date Aug. 31, 2012 for Application No. EP 12173295.
European Search Report date Oct. 10, 2012 for Application No. EP 12175607.
European Search Report date Nov. 22, 2012 for Application No. EP 12182993.
European Search Report date Dec. 5, 2012 for Application No. EP 12182998.
European Search Report date Jan. 9, 2013 for Application No. EP 12183000.
European Search Report date Jan. 11, 2013 for Application No. EP 12183002.
European Search Report dated Aug. 13, 2013 for Application No. EP 13172140.
European Search Report dated Sep. 9, 2013 for Application No. EP 13179223.
Supplemental European Search Report dated Aug. 30, 2011 for Application No. EP 06800540.
Supplemental European Search Report dated Sep. 29, 2011 for Application No. EP 07750248.
PCT Search Report dated Nov. 30, 2009 for Application No. PCT/US2009/057203.
English Machine Translation of Japanese Patent Publication No. JP5-503650.
International Preliminary Report on Patentability dated Jun. 29, 2011 for Application No. PCT/US2009/069143.
International Search Report dated Mar. 31, 2010 for Application No. PCT/US2009/069143.
International Search Report dated May 18, 2012 for Application No. PCT/US2011/052321.
Partial International Search Report dated Feb. 7, 2012 for Application No. PCT/US2011/052321.
Japanese Office Action, Examiner's Decision of Refusal dated Oct. 18, 2011 for Application No. JP 2007-509632.
Japanese Office Action, Notification of Reasons for Refusal dated Apr. 26, 2011 for Application No. JP 2007-532485.
Japanese Office Action, Notification of Reasons for Refusal dated Jan. 24, 2012 for Application No. JP 2007-532485.
Japanese Office Action, Notification of Reasons for Refusal dated Aug. 16, 2011 for Application No. JP 2008-516013.
Japanese Office Action, Notification of Reasons for Refusal dated Nov. 8, 2011 for Application No. JP 2008-524250.
Japanese Office Action, Notification of Reasons for Refusal dated Jun. 25, 2013 for Application No. JP 2012-131840.
Japanese Office Action, Notification of Reasons for Refusal dated Sep. 18, 2013 for Application No. JP 2011-527942.
Russian Office Action dated Sep. 28, 2012 for Application No. RU 2011130530.
Russian Office Action dated Mar. 19, 2013 for Application No. RU 2011130530.
USPTO Office Action dated Dec. 29, 2008 for U.S. Appl. No. 11/193,020.
USPTO Office Action dated May 13, 2009 for U.S. Appl. No. 11/193,020.
U.S. Appl. No. 11/648,158, filed Dec. 29, 2006.
U.S. Appl. No. 11/804,308, filed May 16, 2007.
U.S. Appl. No. 11/804,309, filed May 16, 2007.
U.S. Appl. No. 13/840,430, filed Mar. 15, 2013.
European Search Report dated Oct. 16, 2012 from application No. 12175607.6.

* cited by examiner

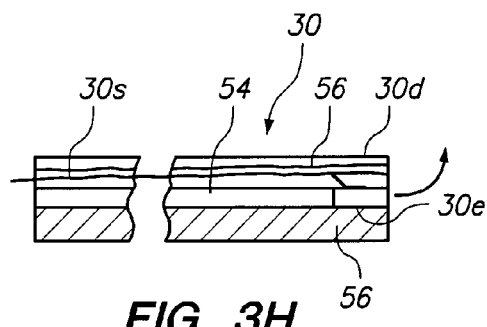
FIG. 3H
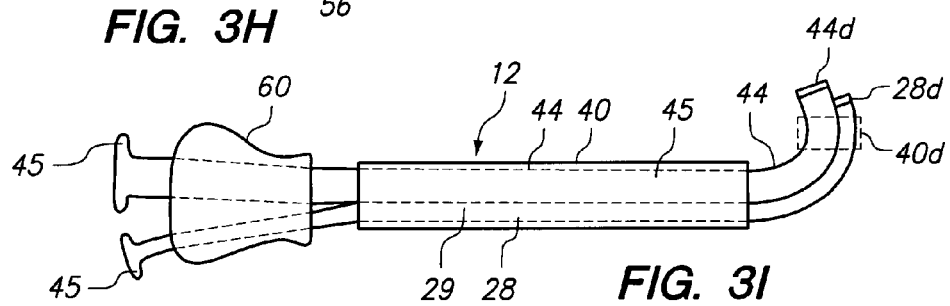
FIG. 3I
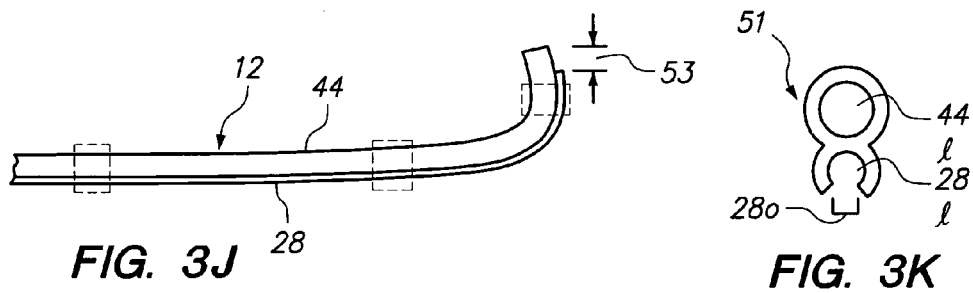
FIG. 3J
FIG. 3K
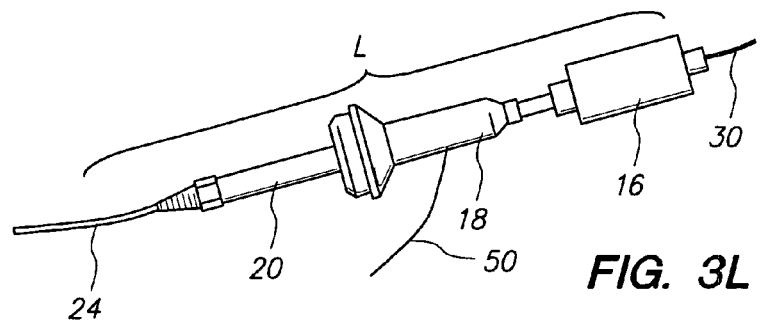
FIG. 3L

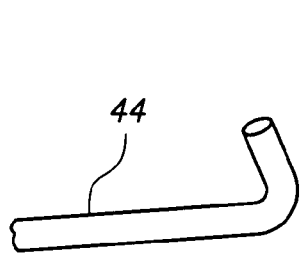
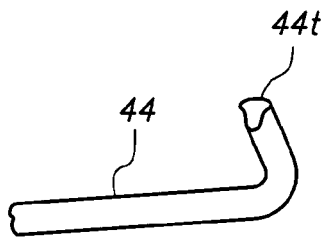
FIG. 9A    FIG. 9B
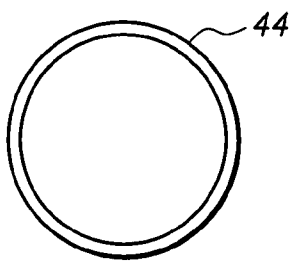
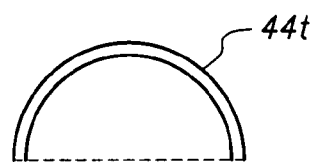
FIG. 9C    FIG. 9D
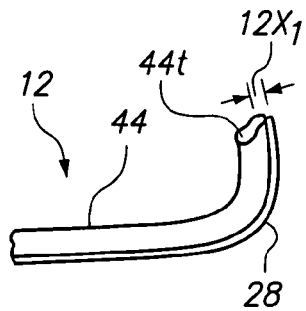
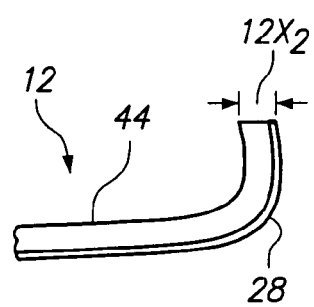
FIG. 10A    FIG. 10B
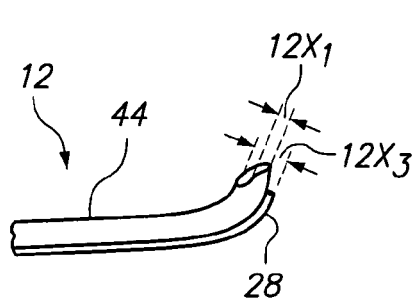
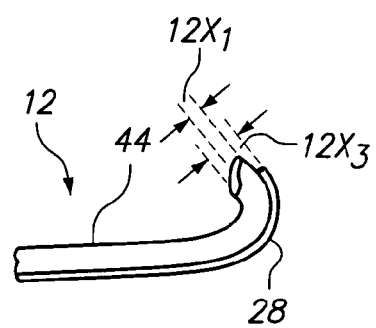
FIG. 10C    FIG. 10D

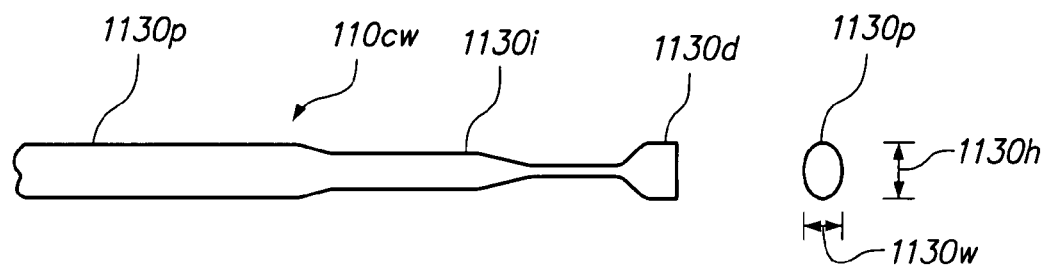
FIG. 22A  FIG. 22B
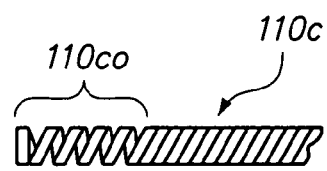
FIG. 23A
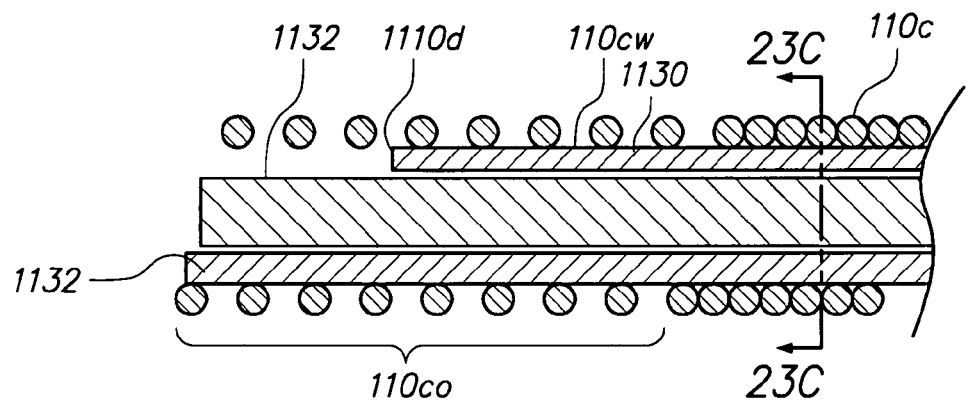
FIG. 23B

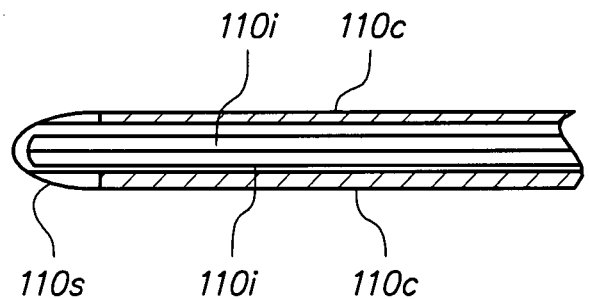
FIG. 27
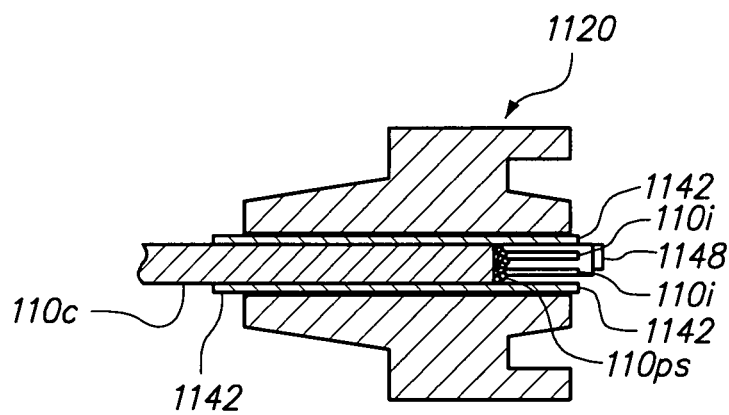
FIG. 28
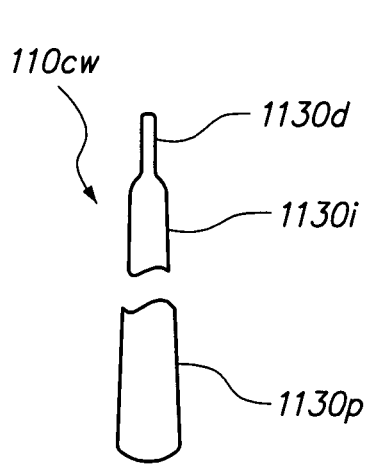   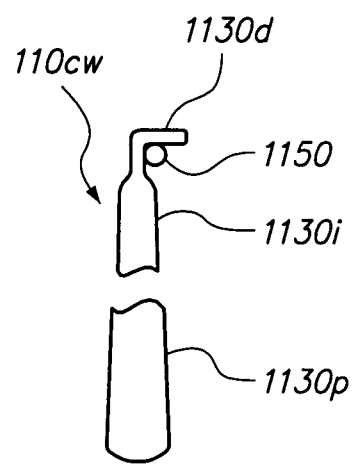
FIG. 29A   FIG. 29B

ENDOSCOPIC METHODS AND DEVICES FOR TRANSNASAL PROCEDURES

FIELD OF THE INVENTION

The present invention relates generally to medical apparatus and methods and more particularly to devices and methods that are useable to facilitate transnasal insertion and positioning of guidewires and various other apparatus at desired locations within the ear, nose, throat, paranasal sinuses or cranium.

BACKGROUND OF THE INVENTION

Functional endoscopic sinus surgery (FESS) is currently the most common type of surgery used to treat chronic sinusitis. In a typical FESS procedure, an endoscope is inserted into the nostril along with one or more surgical instruments. The surgical instruments are then used to cut tissue and/or bone, cauterize, suction, etc. In most FESS procedures, the natural ostium (e.g., opening) of at least one paranasal sinus is surgically enlarged to improve drainage from the sinus cavity. The endoscope provides a direct line-of-sight view whereby the surgeon is typically able to visualize some but not all anatomical structures within the surgical field. Under visualization through the endoscope, the surgeon may remove diseased or hypertrophic tissue or bone and may enlarge the ostia of the sinuses to restore normal drainage of the sinuses. FESS procedures can be effective in the treatment of sinusitis and for the removal of tumors, polyps and other aberrant growths from the nose.

The surgical instruments used in the prior art FESS procedures have included; applicators, chisels, curettes, elevators, forceps, gouges, hooks, knives, saws, mallets, morselizers, needle holders, osteotomes, ostium seekers, probes, punches, backbiters, rasps, retractors, rongeurs, scissors, snares, specula, suction cannulae and trocars. The majority of such instruments are of substantially rigid design.

In order to adequately view the operative field through the endoscope and/or to allow insertion and use of rigid instruments, many FESS procedures of the prior art have included the surgical removal or modification of normal anatomical structures. For example, in many prior art FESS procedures, a total uncinectomy (e.g., removal of the uncinate process) is performed at the beginning of the procedure to allow visualization of and access to the maxilary sinus ostium and/or ethmoid bulla and to permit the subsequent insertion of the rigid surgical instruments. Indeed, in most traditional FESS procedures, if the uncinate process is allowed to remain, such can interfere with endoscopic visualization of the maxillary sinus ostium and ethmoid bulla, as well as subsequent dissection of deep structures using the available rigid instrumentation.

More recently, new devices, systems and methods have been devised to enable the performance of FESS procedures and other ENT surgeries with minimal or no removal or modification of normal anatomical structures. Such new methods include, but are not limited to, uncinate-sparing procedures using Balloon Sinuplasty™ tools and uncinate-sparing ethmoidectomy procedures using catheters, non-rigid instruments and advanced imaging techniques (Acclarent, Inc., Menlo Park, Calif.). Examples of these new devices, systems and methods are described in U.S. patent application Ser. No. 10/829,917entitled Devices, Systems and Methods for Diagnosing and Treating Sinusitis and Other Disorders of the Ears, Nose and/or Throat; issued as U.S. Pat. No. 7,654, 997 on Feb. 2, 2010; U.S. patent application Ser. No. 10/944, 270 entitled Apparatus and Methods for Dilating and Modifying Ostia of Paranasal Sinuses and Other Intranasal or Paranasal Structures, published as U.S. Pub. No. 2006/0004323 on Jan. 5, 2006; U.S. patent application Ser. No. 11/116,118 entitled Methods and Devices for Performing Procedures Within the Ear, Nose, Throat and Paranasal Sinuses filed Apr. 26, 2005, issued as U.S. Pat. No. 7,720,521 on May 18, 2010 and U.S. patent application Ser. No. 11/150, 847 filed Jun. 10, 2005, issued as U.S. Pat. No. 7,803,150 on Sep. 28, 2010. Procedures using Balloon Sinuplasty™ tools such as those described in the above-noted applications, for example, are performable using various types of guidance including but not limited to C-arm fluoroscopy, transnasal endoscopy, optical image guidance and/or electromagnetic image guidance.

In FESS procedures, the surgeon typically holds or navigates the endoscope with one hand while using the other hand to handle the surgical instruments. Recognizing the desirability of integrating an endoscope with an operative device so that both could be moved with a single hand, U.S. patent application Ser. No. 11/234,395 filed Sep. 23, 2005, issued as U.S. Pat. No. 7,410,480 on Aug. 12, 2008 describes a number of transnasally insertable sinus guides that have endoscopes attached thereto or integrated therewith.

There remains a need for further development of new devices and methodology to facilitate the integration of endoscopes with sinus guides and/or other instruments to facilitate endoscopic viewing of guidewires and/or other devices/instruments as they are transnasally inserted, positioned and used to treat disorders of the ear, nose, throat, paranasal sinuses or other intracranial disorders that are transnasally accessible.

SUMMARY OF THE INVENTION

A beneficial aspect of the present invention is to allow a user to be able to see an adjustable view, with an endoscope, that is generally aligned with the same axis of movement of the user's working device. This is particularly useful when the axis of movement is at an angle with respect to the axis of entry into the patient. This aspect allows the user to see "around the corner" of anatomy that ordinarily would block his/her view and which would therefore require removal in a traditional FESS procedure to allow visualization. This aspect of the invention allows the user to also verify the location of his/her Balloon Sinuplasty™ tools without having to use fluoroscopy or image guidance systems, so that the procedure does not have to be performed in an operating room. Another beneficial aspect of the present invention is that it enables a reduction in the amount of fluoroscopy that needs to be performed by the user doing the procedure, resulting in a reduction in radiation exposure to the user and the patient.

Another beneficial aspect of the present invention is that it allows a user to hold a tool with an endoscope attached or incorporated therein, such that both can be held with one hand while allowing the user to manipulate another tool with the other hand, thereby eliminating the need for an assistant.

A method for positioning a guide device useful for delivering at least one working device therethrough to deliver a working end portion thereof to a desired location within the ear, nose, throat or cranium of a human or animal patient is provided, including the steps of: inserting an endoscope into or through an endoscope channel of the guide device that includes an elongated shaft; inserting the guide device into an internal space of the patient; and viewing through the endoscope to guide positioning and delivery of the guide device to an intended location in the patient.

A method for locating a sinus ostium is provided, including the steps of: inserting an endoscope through a nostril of a patient and advancing the endoscope toward a location of the sinus ostium; inserting a guidewire through the nostril and advancing a distal end portion of the guidewire distally of a distal end of the endoscope; and viewing, through the endoscope, the advancement of the distal end portion of the guidewire to facilitate guidance of the advancement of the guidewire along a desired path.

A method for treating a patient is provided, including the steps of: inserting an endoscope into or through an endoscope channel of a guide device that includes an elongated shaft; inserting the guide device through a nostril of the patient; advancing a distal end portion of the guide device toward a sinus ostium of the patient; advancing a distal end portion of the endoscope distally of the distal end portion of the guide device, and navigating the distal end portion of the endoscope through the sinus ostium, said navigating being assisted by visualization through the endoscope.

A method of visually inspecting a sinus cavity is provided, including the steps of: inserting an endoscope through a lumen of a working device having previously been inserted through a nostril of a patient, through a sinus ostium and into the sinus cavity; and viewing the sinus cavity through the endoscope.

A method of directing a guidewire to a target location within the ear, nose, throat or cranium of a patient is provided, including the steps of: inserting an illuminating guidewire internally of the patient; emitting light from a distal end portion of the guidewire; and tracking movements of the distal end portion of the guidewire by tracking movements of an illumination spot visible externally of the patient, wherein movements of the illumination spot correspond to movements of the distal end portion of the guidewire internally of the patient.

A guide device useable to position a working device at a desired location within the ear, nose, throat or cranium of a human or animal subject is provided, including: a transnasally insertable elongate shaft having a proximal end and a distal end; a first channel into which an endoscope may be inserted so that the endoscope may be used to view at least an area beyond the distal end of the shaft; and a second channel through which the working device may be advanced, wherein the first channel is statically located relative to the second channel.

A flexible microendoscope is provided, including: an elongated shaft; a plurality of image fibers; a lens attached at distal end of said image fibers; and a plurality of light transmitting fibers; wherein the microendoscope has a cross-sectional area permitting insertion into a nasal cavity of a patient.

An illuminating guidewire device is provided, including: a flexible distal end portion; at least one light emitting element in the distal end portion; at least one structure extending from a proximal end of the device through a proximal end portion of the device and at least part of the distal end portion to connect the at least one light emitting element with a power source; a coil; and at least one coil support within the coil, with at least a portion of each coil support fixed to the coil.

A method of making an illuminating guidewire is provided, including the steps of: providing a coil having a predetermined length and diameter; inserting mandrels through an annulus of the coil; inserting a first core support into the coil and fixing a portion of the first core support at a predetermined length from a distal end of the coil; removing a mandrel and inserting a second core support; fixing said second core support at predetermined locations along a length thereof, to the coil and fixing the firs core support at additional locations along the length thereof to the coil; and inserting illumination fibers.

A transnasally insertable guide system for positioning an endoscope at a desired location within the ear, nose, throat or cranium of a human or animal subject is provided, including: a tubular guide having an elongate shaft and a lumen, at least a portion of the elongate shaft having a predetermined shape; a sheath sized to be inserted into the lumen of the tubular guide, the sheath comprising an elongate flexible body having a distal end and a scope lumen; and an endoscope that is advanceable through the scope lumen of the sheath, wherein the endoscope is useable to view the anatomy when advanced through the scope lumen of the sheath having been inserted into the guide and the guide having been inserted into an internal space within the patient; and wherein the sheath and endoscope are thereafter removable leaving the tubular guide in place.

A guide device useable to position a working device at a desired location within the ear, nose, throat or cranium of a human or animal subject is provided, including: a transnasally insertable elongate shaft having a proximal end and a distal end; a channel through which the working device may be advanced, wherein the shaft comprises a scooped distal tip.

These and other features of the invention will become apparent to those persons skilled in the art upon reading the details of the devices, methods and systems as more fully described below.

BRIEF DESCRIPTION OF THE DRAWINGS

FIG. 3H illustrates a steering mechanism provided in an endoscope that can be operated from a proximal end portion of the endoscope.

FIG. 3I illustrates a guide device according to one embodiment of the present invention.

FIG. 3J illustrates a distal portion of a guide device having a removably attached endoscope channel.

FIG. 3K illustrates a snap fitting that may be used to releasably attach an endoscope channel to a main tube of a sinus guide.

FIG. 3L is a side view of the connector/camera/light cable assembly of the system of FIG. 1.

FIG. 9A illustrates a guide device having a distal end with a circular tip.

FIG. 9B illustrates a guide device having a distal end with a scooped-tip.

FIG. 9C illustrates an end view of the device of FIG. 9A.

FIG. 9D illustrates an end view of the device of FIG. 9B.

FIG. 10A illustrates the reduced profile of a scooped-tip device relative to the profile of the device having a circular end in FIG. 10B.

FIGS. 10C-10D show reduced profiles of scooped-tip devices including a set back endoscope channel.

FIG. 22A shows an example of a core support formed from an oval wire.

FIG. 22B illustrates a proximal end view of the core support of FIG. 22A.

FIG. 23A shows a distal portion of a coil having been stretched to break tension between adjacent coils and to form an open-pitch portion.

FIG. 23B illustrates insertion of mandrels and a first core support into a coil.

FIG. 27 illustrates insertion of illumination fibers and formation of a distal lens.

FIG. 28 illustrates finishing steps at a proximal end of the illuminating guidewire.

FIGS. 29A-29B illustrate formation of a preset bend in a core support.

DETAILED DESCRIPTION OF THE INVENTION

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "San", and "the" include plural referents unless the context clearly dictates otherwise. Thus, for example, reference to "a channel" includes a plurality of such channels and reference "the endoscope" includes reference to one or more endoscopes and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Sinus Guide with Continuous Endoscope Channel

Figure 1:
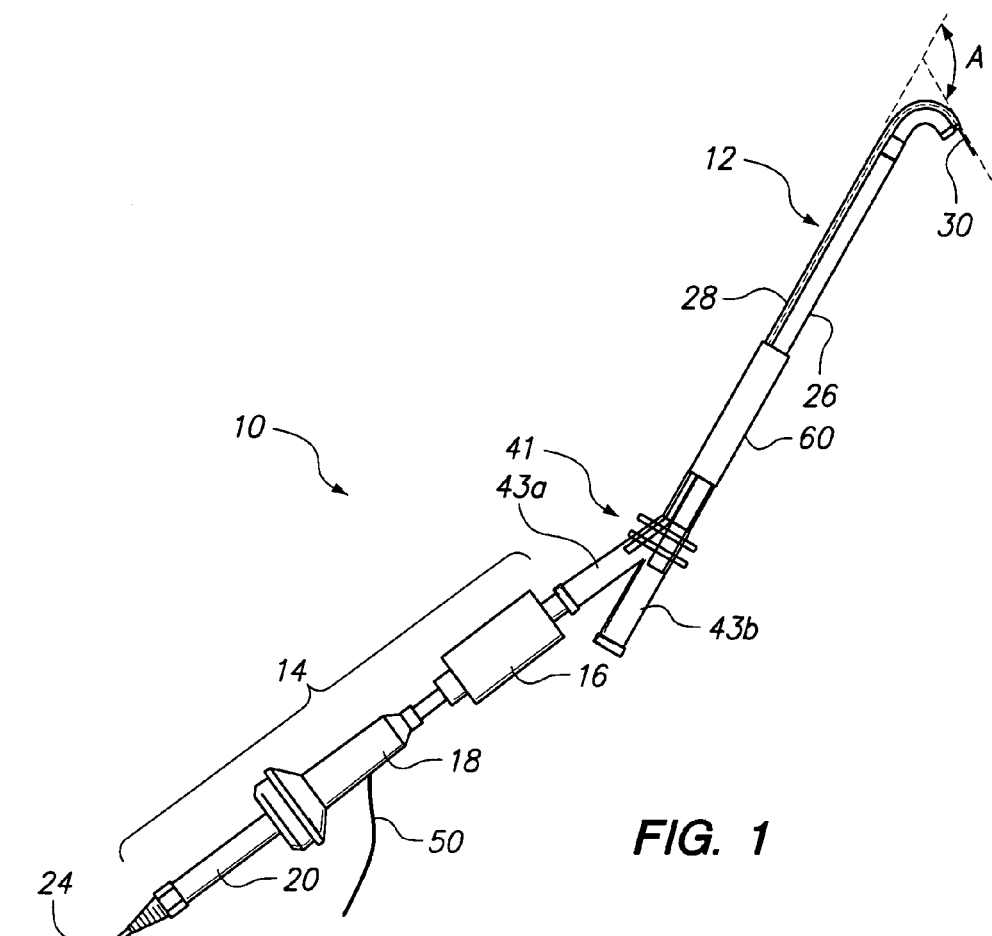
FIG. 1 is a perspective view of one embodiment of a guide system of the present invention.
Figure 3A:
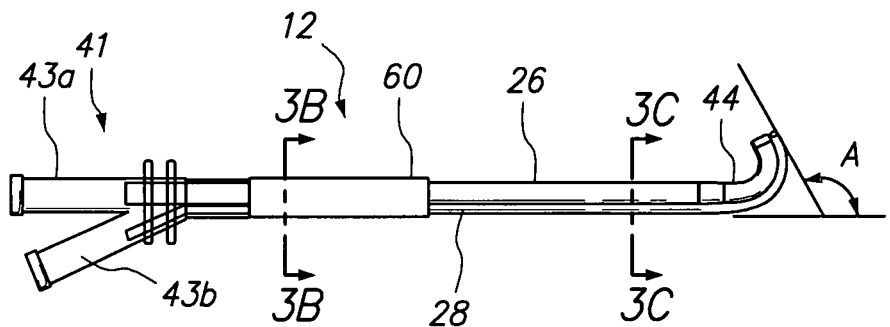
FIG. 3A is a side view of the guide catheter of the system of FIG. 1.
Figure 3B:
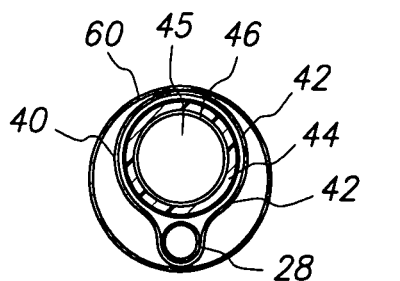
FIG. 3B is a cross sectional view through line 3B-3B of FIG. 3A.
Figure 3C:
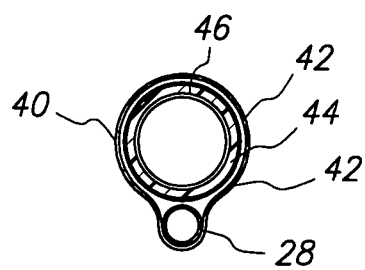
FIG. 3C is a cross sectional view through line 3C-3C of FIG. 3A.

FIG. 1 shows one embodiment of a sinus guide system 10 of the present invention. This sinus guide system 10 comprises a sinus guide 12 and a camera/transmission/endoscope assembly 14. This embodiment of the sinus guide 12 is shown in more detail in FIGS. 3A-3C. As shown, this sinus guide 12 comprises a sinus guide body 26 and an endoscope channel 28 in generally side-by-side arrangement. The sinus guide body 26 comprises a tube 44 having a lumen 45 (e.g., see FIG. 3B), such as a polymer tube made of biocompatible polymeric material. A distal end portion 44d, e.g. a length of about 2 mm may be made of stainless steel, for example, to increase durability, as illustrated in FIG. 3I. Similarly, a distal end portion 28d of channel 28 can be formed of stainless steel. Alternatively, channel 28 and/or tube 44 can be formed of stainless steel along the entire length thereof. Further alternatively, tube 44 and/or channel 28 may be formed over an entire length thereof of stainless steel or other biocompatible metal, except for a polymer distal tip. Optionally, a liner 46 (FIG. 3B) may be disposed within the lumen 45 of the tube 44. Such liner may be formed of lubricious or smooth material such as polytetrafluoroethylene (PTFE). Also, optionally, a proximal portion of the tube 44 may be surrounded by an outer tube member 42 formed of material such as stainless steel hypotube. In the embodiment shown, a distal portion of tube 44 extends out of and beyond the distal end of outer tube 42. This protruding distal portion of tube 44 may be straight or curved. Also, it may be pre-formed at the time of manufacture or malleable to a desired shape at the time of use. When intended for use in accessing the ostium of a paranasal sinus, the distal portion of tube 44 may be curved to form an angle A from about 0 degrees to about 120 degrees. For example, a series of sinus guides 12 having angles A of 0, 30, 70, 90 and 110 degrees may be provided thereby allowing the physician to select the sinus guide angle A that is most appropriate for the particular paranasal sinus ostium to be accessed. Additionally, in some embodiments, a rotation grip 60 may be positioned about a proximal portion of the sinus guide 10, as seen in FIGS. 1, 3A and 3B. This rotation grip 60 may have a smooth or textured round outer surface (e.g., it may be a cylindrical tube), or it may have a contoured shape, raised at a distal end portion thereof (as well as, optionally, raised at a proximal end thereof), e.g., see FIG. 3I, to prevent slipping of an operator's hand during pushing (or pulling) on the handle 60. In any case, handle 60 may be grasped between the fingers of the operator's hand and easily rotated, thereby facilitating rotation (e.g., rolling) of the sinus guide 12 as it is being used. Such rotation of the sinus guide 12 may be desirable for a number of reasons including but not limited to positioning of the distal end of the sinus guide 12 at a desired location and/or maneuvering the location of an endoscope 30 that is inserted through the endoscope channel 28.

The endoscope channel 28 may comprise any structure (e.g., tube, track, groove, rail, etc.) capable of guiding the advancement of a flexible endoscope. In the particular examples shown in these figures, the endoscope channel 28 comprises a tube (e.g., a polymer tube or stainless steel tube or combination of polymer and metal, as noted above) having a lumen 29 extending therethrough. In the embodiment seen in FIGS. 1-3C, the endoscope channel 28 is attached to and extends along substantially the entire length of the sinus guide body 26. In another embodiment, the endoscope channel 28 can be inside the sinus guide body 26. In other embodiments, such as described with regard to FIGS. 4A-4C in U.S. patent application Ser. No. 11/647,530, published as U.S. Pub. No. 2007/0167682 on Jul. 9, 2007, the endoscope channel 28 may be interrupted, non-continuous or may extend over less than the entire length of the sinus guide body 26. In the embodiment of FIG. 3I, the channel 28 extends along the majority of the length of guide body tube 44 and has a distal end portion that conforms to and hugs the curvature of the curved distal end portion of tube 44. However, the distal end of channel 28 ends proximally of the distal end of tube 44. This setback provides multiple advantages that are described in more detail below. An outer skin 40 may be heat shrunk or otherwise disposed around the sinus guide body 26 and endoscope channel 28 to hold the endoscope channel 28 at a desired position on the outer surface of the sinus guide body 26. In FIG. 3I, heat shrink tube or overlamination 40 surrounds the tubes 44, 28 over a majority of the length of the straight portions of the tubes. Optionally, all or a portion of the curved distal end portions of tubes 44, 28 may be surrounded by heat shrink tubing or overlamination 40d. Proximal end portions of tubes 44, 28 are routed through separate channels in handle 60 that angles the tubes apart as they travel proximally through handle 60, so that luer fittings 45, at the proximal ends of tubes 40, 28 are spread apart further to make it easier to insert tools into the tubes 28, 40 and connect to the luers 45 with less interference from the other channel 28, 40/luer 45. Additionally, the luer 45 for tube 28 can be connected to an irrigation source (saline-filled syringe or other irrigation source) to input irrigation fluid through the lumen of tube 28 to deliver fluid across the viewing tip of endoscope 30 having been inserted in the tube 28, in order to clean the viewing lens. Luer 45 can then be connected to a vacuum source to withdraw the fluid from the lens. Alternatively, irrigation or vacuum may be applied separately, to rinse debris off of the lens or the suction debris off of the lens, respectively. Further alternatively, a suction/irrigation catheter may be inserted through tube 44 to perform these same functions. This may be advantageous when the distal tip of the endoscope 30 has been extended distally of the end of tube 28 and optionally, distally of tube 44.

Alternatively, the endoscope channel 28 may be attached to the sinus guide body 26 at one or more locations by any other suitable attachment substance, apparatus or technique, including but not limited to adhesive, soldering, welding, heat fusion, coextrusion, banding, clipping, etc. The particular circumferential location of the endoscope channel 28 can be important in some applications, particularly when the sinus guide body 26 includes a curve formed in its distal portion 44. In this regard, for some applications, the endoscope channel 28 may be affixed at a particular circumferential location on the sinus guide body 26 to allow a flexible fiber endoscope 30 inserted through the endoscope channel 28 to provide a view from a desired or optimal vantage point, without obstruction from adjacent anatomical structures. This is described in more detail in U.S. patent application Ser. No. 11/647,530, published as U.S. Pub. No. 2007/0167682 on Jul. 9, 2007. Alternatively, channel 28 may be located interiorly of the lumen of tube 44, and may be positioned at various locations circumferentially about the inner wall of the tube 44. FIGS. 8A-8D show channel 28 mounted to the inner wall of tube 44 at 6 o'clock, 3 o'clock, 12 o'clock and 9 o'clock positions, respectively with regard to tube 44. It is noted that placement is not limited to the four relative locations shown, as channel may be positioned intermediate of any two of the adjacent locations shown.

The curve in the distal end portion of channel 28d, when fixed/static with regard to tube 44, must accommodate the rigidity of a distal tip portion of an endoscope as it is passed therethrough, as the endoscope 30, although flexible over the majority of its length, is rigid over a small length extending from the distal tip that contains a lens. In one example, an endoscope channel 28 having an inside lumen diameter of about 0.045" can accommodate a rigid distal tip length of about 0.125" on a flexible endoscope 30 having an outside diameter of about 0.0375" with the curved portion of the channel 28 having a radius of curvature as low as about 0.28". In one particular example, the radius of curvature is about 0.40". For an endoscope having a rigid distal tip length of about 0.150", channel 28 having an inside lumen diameter of about 0.045" can have a curved portion having a radius of curvature as low as about 0.40" when the outside diameter of the endoscope is about 0.0375". In one particular example, the radius of curvature is about 0.58" for the rigid distal tip length of about 0.150".

Figure 2:
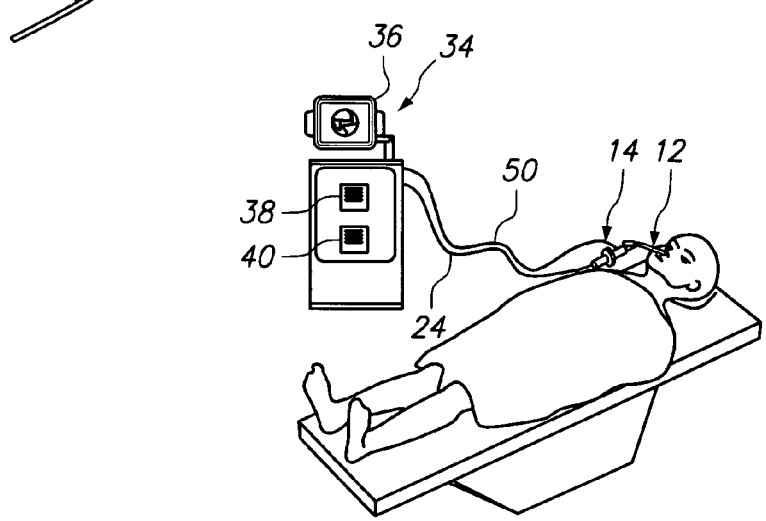
FIG. 2 is a perspective view of the guide system of the present invention in use on a human subject.

A camera/cable/endoscope assembly 14 is attachable to arm 43a or the lower luer fitting 45 shown in FIG. 3I. In the particular embodiment shown in FIGS. 1 and 3L, the camera/cable/endoscope assembly 14 comprises an adjustable scope/lock extension 16, an endoscope 18 having an elongate flexible scope body 30 and integrated light cable 50, a camera 20 and a monitor cable 24. The scope body 30 is advanced through the scope/lock extension 16 and through the lumen 29 of the endoscope channel 28. As shown in FIG. 2, the light cable 50 and monitor cable 24 may be connected to console 34 that houses a monitor 36, light source 38 and video recorder 40.

Figure 3D:
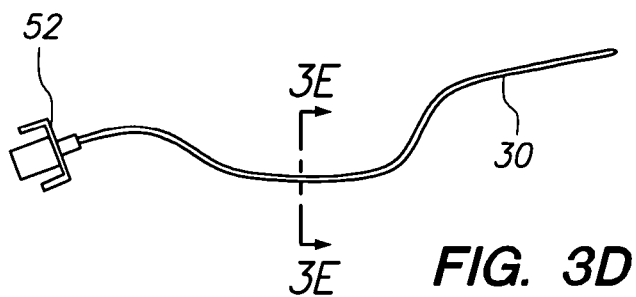
FIG. 3D is a side view of the endoscope of the system of FIG. 1.
Figure 3E:
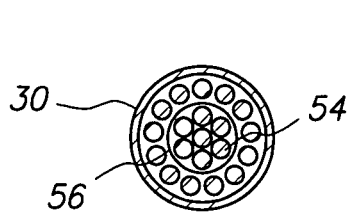
FIG. 3E is a cross sectional view through line 3E-3E of FIG. 3D.
Figure 3F:
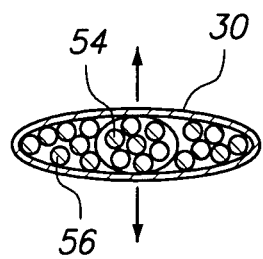
FIG. 3F is a cross-sectional view of a low profile endoscope.
Figure 3G:
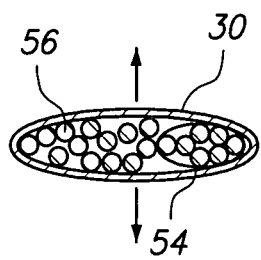
FIG. 3G is a cross-sectional view of another embodiment of a low profile endoscope.

FIGS. 3D and 3E show a flexible endoscope 30 attached to a proximal body member 52 that engages and attaches to the adjustable scope/lock extension 16. As seen in the cross section of FIG. 3E, the scope 30 comprises a flexible shaft having an image fiber bundle 54 that extends coaxially through the center with light transmitting fibers 56 disposed about the periphery. In one embodiment, the flexible shaft is a braided polyimide sheathing that has a maximum outer diameter of 0.0375 inches and a length of two feet. The image fiber bundle may be made up of about 10,000 thin image fibers and the light transmitting fibers may be illumination fibers with a diameter of between about 0.008 and 0.020 inches, with a minimum lux of about 10,000. Preferably, the distal end of the flexible shaft has a lens with a minimum field of view of about seventy degrees. FIG. 3F is a cross-sectional illustration of a flexible endoscope 30 having a low profile configuration. In this arrangement, the flexible shaft has an image fiber bundle 54 that extends coaxially through the center of the shaft with light transmitting fibers 56 disposed laterally of the image fiber bundle. Although light transmitting fibers are shown disposed laterally on both sides of image fiber bundle 54, light transmitting fibers 56 may alternatively be located all on one side of optical fiber bundle 54, as illustrated n FIG. 3G. With either of these arrangements, the height profile of the endoscope shaft 30 is reduced which allows channel 28 to, in turn be lower profile, thereby reducing the cross-sectional size of the device 12 allowing for it to be more easily advanced through the patient anatomy. For example, the cross-sectional shape of such a low profile endoscope 30 may be substantially oval, as shown in FIGS. 3F-3G, or elliptical Additionally this lowered profile makes the shat of endoscope 30 easier to bend/more flexible when bending in the direction of the arrows shown, and this may allow for a smaller radius of curvature in the curved portion of channel 28 when channel 28 is provided with a curve in a distal portion thereof.

FIG. 3H illustrates a steering mechanism provided in endoscope 30 that can be operated from a proximal end portion of endoscope 30, outside the patient's body, to steer a distal tip 30d or portion thereof (e.g., lens barrel 30e) to allow directional control of the visual field provided by endoscope 30. As shown, steering mechanism 30s includes a wire extending through endoscope shaft 30 and attached to a side of lens barrel 30e, so that when tension is applied via a user pulling on a proximal end portion of wire 30s, lens barrel 30e is deflected or angularly directed in the direction shown by the arrow in FIG. 3H. Upon release of tension on wire 30s, lens barrel 30e resiliently returns to its unbiased orientation and direction. The unbiased orientation and direction of lens barrel 30e may be axially aligned with the longitudinal axis of the endoscope 30 shaft. Alternatively, lens barrel may be oriented to point angularly away (downward, in FIG. 3H) from the direction that it is biased toward when tension is applied via steering mechanism 30e. In this way, an intermediate amount of tension may be applied to align the lens barrel 30e with the longitudinal axis of endoscope 30 shaft, and a greater amount of tension can be applied to steer the lens barrel 30e still further in that direction (e.g., pointing angularly upwardly in FIG. 3H). Further alternatively, more than one wire or other steering actuators 30s may be attached to lens barrel 30e for directionally pointing the lens barrel 30e. In different directions. As one non-limiting example, a second wire 30s can be mounted on an opposite side of lens barrel 30e to the side in which the first wire 30s is shown mounted in FIG. 3H. As another example, four wires 30s can be mounted at ninety degree intervals around the circumference of barrel 30e. Further arrangements for controlling along different directions may also be provided, as would be apparent to one of ordinary skill in the art, after reading the above description.

FIG. 3J is a partial view of a sinus guide 12 in which channel 28 is detachable from tube 44. For example, channel 28 may be attachable to and detachable from tube 44 via snap fit, such as by assembling one or more snap fittings 51 on tube 44. Snap fitting 51 includes an enclosed lumen 44l through which tube 44 is received, and which forms a friction fit with tube 44, and a lumen 28l with an opening that allows channel 28 to be inserted therethrough. The width of the opening 28o is less than the outside diameter of channel 28, so that when channel 28 is pushed therethrough, the legs on opposite sides of the opening 28o are deformed outwardly to allow tube to pass therethrough. When channel 28 has seated in lumen 28l, the legs resiliently snap back into the configuration shown in FIG. 3K, thereby retaining tube in lumen 28l by a snap fit. Alternatively, lumen 28l can be enclosed and lumen 44l provided with an opening, in which case snap fitting 51 would be slid longitudinally over channel 28 to form a friction fit therewith and tube 44 would be inserted through an opening to perform the snap fit. Further alternatively, channel 28 may be provided as attachable and detachable to and from tube 44 via hook and loop type fasteners, adhesives that remain sticky and are thus reusable, or other quick release mechanical fasteners.

The provision of attachable/detachable tube 48 makes it easier to match the curve of the distal end portion of channel 28 to the rigidity characteristics of the endoscope 30 to be inserted therethrough, particularly the length of the rigid distal tip portion. Thus, for example, a kit of tubes 28 having distal end portions of varying curvatures (and, optionally, having varying lumen diameters) may be provided so that an appropriate channel 28 can be selected by a surgeon to accommodate the rigidity characteristics of the particular endoscope to be inserted therethrough, and then the selected tube can be attached to tube 44.

Alternatively, channel 28 may be inserted independently of tube 44, which may make it easier to locate the distal end portion of channel 28 in a target cavity. However, when used separately, this requires use of a second hand, one to manipulate tube 44 and a second to manipulate channel 28.

As noted above, the distal end of channel 28 can end proximally of the location of the distal end of tube 44, so that the distal end of channel 28 is located proximally of the distal end of tube 44 by a setback distance 53. Setback distance 53 may be about one mm to about four mm, typically about two mm, for sinus guides having statically placed tubes 28. As noted above, placement of channel 28 on a relative location about the circumference of tube 44 may vary, for example for various uses in the frontal, maxillary and/or sphenoid sinuses. Setback 53 allows the distal end of endoscope 30 to be advanced distally beyond the distal end of channel 28 without extending distally beyond the distal end of guide body tube 44, thereby adding protection to the distal end of the endoscope 30 while allowing better visualization when the tip is distally extended from the distal end of channel 28. This can be particularly advantageous during advancement of the device 12, for example.

Additionally, setback 53 also reduces the distal profile of the guide device 12, facilitating entry and passage through smaller openings than allowable by a device that has a distal tip cross sectional area formed by the combined cross sectional areas of tube 44 and channel 28. Setback 53 also provides a tapering effect, reducing the physical impact from endoscope channel 28 as it is traversed through the patient's anatomy.

A distal end portion of channel 28 (including at least distal tip portion 28d, but which may extend proximally thereof) may be colored with a color that contrasts with a color of the remainder of the channel. This provides visible notice to the user, during traversal of endoscope 30 over or through channel 28, when the viewing (distal) tip of endoscope 30 has reached the portion having the contrasting color, as the contrasting color can be visualized on the inner wall surface of the channel (e.g., lumen), so that the user is aware that the tip of the endoscope is about to be delivered distally of the distal end of channel 28. This is possible even when channel 28 is a stainless steel tube. As the scope 30 travel through the steel tube 28, even abrasions in the steel on the inner surface (lumen) are visible. When the endoscope transitions from the steel tube 28 to the polymer atraumatic tip that is colored with a contrasting color, a colored ring is visible, which is the inner wall surface of the colored polymer distal tip 28d. Additionally, or alternatively, a distal tip portion of tube 44 can be colored with a contrasting color so that this can be visualized as the distal tip of endoscope is exiting the distal end of channel 28, especially in situations where the distal end of channel 28 is proximally set back from the distal end of tube 44.

Figure 4A:
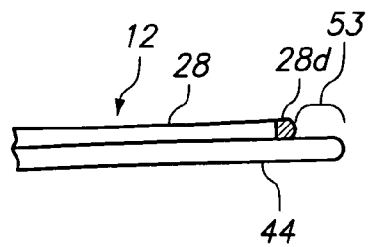
FIG. 4A shows a distal portion of a guide device configured with a static channel, for accessing a sphenoid sinus.
Figure 4B:
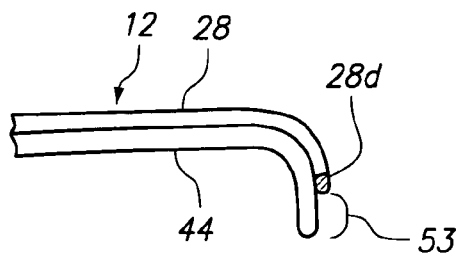
FIG. 4B shows a distal portion of a guide device 12 configured with a static channel, for accessing a frontal sinus.

The distal tip of channel 28d is preferably formed as an atraumatic tip, having a rounded distal edge. As noted, tip 28d may be formed of stainless steel or other hard material. In this case the rounded edge makes the tip more atraumatic. Alternatively, tip 28d may be formed of a softer material such as PEBAX™, SANOPRENE™ (synthetic rubber), silicone, PELLETHANE™ (thermoplastic polyurethane elastomers), or other soft plastic, which, when formed with a rounded distal edge, even further increases atraumaticity. By providing the atraumatic distal edge, the helps prevent cutting and other damage to tissues as guide device 12 is advanced through the patient's anatomy, which may include pushing through tissue, where the atraumatic tip(s) act more like blunt dissectors than cutting instruments. The distal tip of tube 44 can be formed similarly to any of the embodiments of the atraumatic distal tip of channel 28 described above. FIG. 4A shows a distal portion of device 12 configured with a static channel 28, for accessing a sphenoid sinus, for example, having tube 44 and channel 28 provided with atraumatic, rounded tips, and wherein a distal tip portion 28d of channel 28 is colored with a color that contrasts with a portion of channel 28 immediately proximal of tip 28d. FIG. 4B shows a distal portion of device 12 configured with a static channel 28, for accessing a frontal sinus, for example, having tube 44 and channel 28 provided with atraumatic, rounded tips, and wherein a distal tip portion 28d of channel 28 is colored with a color that contrasts with a portion of channel 28 immediately proximal of tip 28d.

Figure 5A:
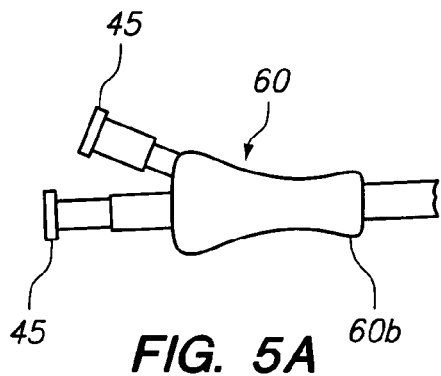
FIG. 5A illustrates a partial plan view of a guide device showing one embodiment of a handle.
Figure 5B:
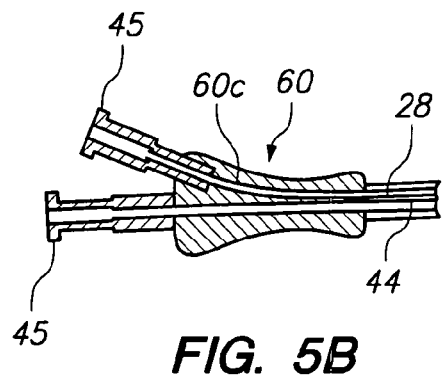
FIG. 5B illustrates a longitudinal sectional view of FIG. 5A.

FIG. 5A illustrates a partial plan view of device 12 showing one embodiment of handle 60. FIG. 5B illustrates a longitudinal sectional view of FIG. 5A. Handle 60 accommodates channel 28 and tube 44 to pass therethrough and extend proximally thereof to join with connectors 45. Handle 60 may be molded over tube 44 and channel 28 in the configuration shown, or may be molded separately with channels configured and dimensioned to receive channel 28 and tube 44 therethrough (e.g., molded in halves and then assembled over the tube 44 and channel 28, using screws, clamps, adhesives, press fitting, and/or other connectors). Alternatively, the handle can be molded or machined as one piece and the lumens can then be slid into place and fixed with adhesive and/or threaded connection, etc. Handle 60 is shaped to fit a user's hand, and to be easily rotated by the user. Accordingly, handle 60 may be substantially barrel-shaped, cylindrical, or other shape that lends itself to rotation about its longitudinal axis (e.g., rounded about the longitudinal axis, or octagonal or other extruded polygonal cross-section).

The outer surface of handle 60 can be smooth for easy sliding within the hand, or can be provided with a roughened surface to enhance the grip, for pushing on the handle 60 and/or torquing it. The distal end portion is formed with an uplift, "bump" or increased cross-sectional area 60b, relative to the mid portion of the handle, to act as a stop against the hand of the user, thereby preventing the hand from sliding distally off of the handle 60 during use.

Channel 28 is guided away from tube 44 at the proximal end portions thereof, such as by an angled or curved channel 60c that directs the proximal end portion of channel 28 away from tube 44 as channel 28 passes through the channel 60c. This provides greater separation between the connectors 45, facilitating easier insertion of endoscope into channel 28 and tools or devices (e.g., balloon catheter, or any of the other devices or tools described herein or in U.S. patent application Ser. No. 11/647,530, published as U.S. Pub. No. 2007/

0167682 on Jul. 9, 2007; U.S. patent application Ser. No. 11/522,497, issued as U.S. Pat. No. 7,559,925 on Jul. 14, 2009; U.S. patent application Ser. No. 11/193,020, published as U.S. Pub. No. 2006/0063973 on Mar. 23, 2006; U.S. patent application Ser. No. 10/829,917, issued as U.S. Pat. No. 7,654,997 on Feb. 2, 2010; U.S. patent application Ser. No. 11/116,118, issued as U.S. Pat. No. 7,720,521 on May 18, 2010; and/or U.S. patent application Ser. No. 11/150,847, issued as U.S. Pat. No. 7,803,150 on Sep. 28, 2010; without interference from the other connector 45. Bend or curve 60c also creates force feedback and acts as a frictional braking system as endoscope 30 is advanced through channel 28 at the location of the bend or curve in channel 60c, facilitating greater control of the advancement of the endoscope 30 by the user, with less risk of inserting too quickly or impulsively, or overshooting the amount of insertion. Additionally, this helps maintain the endoscope in longitudinal position relative to channel 28 even when an additional locking mechanism or valve is not provided.

Both tube 44 and channel 28 may be provided with a luer connector 45 on proximal ends thereof, to allow for attachment of a syringe for flushing, or attachment of other tools. A Touhy valve or other valve can be alternatively fitted on the proximal end of channel 28 to facilitate locking of the endoscope 30 in a position relative to channel 28. Further alternatively, a Y-adapter may be fitted to the proximal end of channel 28 to permit fixation of luer 45 to one arm of the Y and a valve to the other arm. Numerous other accessories can be attached to either channel 28 or tube 44, including drip systems, pop-off valves, etc.

Figure 6A:
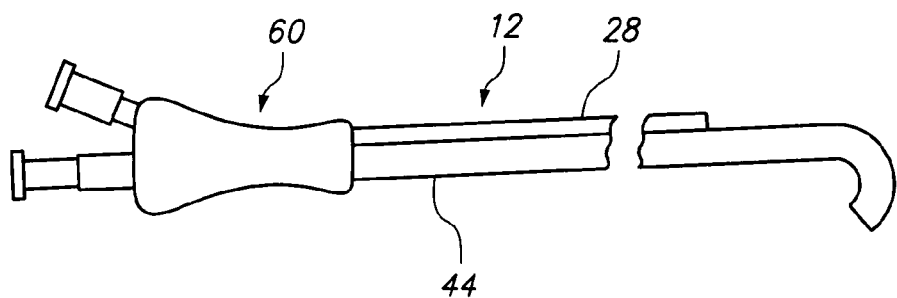
FIG. 6A illustrates another embodiment of a guide device.

FIG. 6A illustrates an embodiment of sinus guide device 12 wherein endoscope channel 28 is fixed relative to handle 60 and tube 44 is rotatable about its longitudinal axis within handle 60. Accordingly, the location of channel 28 relative to tube 44 can be varied by rotating handle 60 and holding the luer connector 45 that connects to tube 44 stationary as the handle 60 is rotated. This causes channel 28 to revolve about the longitudinal axis of tube 44, thereby repositioning the radial position of channel 28 relative to tube 44. For example, with channel 28 in a radial position at the top of tube 44 as illustrated in FIG. 6A, luer 45 connected to tube 44 can be grasped and prevented from rotating while rotating handle 60. By rotating handle 60 by 180 degrees, this results in channel 28 being positioned at the bottom side of tube 44. This rotatability to reposition channel 28 provides re-orientation of the view provided through endoscope 30 that is positioned through or over channel 28. The channel in handle 60 receiving tube 44 provides some frictional resistance to rotation of tube 44 relative thereto, so that tube 44 will not rotate relative to handle 60 during use of device 12, except when the user deliberately holds the connector 45 or tube 44 to prevent it from rotating and then rotates handle 60. FIG. 6A also shows channel 28 having a distal tip positioned proximally of the curved section of tube 44. This may be advantageous for example, for use in the maxillary sinus, to provide a larger, or wider angle view of the maxillary sinus by setting the distal tip of channel 28 proximally away from the curve. It is noted that the rotatability functions and features described with regard to FIG. 6A are not limited to this embodiment with a shortened channel 28, For example, this rotatability can also be provided with a device 12 like that shown in FIG. 4A.

Figure 6B:
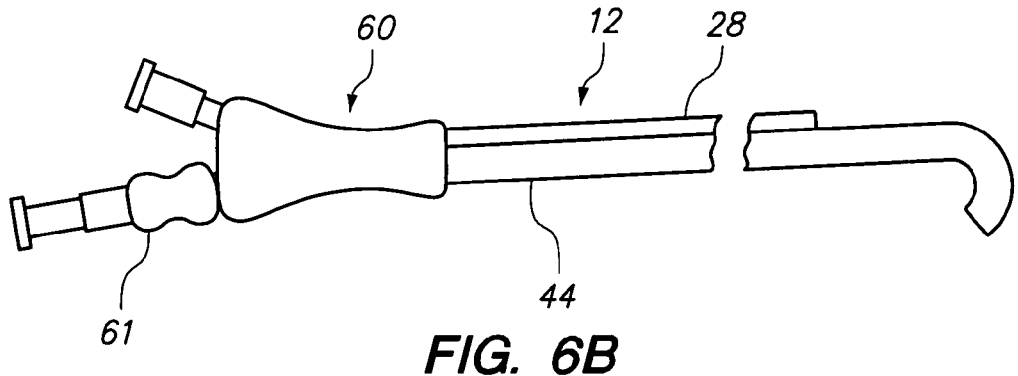
FIG. 6B illustrates another embodiment of a guide device.

FIG. 6B illustrates a variation of a rotatable device 12. In this arrangement, a second handle 61 is provided proximally of handle 60. Handle 61 is fixed relative to tube 44, so that the user can hold handle 61 to prevent it and the tube 44 from rotating as the user rotates handle 60 to revolve channel 28 about tube 44. Optionally, handle 61 may be spring-biased into contact with handle 60 to act as a brake to prevent handle 60 from rotating relative to handle 61. In order to perform a rotation in this case, the user pulls handle 61 proximally out of contact with handle 60 to relieve the braking force and allow the user to rotate handle 60 while holding handle 61 stationary. Further optionally, the frictional force imposed by handle 61 against handle 60 may be great enough to prevent relative rotation during use of device 12, but can be overcome by the user twisting on handle 60 and holding handle 61 stationary, without the need to retract or reposition handle 61 relative to handle 60. As with the embodiment of FIG. 6A, the embodiments of the rotational features described with regard to FIG. 6B can be employed in other guide device 12 embodiments, and are not limited to a device having a channel 12 that ends proximally of a bend in tube 44.

Figure 7A:
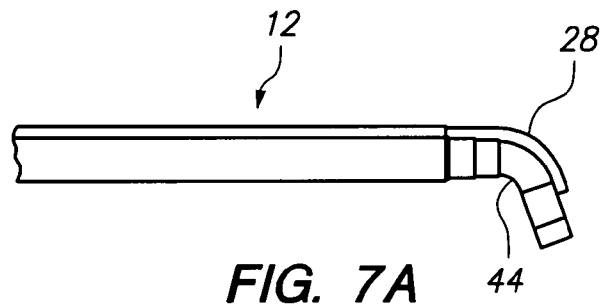
FIGS. 7A-7C illustrate distal end portions of guide devices having curved sections with each with a different radius of curvature.
Figure 7B:
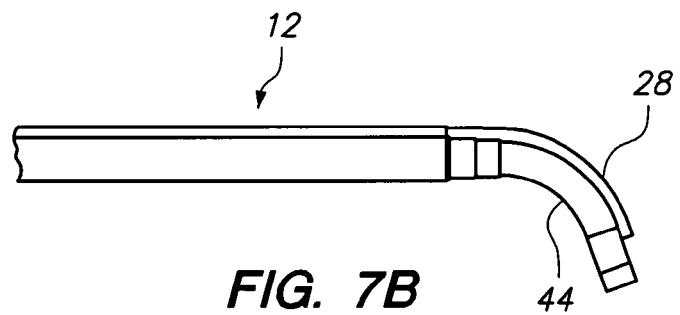
Figure 7C:
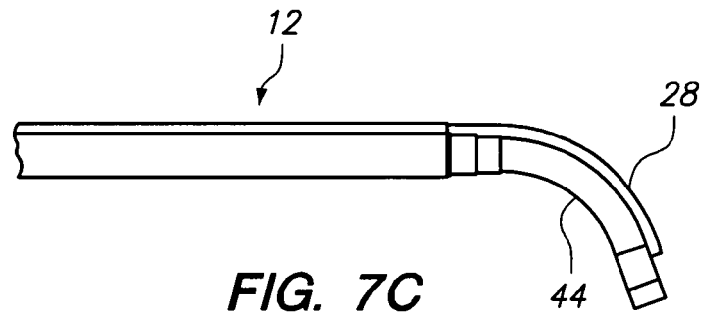
Figure 8A:
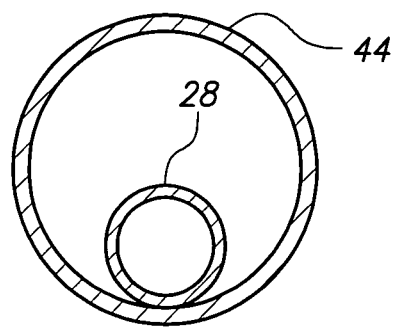
FIGS. 8A-8D are cross-sectional illustrations showing various placement locations of an endoscope channel within a main tube of a guide device.
Figure 8B:
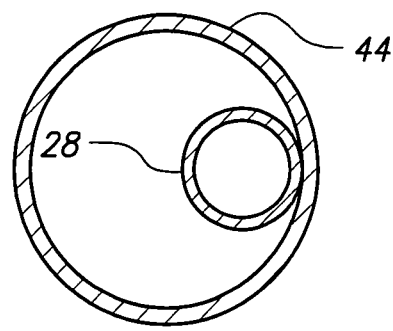
Figure 8C:
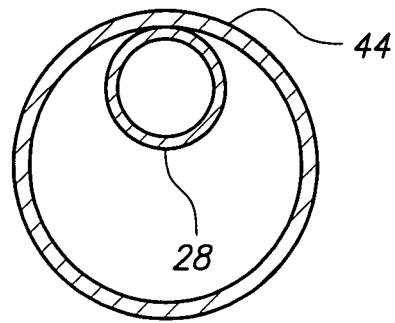
Figure 8D:
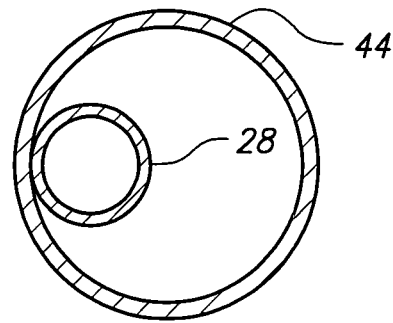

For devices 12 in which distal end portions of tube 44 and channel 28 are curved, and channel 28 comprises a tube, the radius of curvature can be designed to readily allow the endoscope 30 (and particularly the distal tip portion that includes the lens, which may be rigid) to move through the lumen of tube 28 and around the curve without the need to increase the inside diameter of the lumen, so that the lumen can be designed with a inside diameter having only a small tolerance around the outside diameter of endoscope 30. Typically, standard 18 gauge hypotube is used having an outside diameter of about 0.050". The wall thickness selected is as thin as possible, to maximize the inside diameter of the tube without risking buckling of the tube. Typically the wall thickness is about 0.003". In one particular example, the tube is 18 Gauge UTS with an outside diameter of 0.050"+0.001"/−0.0005", with an inside diameter of about 0.044" and therefore a tolerance of about +0.0015/−0.001". Alternatively, the inside diameter of tube 28 can be increased if the curvature of the distal end portion is required to have a radius of curvature that would not allow endoscope to pass otherwise. The amount of curvature that can be successfully used with a lumen of normal tolerance relative to the outside diameter of endoscope 30 will also vary with the degree of flexibility of the endoscope 30 and the length of the lens barrel 30e. In other words, the longer that the stiff section (lens barrel and adhesive) is, the bigger is the required inside diameter of tube 28 and/or the bigger the required radius of curvature of a bend in a tube 28 to allow easy passage of the stiff section. FIGS. 7A-7C illustrate exemplary distal end portions of devices 12 in which the curvatures of tubes 28, 40 are varied, wherein the larger the radius of curvature, the easier it is to pass endoscope therethrough, with all other variables being constant. In FIG. 7A, the radius of curvature is about 0.25 inches, in FIG. 7B, the radius of curvature is about 0.5 inches, and in FIG. 7C, the radius of curvature is about 0.75 inches. The insider diameters of the tubes 28 in these examples are 0.044"+0.0015"/−0.001".

In order to reduce the distal end profile of the guide device 12, tube 44 may be provided with a non-circular cross-section at the distal end thereof. By reducing the distal end profile, this facilitates entry and passage through smaller openings or relatively more constrained spaces, such a may be encountered in the passages leading to the frontal or maxillary sinuses, or other spaces relatively constrained by the patient's anatomy, as the reduced cross-sectional profile of the distal end of tube 44 is more readily able to be introduced into and smaller or partially obstructed spaces, compared to tubes having a full circular distal end cross-section. FIG. 9A illustrates tube 44 having a standard, circular cross-section at its distal end. FIG. 9B illustrates tube 44 having a reduced cross-sectional area at its distal end, in this case formed by a scooped-tip 44t. Because a portion of the distal end of tube 44 is cut away to form the scooped tip, the profile of the distal end of tip 44*t* is significantly less than that of the tube 44, as illustrated by comparing FIGS. 9C and 9D, which illustrated the distal end profiles of the tube 44 in FIGS. 9A and 9B, respectively. Accordingly, the cross-sectional profile of the scooped tip 44*t* tapers down from that of a circular profile, at a proximal end of the scooped tip 44*t*, to a semi-circle or less at the distal end of the scooped tip 44*t*. In addition to the advantages noted above, a tube 44 having reduced-profile tip, such as a scooped-tip 44*t*, for example, may facilitate entry into, or closer position to ostia by the distal end of a guide device 12. The scooped tip 44*t* design may also facilitate balloon retraction (of a balloon catheter), back into tube 44 after performing an ostial dilatation procedure, for example.

In particular, with regard to the maxillary sinus, the tapered cross-section provided by scooped tip 44*t* allows the distal end of tube 12 to be easily passed behind the uncinate process. In the frontal recess, the scooped tip 44*t* may provide additional freedom of movement of device 12.

In addition to providing a significantly reduced cross-sectional area at the distal end, scooped tip 44*t* of FIG. 9B also provides a larger opening than the circular opening of the standard tube end, like shown in FIG. 9A, for tubes 44 having the same inside diameter. Accordingly, as mentioned above, this may make it easier to retract a balloon portion of a balloon catheter back into the lumen of tube 44, e.g., after performing a dilatation procedure and deflating the balloon. Additionally, the curvature of the sides of the scope shape, tapering down to the proximal end of the scoop shape can facilitate folding of the balloon as it is retracted into the lumen of tube 44.

The scooped tip 44*t* can be provided on a guide device 12 that does not include an endoscope channel, as illustrated above with regard to FIG. 9B. Further the advantages discussed above can also be provided to a guide device 12 that does include a channel 28 integrated therewith. The channel 28 may be fixed relative to tube 44 and may be removably fixed, as described previously. FIG. 10A illustrates an example of guide device 12 having a fixed channel 28 that extends so that the distal end of channel 28 is substantially flush with the distal end of scooped tip 44*t*. Although this arrangement is not preferred as it is preferred to provide a setback, even with this arrangement, the reduced cross-sectional profile at the end of scooped tip 44*t* compensates, or helps to compensate for the additional cross-section profile of the end of channel 28. That is, the cross sectional dimension 12×1 is less than the cross-sectional dimension 12×2 measured across the distal ends of tubes 44 and 28 when tube 44 has a circular profile distal end as shown in FIG. 10B.

An even greater advantage in reducing the distal end profile of a device 12 having both tube 44 and channel 28 can be obtained by orienting the distal end of channel 28 with a setback 53 as described above and as illustrated in FIGS. 10C and 10D. Regardless of whether the bend in the tube 44 and channel 28 is an acute angle or an obtuse angle (or right angle), the distal end cross-sectional dimension 12×1 is greatly reduced relative to 12×2 in FIG. 10B, and even the cross-sectional dimension 12×3 that includes the profile of channel 28, but is set back from the distal end of device 12, is reduced relative to 12×2.

Optional Linkage of Endoscope to Working Device

Figure 11:
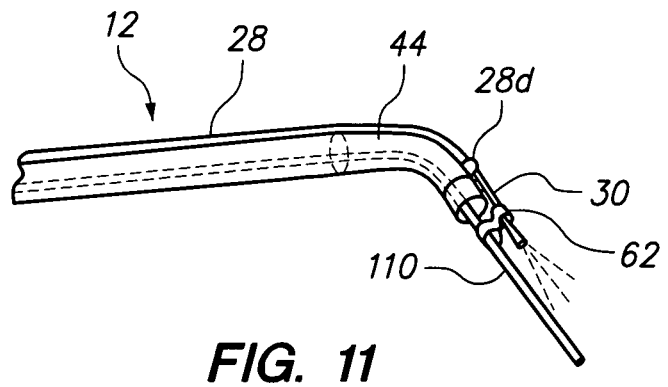
FIG. 11 is a partial perspective view of a guide device of the present invention with an optional linking apparatus for linking the endoscope to a working device to deter divergence of the endoscope away from the path of the working device.

In some applications, it may be desirable to advance the flexible endoscope 30 out of and beyond the distal end of the endoscope channel 28, 28*d*, and even beyond the distal end of tube 44. For example, as shown in FIG. 11, the endoscope 30 may sometimes be advanced along side a working device, such as a guidewire 110, so as to view the advancement, positioning and/or use of the working device. In such instances, it is desirable to prevent the endoscope from diverging away from the working device and/or to maintain the endoscope 30 at a specific spaced distance away from the working device. To accomplish this, an optional linkage device 62 may be used to link (e.g., couple, connect or attach) the endoscope 30 to the guidewire 110 or other working device. Other working devices that may be inserted through tube 44, and optionally linked to endoscope 30 via linkage device 62, include, but are not limited to: graspers, catheters, instrument or other device useable to perform or facilitate a therapeutic or diagnostic task such as local or regional drug delivery, biopsy, suction, irrigation, polyp removal, fungal ball removal or other mass removal.

Operation and Positioning of the Endoscope and Working Device

As noted, the flexible fiber endoscope 30 may be freely advanced to or beyond the end of the sinus guide 12 and retracted during use, in order to facilitate endoscopic viewing of the desired anatomical structures and/or to view, guide and/or verify the positioning of the sinus guide device 12 or a working device that has been inserted through the sinus guide. The ability to advance the tip of the flexible fiber endoscope 30 beyond the end of the sinus guide allows the tip to be positioned closer to anatomy or to reach spaces in the paranasal sinuses that the sinus guide tip cannot travel to due to size constraints.

Figure 12:
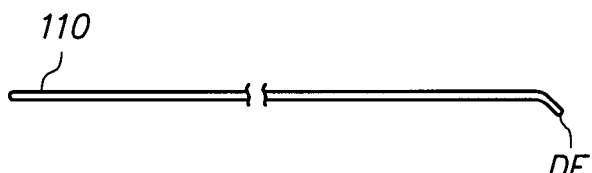
FIG. 12 is a side view of a guidewire having an angled distal tip.
Figure 13A:
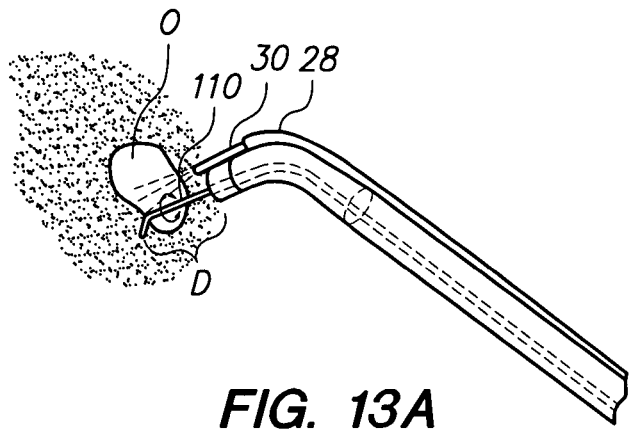
FIGS. 13A shows a step in a method for using a guide system of the present invention in conjunction with the guidewire of FIG. 12.
Figure 13B:
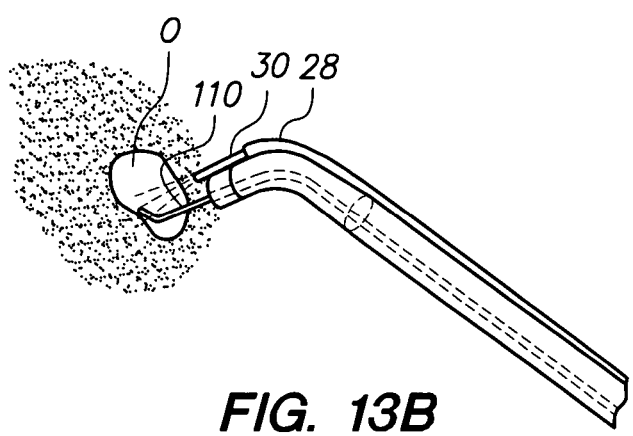
FIG. 13B shows another step in a method for using a guide system of the present invention in conjunction with the guidewire of FIG. 12.

In some instances, it may be desired to advance a guidewire 110 into or through a specific body opening, such as an opening of a paranasal sinus. In such applications, as shown in FIG. 12, it is sometimes desirable to form a bend in the guidewire 110 near its distal end DE so that rotation of the guidewire in situ will redirect its distal end DE. The guidewire may be maneuvered into the opening by simply rotating the guidewire 110. FIGS. 13A and 13B show an example of such a procedure, wherein the guide device 12 is advanced to a position where its distal end is a spaced distance D from the opening O into which the guidewire 110 is to be inserted. In some instances, the user may use fluoroscopy and/or a surgical navigation system to position the guide device as described in previous applications noted above. With the guide device 12 so positioned, an endoscope inserted through the endoscope channel 28 may be used to view the distal end DE of the guidewire 110 as it advances out of the distal end of the sinus guide body tube 44. With the flexible endoscope 30 so positioned, the user has a view generally along the same axis as the distal opening of the guide device, rather than the proximal axis of the guide device. Furthermore the view can be from behind anatomy that normally would block a conventional endoscope view. In FIG. 13A, the view provided by the endoscope allows the operator to see that the distal end of the guidewire 110 is not directed into the opening O. As a result, the operator may rotate the guidewire 110 causing its distal end DE to be directed into the opening O as verified by the view provided from the endoscope. Thus, in these sorts of applications, it is desirable to place the distal end of the sinus guide device 12 at a spaced distance D back from the opening O rather than advancing it to a point where the distal end of the sinus guide body is immediately adjacent to or within the opening O. In an alternative embodiment, the guidewire can be an illuminating guidewire as described in co-pending U.S. patent application Ser. No. 11/522,497, issued as U.S. Pat. No. 7,559,925 on Jul. 14, 2009 and U.S. patent application Ser. No. 11/647,530, published as U.S. Pub. No. 2007/0167682 on Jul. 9, 2007, or as described herein.

Use of Flexible Endoscope with Intra-Sinus Procedures

Many current FESS procedures are performed to open sinus ostia. Also, balloon dilatation of sinus ostia can be performed in a balloon sinuplasty procedure, embodiments of which have been discussed previously in co-pending applications incorporated by reference herein. The flexible endoscopes described herein can be utilized, with or without guide device 12 to facilitate direct visualization of such procedures.

However, until now, the number of procedures performed inside a sinus cavity have been limited, due to challenges with visualizing such procedures, since direct visualization was not possible, due to the prohibitive profile sizes and rigidity of endoscopes conventionally used in the procedures. The current invention provides flexible endoscopes 30 as small as about one mm outside diameter and may be semi-rigid. This small outside diameter of endoscope 30 permits it to be inserted through an ostium either pre- or post-dilation of the ostium to provide direct visualization inside the sinus cavity. This visualization capability may therefore facilitate direct viewing of intra-sinus therapies, treatments and procedures.

Figure 14:
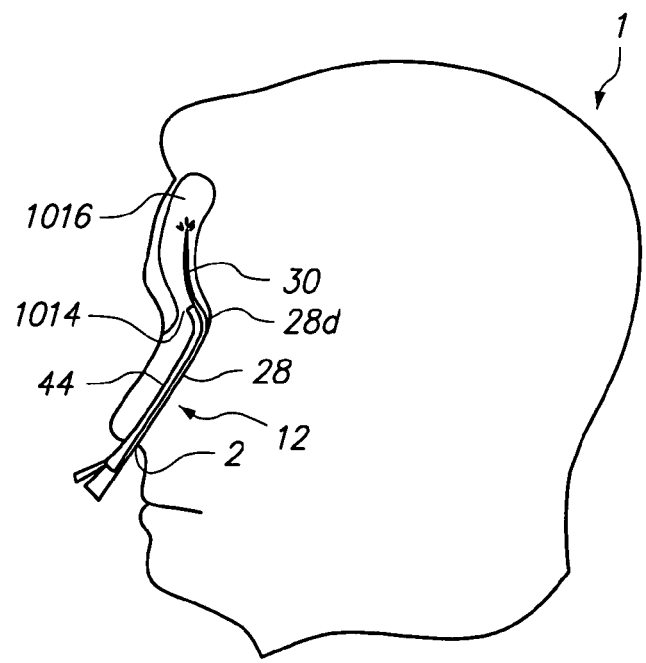
FIG. 14 illustrates an example of a procedure in which a g2ide device has been introduced through a nostril and an endoscope has been delivered through a sinus ostium.

FIG. 14 illustrates an example of a procedure in which sinus guide device 12 has been introduced through a nostril 2 of a patient 1 and through a nasal cavity to a location close to an ostium 1014 of a sinus 1016. Endoscope 30 may be used in a position where the distal tip of the endoscope is flush with the opening 28d of channel 28, extends distally beyond distal end 28d, but not distally beyond the distal end of tube 44, or slightly distally beyond the distal end of tube 44 to provide direct visualization of a procedure to dilate the ostium 1014, for example. In some cases, intra-sinus procedures may be commenced without dilating the ostium 1014. Accordingly, either without dilatation of the ostium 1014, or before of after dilatation of ostium 1014, endoscope 30 is further distally advanced through the ostium to position the distal viewing tip of the endoscope within the sinus 1016, as shown in FIG. 14. A variety of therapies may be delivered into the sinus with direct visualization thereof provided by endoscope 30 positioned in the sinus 1016, including, but not limited to: local or regional drug delivery, biopsy, suction, irrigation, polyp removal, fungal ball removal and/or removal of other mass. Endoscope 30, when positioned in a sinus 1016 may also be useful for intra-sinus diagnosis to assess an underlying disease, to evaluate ciliary function by viewing transport of a dyed fluid, or other diagnostic procedure. These therapeutic and diagnostic procedures may additionally be facilitated by insertion of one or more tools, instrument or devices through the lumen of tube 44 to deliver a working end portion of the tool, device or instrument through the ostium 1014 and into the sinus 1016. A variety of tools, instruments or devices may be inserted through tube 44, including, but not limited to: graspers, cutters, punches, flexible microdebriders, dissectors, electrodes for energy delivery (RF, heat, cryotherapy, ultrasound, or microwave), lasers, suction catheters, irrigation catheters, balloon catheters, etc.

Figure 15:
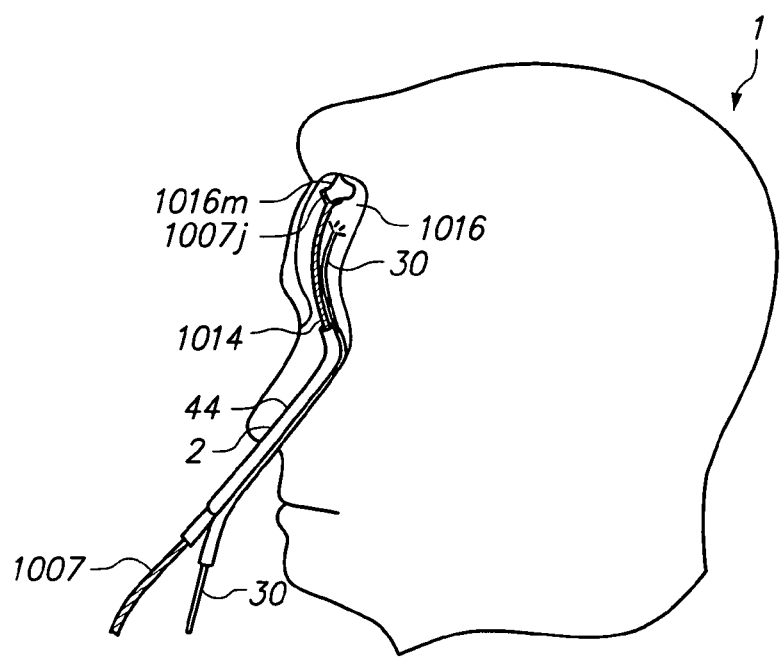
FIG. 15 illustrates a working device having been inserted through the guide device of FIG. 14 and into a sinus cavity.

FIG. 15 illustrates an intra-sinus procedural step in which endoscope 30 has been positioned intra-sinusly, in sinus 1016 in a manner as described above with regard to FIG. 12. Additionally a flexible graspers instrument 1007 has been inserted through a lumen of tube 44 and advanced to deliver the distal, working end into the sinus 1016. By viewing the working end of the graspers 1007 through endoscope 30, and operator can advance the working end and operate the grasping jaws 1007j to approach a mass 1016m in the sinus that is desired to be removed position the jaws 1007 around the mass 1016m or a portion thereof and clamp the jaws to capture the mass 1016m or a portion thereof. By then retracting tool 1007, the mass 1016m or a portion thereof that has been captured by jaws 1007j can be withdrawn through ostium 1014, with visualization of all of these steps being facilitated through endoscope 30. The mass 1007j or a portion thereof having been captured and torn away or otherwise removed from the sinus 1016 and through ostium 1014 is then withdrawn through tube 44. Alternatively, viewing of retraction of the mass into the tube 44 can be performed by retracting the distal end of endoscope 30 to a location just proximal of ostium 1014 or just proximal of the distal end of tube 44. Further alternatively, if the mass 1016m is too large to be retracted through tube 44, device 12 can be removed simultaneously with the removal of tool 1007 and the mass 1016m.

It is noted that FIG. 15 is only one example of procedures that can be performed intra-sinusly and that the present invention is by no means limited to this procedure, as many other procedures can be performed, some examples of which were listed above.

Figure 16:
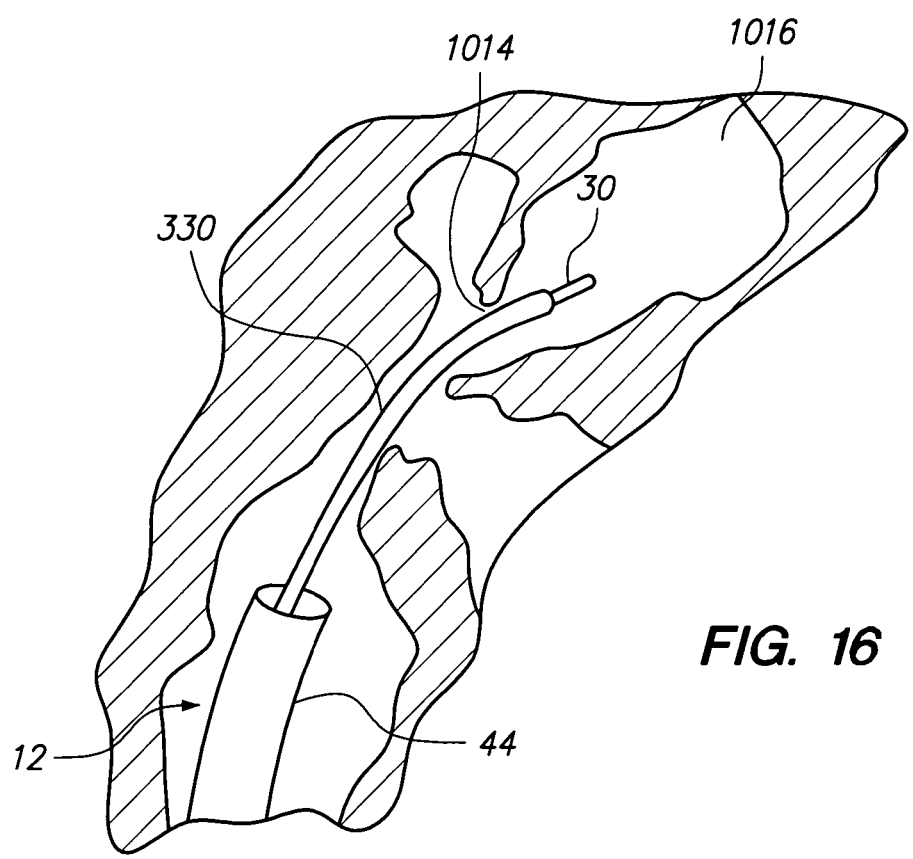
FIG. 16 illustrates a method in which an endoscope has been inserted through a lumen of a working device to enter a sinus cavity.

FIG. 16 illustrates an alternative procedure in which endoscope 30 is inserted through a lumen of a tool, device or instrument having been inserted through tube 44 of guide device 12 and into a sinus cavity 1016. In the example shown, endoscope 30 has been inserted through the lumen of an irrigation catheter 330. Note also that device 12 may include an integrated endoscope channel 28, but need not, since endoscope is delivered through the same lumen in tube 44 that the working tool is delivered through. In the example shown in FIG. 16, device 12 does not include an endoscope channel 28. It is further noted that this technique is not limited to insertion of endoscope 30 through an irrigation catheter, as endoscope 30 may be similarly inserted through any other tool, instrument or device having been inserted through tube 44 and which has a lumen with a sufficient inside diameter to allow endoscope 30 to pass therethrough. Also, although reference here is made to the tool, instrument or device having a distal end portion inserted into a sinus cavity 1016, endoscope 30 may be used similarly to view locations outside of an ostium 1014, when the distal end of the tool, instrument or device has not been inserted through the ostium, or to view some other cavity or space, for example.

In the example shown, an irrigation procedure is first performed in the sinus 1016 prior to insertion of endoscope 30 into the lumen of the irrigation catheter 330. In this particular example, irrigation catheter has a lumen having a diameter of about 0.050" and endoscope 30 has an outside diameter of about 0.0375". Accordingly, after performing irrigation with the distal end of irrigation catheter 330 in the sinus 16, endoscope 30 is inserted through the lumen of the irrigation catheter 330 and advanced to deliver the distal (viewing) tip into the sinus cavity 1016, as shown. The user can then view through endoscope 30 to confirm whether the sinus 1016 has been cleaned out sufficiently by the irrigation process, and/or to inspect the sinus for other potential issues or ailments that might be addressed.

Illuminating Guidewire

Figure 17A:
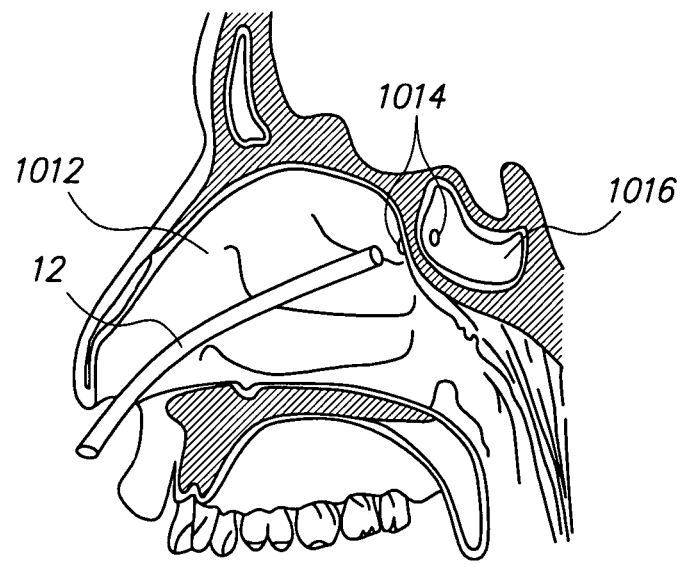
FIGS. 17A-17D are illustrations of partial sagittal sectional views through a human head showing various steps of one embodiment of a method of gaining access to a paranasal sinus using a sinus guide.

FIGS. 17A through 17D are illustrations of partial sagittal sectional views through a human head showing various steps of one embodiment of a method of gaining access to a paranasal sinus using a sinus guide 12. In FIG. 17A, a first introducing device in the form of a sinus guide 12 is introduced through a nostril and through a nasal cavity 1012 to a location close to an ostium 1014 of a sphenoid sinus 1016. Sinus guide 12 may be straight, malleable, or it may incorporate one or more preformed curves or bends as further described above, as well as in U.S. Patent Publication Nos. 2006/0004323; 2006/0063973; and 2006/0095066, issued as U.S. Pat. No. 7,462,175 on Dec. 9, 2008, for example, each of which are incorporated herein, in their entireties, by reference thereto. In embodiments where sinus guide 12 is curved or bent, the deflection angle of the curve or bend may be in the range of up to about 135 degrees.

Figure 17B:
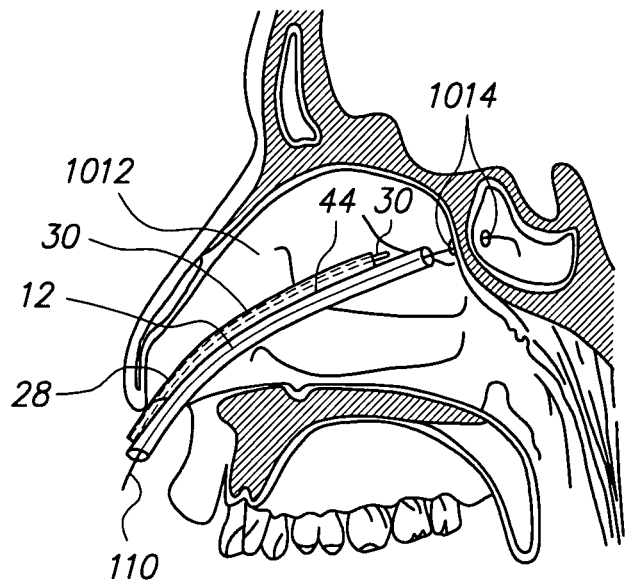

In FIG. 17B, a second introduction device comprising a guidewire 110 is introduced through the first introduction device (i.e., sinus guide 12) and advanced so that the distal end portion of guidewire 110 enters the sphenoid sinus 1016 through the ostium 1014.

Figure 17C:
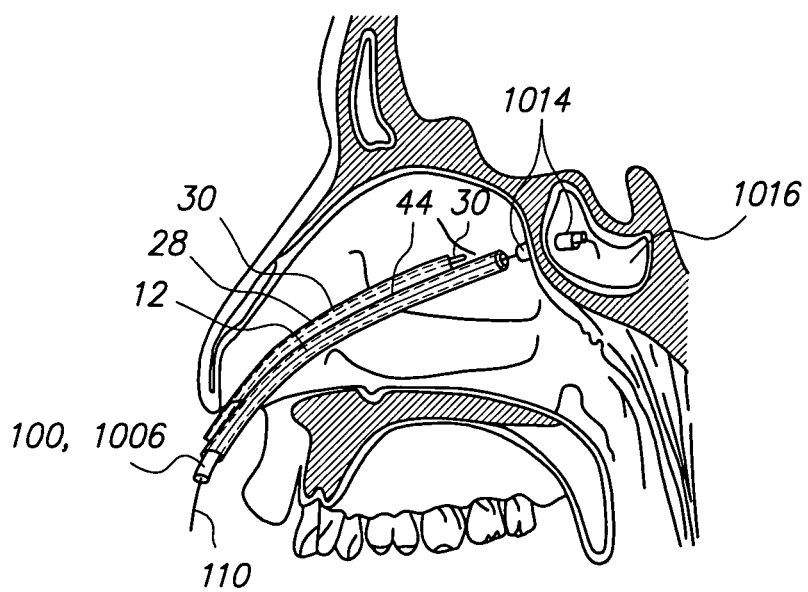
Figure 17D:
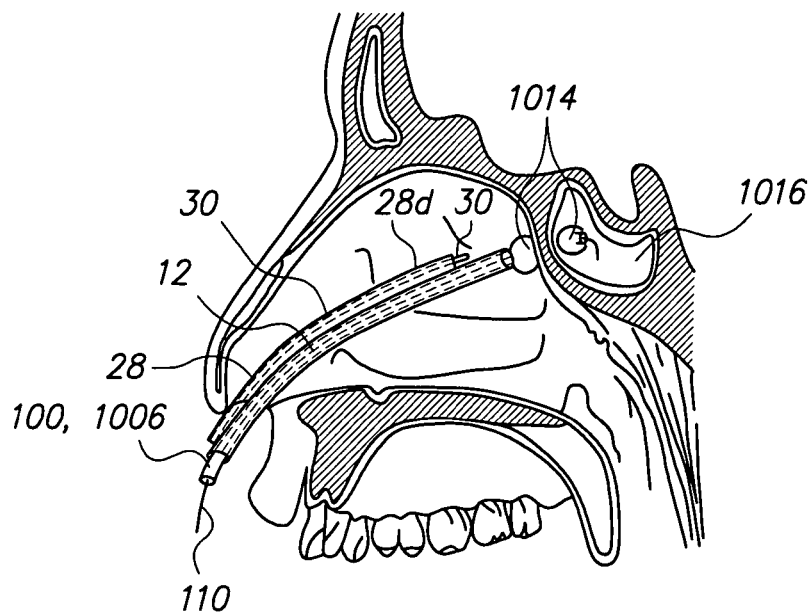

In FIG. 17C, a working device 1006, for example a balloon catheter 100, is introduced over guidewire 110 and advanced to extend the distal end portion of device 1006, 100 into the sphenoid sinus 1016. Thereafter, in FIG. 17D, working device 1006, 100 is used to perform a diagnostic or therapeutic procedure. In this particular example, the procedure is dilatation of the sphenoid sinus ostium 1014, as is illustrated in FIG. 17D, where the balloon of device 1006 is expanded to enlarge the opening of the ostium 1014. After completion of the procedure, sinus guide 12, guidewire 110 and working device 1006, 100 are withdrawn and removed. It will be appreciated that the present invention may also be used to dilate or modify any sinus ostium or other man-made or naturally occurring anatomical opening or passageway within the nose, paranasal sinuses, nasopharynx or adjacent areas. As will also be appreciated by those of ordinary skill in the art, in this or any of the procedures described in this patent application, the operator may additionally advance other types of catheters, and that guidewire 110 may be steerable (e.g. torquable, actively deformable) or shapeable or malleable.

FIGS. 17B-17D show endoscope 30 having been inserted through channel 28 to provide visualization of advancement of sinus guide 12 and/or inserted alongside sinus guide 12 to provide visualization of all or at least a portion of working tool 1006, 100. It is to be appreciated that scope 30 may comprise any suitable types of rigid or flexible endoscope and such optional scope may be separate from or incorporated into the working devices and/or introduction devices of the present invention, as further described herein. In one preferred embodiment, endoscope 30 is a flexible fiber endoscope 30 as described herein.

In cases where a scope 30 provided is not capable of being inserted into a particular sinus cavity of interest, or to extend the view of endoscope or otherwise assist visualization through the endoscope, and/or to provide visualization for guiding guidewire 110 into the sinus cavity either prior to insertion of endoscope in the cavity or where endoscope 30 is incapable of being inserted into that particular cavity, an illumination guidewire 110 may be utilized to enhance visualization.

Figure 18:
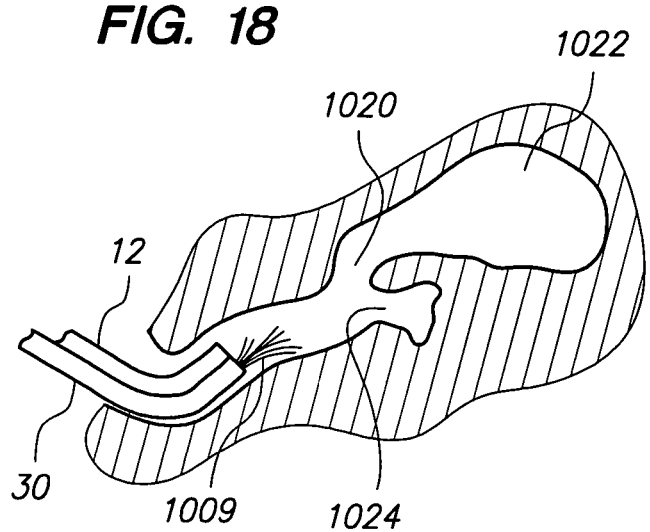
FIG. 18 illustrates use of an endoscope inserted through the guide device for visualization.

Further, depending upon the particular configuration of the sinus passageways to be traversed to gain access to a target ostium, the scope 30, due to physical limitations (e.g., outside diameter, degree of rigidity, etc.) may be unable to visualize as deep as the location of the ostium of interest. For example, FIG. 18 illustrates a situation where scope 30 has been inserted as far as possible without causing significant trauma to the patient. The range of adequately illuminated visibility in this case does not extend all the way to ostium 1020, as indicated schematically by the rays 1009 shown extending distally from scope 30. In this case, adequately illuminated visualization of guidewire 110 into ostium 1020 would not be possible via scope 30. Additionally, if sinus guide 12 is physically capable of being extended further distally to place the distal end thereof at the approach to ostium 1020, scope 30 would also not be capable of adequately visualizing this. Thus, prior to the provision of an illuminated guidewire 110 as described herein, fluoroscopic or other x-ray visualization of these procedures was required, in order to ensure that the devices approach (and extend through) the appropriate ostium 1020 and not another adjacent opening, such as opening 1024.

In order to overcome these and other problems, the guidewire devices 110 of the present invention include their own light emitting capability. By illuminating a distal end portion of guidewire 110, a process known as transillumination occurs as guidewire 110 traverses through the sinus passageways, passes through an ostium and enters a sinus cavity. Transillumination refers to the passing of light through the walls of a body part or organ. Thus, when guidewire 110 is located in a sinus, the light emitted from guidewire 110 passes through the facial structures and appears as a glowing region on the skin (e.g., face) of the patient. It is noted that the light emitted from scope 30, such as positioned in FIG. 18, for example, results in transillumination as well, but the resultant glow is much more diffuse and larger in area. As the light source in guidewire 110 gets closer to the surface of the structure that it is inserted into (e.g., the surface of the sinus), the transillumination effect becomes brighter and more focused (i.e., smaller in area). Additionally, the movements of the guidewire 110 can be tracked by following the movements of the transillumination spot produced on the skin of the patient. For example, the light emission portion of illumination guidewire can cause transillumination as guidewire 110 is being manipulated to gain access to an ostium and sinus. By tracking movements of a transillumination spot that moves as the illuminating portion of the guidewire 110 is moved during the manipulation, this can provide feedback to the user about steering an positioning and whether or not they are successful in entering through the ostium and into the sinus of interest. For example, transillumination may be visible on the bridge of the nose when gaining access to the frontal sinus. If the user positions the illuminating guidewire 110 medially, transillumination may show in the medial aspect. As the user looks for the frontal recess, he may then move the illuminating guidewire 110 laterally. Transillumination can then confirm that the distal end portion of the guidewire has indeed been moved laterally, as the user tracks the lateral movement of the illumination spot.

Figure 19:
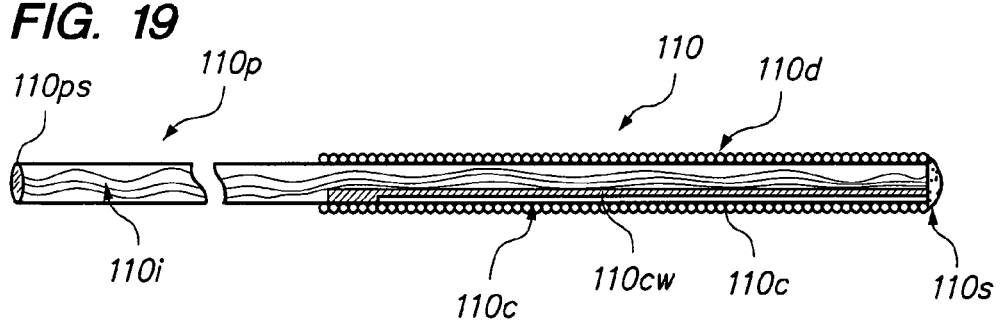
FIG. 19 shows an illuminating guidewire according to one embodiment of the present invention.

FIG. 19 shows an illuminating guidewire 110 according to one embodiment of the present invention. Device 110 includes a flexible distal end portion 110*d* that provides a similar degree of flexibility to a standard, non-illuminating type of guidewire. Distal end portion 110*d* may include a coil 110*c* as an exterior portion thereof, to help provide the desired flexibility to this portion. The proximal end portion 110*p* of device 110 extends the device to provide a sufficient length so that device 110 extends proximally out of the patient (and, when inserted through another device, such as a sinus guide 12, proximally out of the device into which guidewire 110 is inserted), at all times, including the deepest location into which the distal end of device 110 is placed. The proximal end portion 110*p* can have visible markings, preferably spaced at equal intervals, that can be observed by the user to confirm how far the guidewire 110 has been placed in the patient. Proximal end portion 110*p* also provides the necessary mechanical properties required to make the guidewire function properly. These mechanical properties include torquability, i.e., the ability to torque the proximal end portion 110*p* from a location outside of the patient and have that torque transmitted to the distal end portion 110*p*; pushability, i.e., sufficient rigidity, so that when an operator pushes on the proximal end portion 110*p* from a location outside of the patient, the pushing force transmits to the distal portion 110*d* to advance the distal portion 110*p* without buckling the device 110*p*; and tensile strength so that an operator can pull on the proximal end portion 110p from a location outside of the patient and withdraw device 110 from the patient without significant plastic deformation or any disintegration of the device.

Coil 110c may be formed from a stainless steel wire, for example. The diameter of the coil wire can be between about 0.004 and about 0.008 inches, typically about 0.006 inches. In one particular embodiment, coil 110c is made of stainless steel wire having a diameter of about 0.006 inches, coiled into a coil having an outside diameter of about 0.033 inches. Use of wire having a larger diameter provides added strength to the coil, but at the same time requires a larger outside diameter coil, which makes the overall device 110 more difficult to advance through small openings, but also allows more space in the inside diameter of the coil. Alternative materials from which coil 110c may be formed include, but are not limited to: ELGILOY®, CONICHROME® or other biocompatible cobalt-chromium-nickel alloy; nickel-titanium alloys, or other known biocompatible metal alloys having similar characteristics. Further alternatively, distal end portion may comprise a braided metallic construction of any of the aforementioned materials in lieu of a coil.

The external casing of the proximal portion 110p can be made from a polyimide sheath, a continuous coil (optionally embedded in polymer or having polymer laminated thereon), a hypotube (e.g., stainless steel hypotube), a laser-cut hypotube, a cable tube, or a tube made from PEBAX® (nylon resin) or other medical grade resin. In any of these cases the construction needs to meet the required torquability, pushability and tensile requirements of the device.

Figure 20:
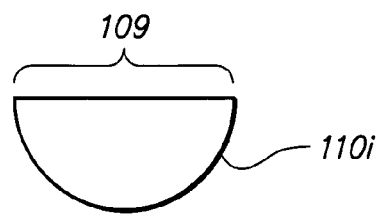
FIG. 20 illustrates an end view of a semi-cylindrical illumination fiber.

In the example shown, coil 110c is joined to proximal portion 110p by solder, epoxy or other adhesive or mechanical joint. One or more illumination channels 110i are provided in device 110 and extend the length thereof. Illumination channels 110i are configured to transport light from the proximal end of device 110 to and out of the distal end of device 110. In the example shown, two illumination channels are provided, each comprising a plastic illumination fiber. The plastic used to make the illumination fibers is compounded for light transmission properties according to techniques known and available in the art. As one example, ESKA™ (Mitsubishi Rayon), a high performance plastic optical fiber may be used, which has a concentric double-layer structure with high-purity polymethyl methacrylate (PMMA) core and a thin layer of specially selected transparent fluorine polymer cladding. In one example, illumination fibers each have an outside diameter of about 0.010". In one example, two acrylic light fibers each having an outside diameter of about 0.10" are used. The illumination fibers can have an outside diameter in the range of about 0.005 inches to about 0.010 inches. Alternatively, a single plastic illumination fiber 10i may be used that has an outside diameter of about 0.020". As another alternative, a single light fiber having an outside diameter of about 0.010" can be used. This provides additional internal space for other components, but halves the light output compared to embodiments using two 0.010" fibers. FIG. 20 illustrates another alternative, in which a single, semi-cylindrical light (illumination) fiber is used, wherein the diameter 109 is about 0.020". This half-round or semi-cylindrical fiber frees up additional internal space in the device, relative to use of two cylindrical fibers of 0.010" each, and provide about the same illumination output. However, these fibers are expensive and time consuming to manufacture. Other illumination fibers 110 having custom-shaped cross sections may be alternatively used, but again may be expensive and difficult to manufacture. Further alternatively, glass illumination fibers may be substituted which are much smaller in outside diameter, e.g., about 0.002". In this case, more illumination fibers may be provided in a bundle, e.g., about six to fifty glass fibers 110i may be provided.

The distal end of device 110 is sealed by a transparent (or translucent) seal 110s which may be in the form of epoxy or other transparent or translucent adhesive or sealing material, which may also function as a lens. For example, seal 110s may be formed of a translucent, ultra-violet curing adhesive to form a distal lens of the guidewire 110. Alternatively, other translucent or transparent and biocompatible adhesives or epoxies may be substituted. Seal 110s maintains the distal ends of illumination fibers 110i coincident with the distal end of device 110 and also provides an atraumatic tip of the device 110. Further, seal 110s prevents entrance of foreign materials into the device. The distal end can be designed to either focus or distribute the light as it emanates therefrom, to achieve maximum transillumination effects. In this regard, the distal end can include a lens, prism or diffracting element.

The proximal end of device 110 is also sealed by a transparent (or translucent) seal 110ps which may be in the form of epoxy or other transparent or translucent adhesive or sealing material. Seal 110ps maintains the proximal ends of illumination fibers 110i coincident with the proximal end of device 110. The proximal end of device 110 may be further prepared by grinding and polishing to improve the optical properties at the interface of the proximal end of device 110 with a light source. The illumination fibers 110i at locations intermediate of the proximal and distal ends need not be, and typically are not fixed, since no mapping of these fibers is required, as device 110 provides only illumination, not a visualization function like that provided by an endoscope. Further, by leaving illumination fibers free to move at locations between the proximal and distal ends, this increases the overall flexibility and bendability of device 110 relative to a similar arrangement, but where the illumination fibers 110i are internally fixed.

The outside diameter of device 110 may be in the range of about 0.025 inches to about 0.040 inches, typically about 0.030 to 0.038 inches, and in at least one embodiment, is about 0.035"±0.005". At least the distal portion 110p of device 110 is provided with a core support 110cw that is contained therein. In the example shown in FIG. 19, core support 110cw is a wire that is fixed to proximal section 110p such as by laser welding, epoxy or other adhesive or mechanical fixture. Core support 110cw may extend substantially the full length of device 110. In any case, core support 110cw is typically formed from stainless steel NITINOL (nickel-titanium alloy) or other biocompatible nickel-titanium alloys, cobalt-chromium alloys, or other metal alloys that are biocompatible and provide the necessary rigidity and torquability. Core support 110cw may be formed as a wire, as in the example shown in FIG. 19, or alternatively, may be braided from any of the same materials or combination of materials mentioned above. Core support 110cw, when formed as a wire can be ground to different diameters to provide varying amounts of rigidity and torquability. When formed as a braid, the braid can be formed to have varying amounts of rigidity and torquability along the length thereof. For example, core wire 110cw has a larger outside diameter at the proximal end portion than at the distal end portion so that it is more rigid and transfers more torque from the proximal portion of device 110, whereas at the distal end portion, core 110cw is relatively more flexible and twistable. For core supports 110cw that extend through proximal portion 110p, the portion of core support near the proximal end of device 110 may have an even larger outside diameter.

Figure 21A:
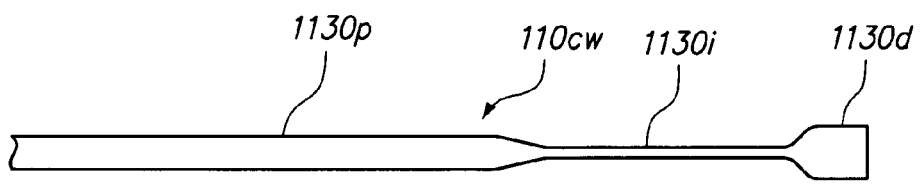
FIG. 21A shows a core support that may be used to support an illuminating guidewire.
Figure 21B:
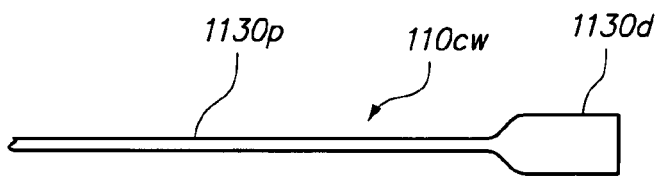
FIG. 21B shows a core support that may be used to support an illuminating guidewire.

In at least one embodiment, two core supports 110cw are provided in guidewire 110. FIGS. 21A-21B illustrate an embodiment of the first and second core supports, respectively. In FIG. 21A, core support 110cw may be formed from a nickel titanium alloy core wire having a diameter of about 0.008", although a similar configuration can be made starting with a core wire of different material and/or different diameter. A proximal portion 1130p of core support 110cw is maintained as the full wire profile having the diameter of 0.008". An intermediate section 1130i is ground down to a 0.006" diameter for greater flexibility in a distal end portion of the guidewire 110. The distal end portion 1130d is flattened, which facilitates soldering core support 110cw to coil 110c. The length of flattened section 1130d is maintained small, e.g., about 0.8 cm to prevent guidewire whipping. Alternatively, flattened section 1130d may be eliminated altogether with the reduced diameter round cross section 1130i extending to the distal end of core support 110cw. The length of the section 1130i (whether or not flattened section 1130d is employed) may be varied to customize the length of a flexible distal end portion of guidewire 110.

In FIG. 21B, core support 110cw that may be formed from a nickel titanium alloy core wire having a diameter of about 0.006", although a similar configuration can be made starting with a core wire of different material and/or different diameter. Proximal portion 1130p of core support 110cw is maintained as the full wire profile having the diameter of 0.006". A distal end portion 1130d is flattened, which facilitates soldering core support 110cw to coil 110c and provides flexibility at the tip of the guidewire 110 for atraumatic interaction with tissue. The length of flattened section 1130d can be about two centimeters, for example.

Alternative to the use of two core supports 110cw, a single core support may be used, as already noted above with regard to FIG. 19. Further alternatively, such a single core support 110cw can be made from an oval-shaped or elliptical-shaped (in cross-section) core wire if enough space is available, which may be made available by eliminating one of the illumination fibers 110i, for example. FIG. 22A shows an example of a core support 110cw formed from an oval wire and FIG. 22B illustrates a proximal end view of core support 110cw, showing the oval profile at the proximal end of core support 110cw. Proximal portion 1130p of core support 110cw is maintained as the full wire profile having the oval-shaped cross-section, wherein the height 1130h of the wire is about 0.015" and the width 1130w of the wire is about 0.010", see FIG. 22B. Intermediate section 1130i is ground down to a round cross-section having a diameter of about 0.010" for greater flexibility in a distal end portion of the guidewire 110. Distal end portion 1130d is flattened, and may have a length of about 0.8 cm to about 1.2 cm, for example, typically about 1 cm, which facilitates soldering core support 110cw to coil 110c. The length of flattened section 1130d is maintained small, e.g., about 0.8 cm to prevent guidewire whipping. Alternatively, flattened section 1130d may be eliminated altogether with the reduced diameter round cross section 1130i extending to the distal end of core support 110cw. The length of the section 1130i (whether or not flattened section 1130d is employed) may be varied to customize the length of a flexible distal end portion of guidewire 110. The dimensions of the oval or elliptical cross section may be varied depending upon the amount of space available inside coil 110c, accounting for all other components to be contained therein, as well as performance characteristics (e.g., flexibility, stiffness, torquability, etc) desired.

Coil 110c may be overlaminated, such as by melting nylon (or other polymer, such as PEBAX, GRILLAMID (nylon resin), or other medical grade resin) into open-pitched areas of the coil 110c to fill in these areas. The overlamination material increases the steerability of guidewire 110, increases torquability of guidewire 110 and provides an area that can be easily gripped by the user.

FIGS. 23A-31 are now referred to in describing manufacturing steps that may be carried out during the manufacture of certain embodiments of illuminating guidewire 110. In these embodiments, coil 110c extends over substantially the entire length of guidewire 110 and at least one of core supports 10cw extends into a proximal portion of guidewire 110. In FIG. 23A, a distal portion of coil 110c is stretched to break tension between adjacent coils and to form an open-pitch portion 110co of coil 110c. Next, two mandrels 1132 (which may be coated with a lubricious material such as polytetrafluoroethylene, or the like), having dimensions about the same as illumination fibers 110i that will later replace them, are inserted into coil 110c, as illustrated in the longitudinal sectional schematic of FIG. 23B. The core support 10cw having the smaller cross-sectional proximal portion dimension (e.g., core support 10cw formed from a 0.006" core wire, as described with regard to FIG. 21B above), referred to here as the "first core support" 10cw, is inserted into the coil 110c such that a distal end of distal portion 1130d is set back proximally from a distal end of coil 10c by a predetermined distance. In one example, this predetermined distance is about seven cm. In another example this predetermined distance is about nine cm. However, this predetermined distance may be varied depending upon the desired performance characteristics of the distal end portion of illuminating guidewire 110. By decreasing the predetermined distance, this increases the stiffness, or moves the stiff section more distal on the distal end portion of the guidewire 110. Increasing the predetermined distance moves the stiff section more proximal and leaves a greater flexible length at the distal end portion of the guidewire 110.

Figure 23C:
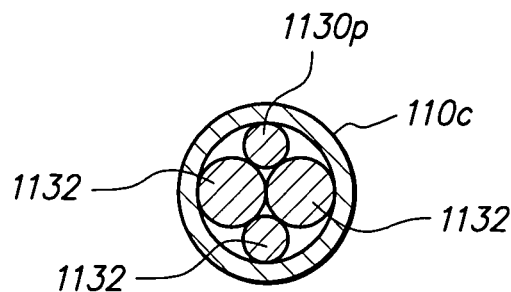
FIG. 23C shows a cross-sectional view taken along line 23C-23C of FIG. 23B.

A third mandrel 1132, which may be made the same as the above-described mandrels 1132, but which has dimensions to occupy a space that will later be occupied by the second core support 10cw, is inserted, which appears as the bottom mandrel 1132 shown in FIG. 23B. FIG. 23C shows a cross-sectional view of this arrangement, with the bottom mandrel 1132 being the mandrel that occupies the space that will be later filled by the second core support 10cw, and the other two mandrels 1132 occupying the spaces that will be later filled by illumination fibers 110i. The distal end 1130d of the core support 10cw may then be soldered to coil 110c.

In cases such as this, where coil 110c is stainless steel and core support is made of a nickel-titanium alloy, oxide on the nickel-titanium material, in regions to be soldered can be removed, prior to soldering, to improve solder joint strength. This removal can be accomplished using a highly acidic flux. For example, a phosphoric acid-based flux (about 65% to about 75%, by weight, phosphoric acid) was found to achieve satisfactory removal of the oxide. To further improve the solder joint strength, the regions on the nickel-titanium material that are to be soldered can be manually cleared of oxide, such as by removal using sandpaper or grinding. Further alternatively, or additionally, a chemical etch may be used.

One example of a solder used to form the solder joints is a tin/silver eutectic solder (96.5% Sn, 3.5% Ag, 0.5% Cu). This eutectic alloy works well as the solder in this case because strength is desired, and the eutectic alloy has no liquidus/solidus transition range, so the solder joint solidifies all at once, which greatly reduces the chances, making it almost impossible for the joint to be disrupted as it is solidifying.

Next, the mandrel 112 occupying the space for the second core support 10*cw* is removed and the second core support 10*cw* (e.g., core support 10*cw* formed from a 0.008" core wire, as described with regard to FIG. 21A above, referred to here as the "second core support" 10*cw*) is inserted into the coil 110*c* in the opening left by removal of the mandrel 1132. The first and second core supports 10*cw* are then soldered to coil 10*c* at multiple locations over the length of the core supports. In one particular example, soldering of the second core support 10*cw* includes a distal-most solder joint made about two to about five coils back from a distal end of coil 110*c*, a second solder joint is made about two cm distal of the location along coil 10*c* where the distal solder joint for the first core support 10*cw* was made, a third solder joint is made proximal of the distal solder joint of the first core support, but distal of the transition between the open-pitch coil section 110*co* and the remainder of the coil 110*c* (closed-pitch section), a fourth solder joint is made proximal of the open-pitch coil section 110*co*, and a fifth solder joint is made at the proximal end of coil 110*c*. The third, fourth and fifth solder joint locations join both of the core supports 10*cw* to the coil 10*c* for added strength and rigidity.

Figure 24A:
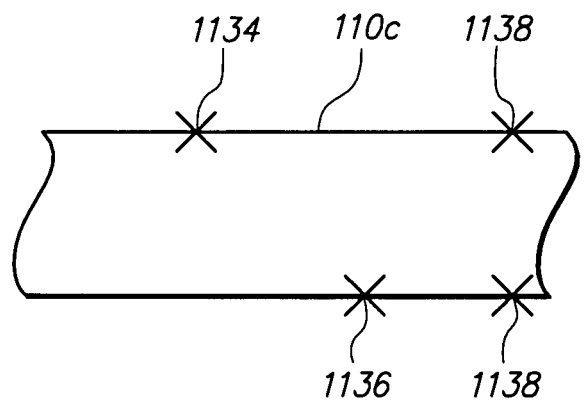
FIGS. 24A-24B illustrate the sliding ability of core supports relative to one another during bending of the coil.
Figure 24B:
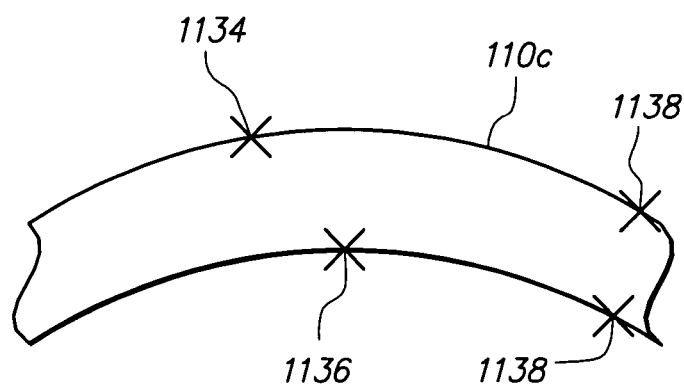

By making solder joint for the distal end of the first core support 10*cw* and the second solder joint of the second core support 10*cw* at locations on coil 10*c* that are at unequal locations along the longitudinal dimension of coil 110*c*, this allows the core supports 10*cw* to slide independently of each other during bending of the distal end portion of the illumination guidewire 110. For example, FIGS. 24A and 24B illustrate this independent sliding capability. As shown, the distal end solder joint 1136 of the smaller core support 10*cw* (core support 10*cw* formed from the 0.006' wire described in the example above) is illustrated at the bottom of coil 110*c*, the solder joint 1134 just distal of solder joint 1136 made between the second core support 10*cw* and coil 110*c* is shown at the top side of the illustration, and both core supports 10*cw* are soldered to coil 10*c* at a location distal of the transition between the open-pitch coil section 110*co* and the closed-pitch section, in this case, about sixteen cm from the distal end of coil 110*c*. FIG. 24A shows the relative positions of the solder joints when coil is in a straight configuration. FIG. 24B shows coil 110*c* in a bent configuration, and illustrates the ability of the core supports 10*cw* to slide independently of one another, as it can be observed that the solder joints 1134 and 1136 have moved closer together, as compared to the space between these joints shown in FIG. 24A when coil 110*c* is straight. Thus, when bending toward the first core support 10*cw*, the first core support 10*cw* is allowed to slide distally I relation to the second core support 10*cw* at the bend, because the cores are located together (same longitudinal fix point) at solder joints 1138, and the first core support 10*cw* does not extend all the way to the distal end of the coil 110*c*. If the solder joints 1134 and 1136 of the two core supports 110*cw* were soldered at the same longitudinal location, this would make the arrangement much stiffer and less flexible in this region. This would also result in greater amounts of "whip" upon torquing the device.

By soldering the core supports 10*cw* at locations 1134 and 1136 as shown in FIGS. 24A-24B and described above, the coils of coil 110*c* are prevented from substantial separation even when coil 110*c* is bent. This greatly increases the stiffness of guidewire 110/coil 110*c* in a segment between the solder joints 1134 and 1138, but still allows a distal section (distal of joint 1134 to the distal solder joint of the second core support 110*cw*) to remain floppy. Alternatively, to further increase the stiffness of the region between joints 1134 and 1138, the coils between joints 1134 and 1138 or between 1136 and 1138, or between 1134 and 1136 can be placed under compression during the soldering of the joints.

Further alternative soldering arrangements include, but are not limited to: soldering both core supports 10*cw* at the distal end of coil 110*c*. This increases the distal stiffness of the coil 110*c*/guidewire 110 and thus also reduced distal flexibility. This may also greatly increase whipping of the distal end when torquing the illuminating guidewire 110.

Further alternatively, the solder locations (locations longitudinally along the coil 110*c*) can be varied. For example, by moving joints 1134 and 1136 distally with respect to coil 110*c*, but keeping the same separation distance between coils 1134 and 1136, this moves the stiff section between the joints 1134 and 1136 closer to the distal end of guidewire 110, reducing the flexible section at the distal end portion of guidewire 110. Conversely, moving joints 1134 and 1136 proximally with respect to coil 110*c*, but keeping the same separation distance between coils 1134 and 1136, moves the stiff section between the joints 1134 and 1136 further from the distal end of guidewire 110, increasing the length of the flexible section at the distal end portion of guidewire 110 and reducing the length of the stiff section.

Figure 25:
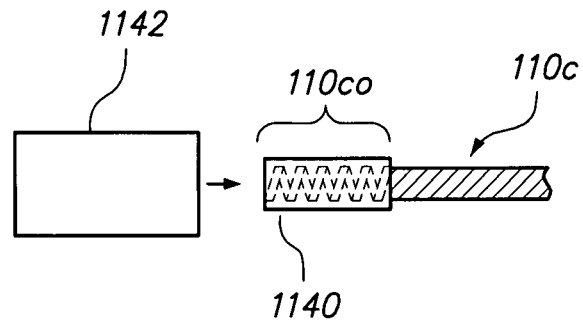
FIG. 25 illustrates a step of melting a polymer tube into the open-pitched portion of the coil.

Once core supports 10*cw* have been soldered to coil 110*c* according to any of the techniques described above, the open-pitch coil section 110*co* of coil 110*c* can next be laminated. A nylon (or other meltable polymer) tube 1140 is slid over the open-pitched coil section 110*co*, as illustrated in FIG. 25, and then a FEP (fluorinated ethylene propylene) heat shrink tube 1142 is slid over the meltable polymer tube 1140. Tubing 1142 is heated until it shrinks down around the coils of the open coil section 110*co* and melts the polymer tubing into the spaces between the coils. After cooling, the shrink tubing 1142 is removed.

Figure 26A:
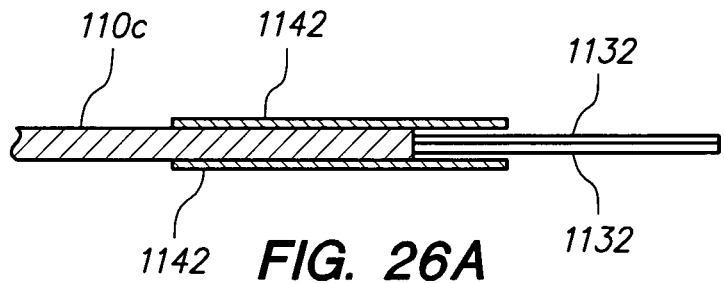
FIGS. 26A-26B illustrate steps for mounting a connector to a proximal end of the illuminating guidewire.
Figure 26B:
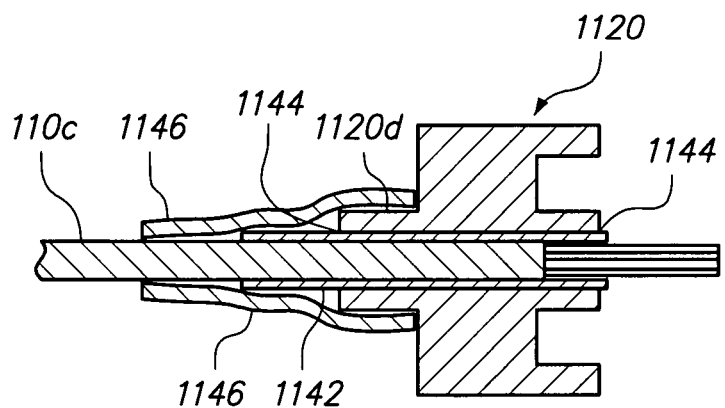

FIGS. 26A-26B illustrate steps that may be performed to install connector 1120 to the proximal end of guidewire 110. These steps may be performed while at least the mandrels 1132 that are to be replaced by illumination fibers 110*i* are still inserted through coil 110*c*. A heat shrink tube (e.g., FEP heat shrink material) 1140 is shrunk down around a proximal end portion of coil 110*c* as illustrated in FIGS. 26A which shows a longitudinal sectional view of the heat shrink tubing, and a plan view of coil 110*c* and mandrels 1132. The tubing 1142 extends proximally beyond the proximal end of coil 110*c* by a predetermined distance, e.g. about two mm. Mandrels 112 act to keep the proximal end of tubing 1142 from shrinking closed during heating.

Next, connector 1120 is slid over tubing 1142 so as to substantially align the proximal end of connector 1120 with the proximal end of tubing 1142, as illustrated. Tubing 1142 help to center coil 110*c* within the connector 1120 and also functions as a strain relief. Adhesive 1144 can be applied to adhere connector 1120 to tubing 1142. Another shrink tubing 1146 (e.g., polyeolefin shrink tubing) is slid over the distal end portion 1120*d* of connector 1120 and shrunk down around the distal end portion 1120*d*, tubing 1142 and coil 110*c*, thereby securing connector 1120 to coil 110*c* and also functioning as a strain relief. Connector 1120 may include a rotatable (relative to coil 110) or non-rotatable female luer connector, or rotatable (relative to coil 110) or non-rotatable male luer connector, for example.

At this time, the remaining mandrels 1132 can be removed from coil 110*c* in preparation for installation of the light (illumination) fibers 110*i*. After removal of the mandrels 1132, two light fibers 110*i* are installed in their place and extended distally beyond the distal end of coil 110*c*. The illumination fibers 110*i* are then cut to extend a predetermined distance distally of the distal end of coil 110*c*. In one example, this predetermined distance is about 0.5 mm, although this predetermined distance may vary. An adhesive lens 110s is the formed by applying ultra-violet curable adhesive (or other transparent or translucent adhesive) over the portions of illumination fibers extending distally from the distal end of coil 110c to completely encapsulate these fiber portions, as shown in FIG. 27. Note that, for simplicity of illustration, core supports have not been shown in the illustration of FIG. 27, however, these would, of course, also be contained within the coil 110c. Adhesive lens 110s will typically be formed to have a hemispherical distal surface, as shown, although the curvature and shape of this distal surface can be varied, depending upon the characteristics of light patterns desired to be emitted therefrom. Note that adhesive is also applied so as to spread over at least one coil of the coil 110c and at least one space between coils. Adhesive lens 110s is then cured to complete the formation of the adhesive lens 110s.

The same or a similar adhesive can be used to apply to the proximal end portion of coil 110c and portions of the illumination fibers 110i in the proximal end 110ps vicinity, as illustrated in FIG. 28. Adhesive can be applied in amounts enough attach/encapsulate up to about one-half of the proximally exposed portions of illuminating fibers 110i that extend proximally from the proximal end of coil 110c. The illumination fibers are then cut substantially flush with the proximal end of connector 1120, as shown in FIG. 28. Optionally, after curing the adhesive, the portion of shrink tubing 1142 extending proximally from the proximal end of coil 110c, may next be shrunk down around the proximally extending portions of illumination fibers 110i, for example, to an outside diameter of about 0.022", to lower the light input into device 110 and allow light input substantially only through the illumination fibers 110i. Alternatively, and also optionally, a grommet 1148 (shown in phantom) can be inserted over illumination fibers and inside of shrink tubing 1142, with or without subsequent further shrinking of the shrink tubing, to accomplish the same function.

Further optionally, the proximally extending portions of light fibers 110i may be completely encapsulated in adhesive or epoxy, in the same manner as described above with regard to adhesive lens 110s. This proximal adhesive lens can be configured to function as a lens to direct light into light fibers 110i, for example, but the adhesive or epoxy used in this instance must be able to withstand heat generated by the light cable when connected to connector 1120 during use.

Optionally, illuminating guidewire may be manufacture to have a preset curve or bend in a distal end portion thereof. For example, the larger core support 110cw in the process described above can be set with a curve or bend to form a resulting bend in the distal end portion of guidewire 110 once constructed. FIG. 29A is a partial view of the core support 110cw described with regard to FIG. 21A, while still in a straight configuration. FIG. 29B illustrates one method of forming a preset curve in core support 110cw in which the flatted distal end section 11 30d is bent at an angle of about ninety degrees by bending it around a mandrel 1150. In one example, mandrel 50 had a outside diameter of about 0.05". By cold working (i.e., plastically deforming) the distal portion about the mandrel 1150 and setting it a about ninety degrees, a curve of about twenty degrees will result in the finished illuminating guidewire device 110 employing this core support in a manner as described above. Alternatively, the nickel-titanium distal end portion 1130d can be bent in the same manner as shown in FIG. 29B, but rather than cold working, the distal end portion can be heated to it annealing temperature and then bent around the mandrel 1150 and quenched.

Figure 30:
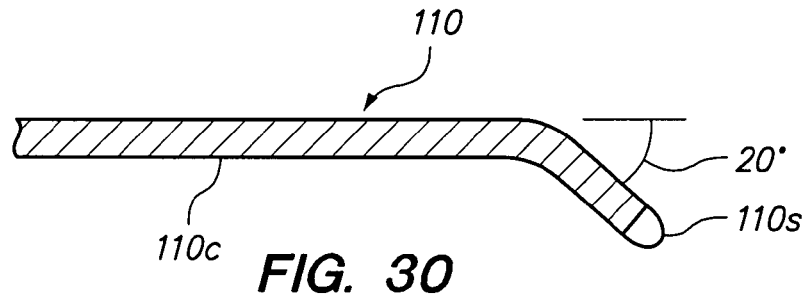
FIG. 30 illustrates a resulting bend in an illumination guidewire employing a core support having a preset bend.

FIG. 30 illustrates a distal portion of an illuminating guidewire 110 manufactured with a core support have a preset bend from either of the techniques described above with regard to FIGS. 29A-29B. The bend in the distal end portion makes it more steerable, as discussed above and in application Ser. No. 11/647,530.

Figure 31:
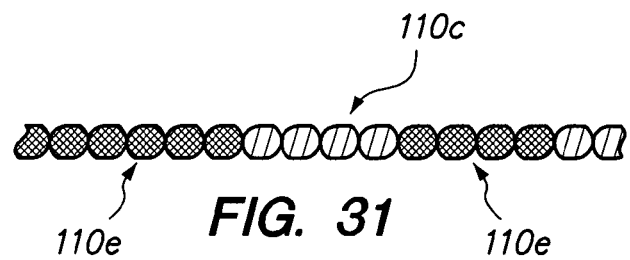
FIG. 31 illustrates etching the coil.

FIG. 31 is a partial view of coil 110c illustrating two portions of coil 110c that have been etched 110e. Etching may be performed over all, or one or more select portions of coil 110c to lower reflectance of the coil where etched, such as when viewed by endoscopy, for example, and/or to act as a marker band to identify a particular location along the coil 110c.

Illumination guidewire 110 may be externally coated with a silicone coating to reduce friction (add lubricity) between guidewire 110 and the tissues, guides and/or other instruments that it is slid against during use. Other lubricious coatings may be substituted, including, but not limited to: polytetrafluoroethylene, parylene, hydrophilic coatings, any of which may be spray coated or dipped, for example, or may be pre-coated on the wire from which the coil is made by the wire manufacturer, or may be pre-coated on the coil 10c if the coil is manufactured by an outside source.

The illumination fibers 110i, as noted previously, can be free to move about radially within the device 110. Further, there is no need to center the illumination fibers 110i with respect to device 110 even at the distal and proximal ends of the device. The plastic or glass illumination fibers 110i are typically used to transmit light from a light source such as one provided in an operating room for use by endoscopes, e.g., xenon light source, halogen light source, metal halide light source, etc. Alternatively, device 110 may be configured to transmit light from other light sources, such as a laser light source, wherein laser fibers would be substituted for the illumination fibers described above, and extend through device 110 in a fiber optic bundle. The fiber optic bundle, like the illumination fibers 110i, contributes to stiffness (in both bending and torquing motions) of device 110, thereby enhancing trackability, steering and other torquing. Alternatively, device 110 may employ one or more light emitting diodes used to emit light, as described in more detail in application Ser. No. 11/647,530.

Figure 32:
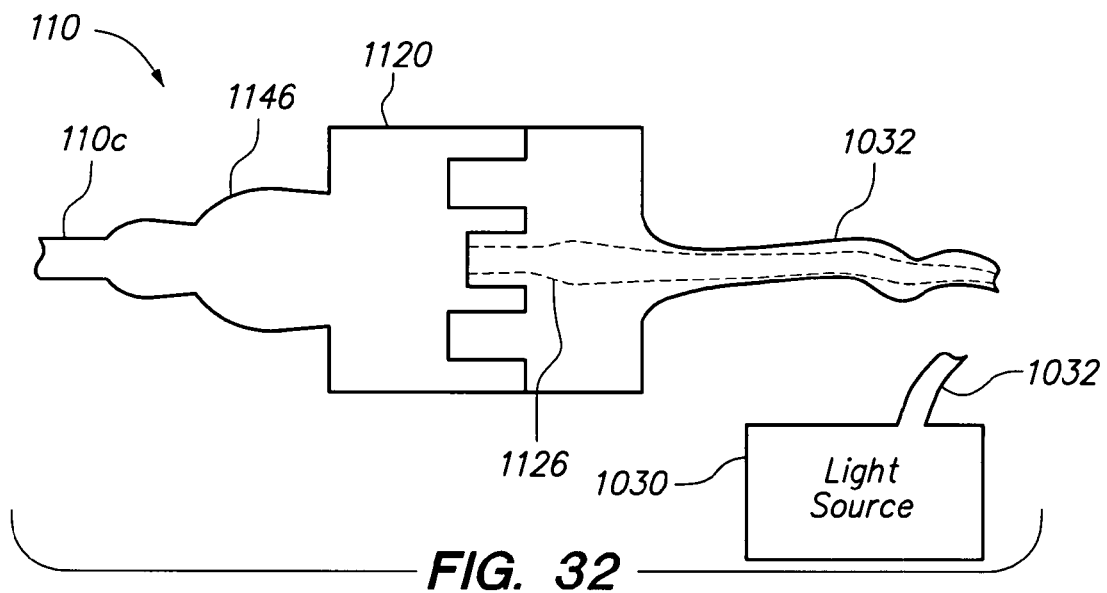
FIG. 32 illustrates connection of a light cable to an illuminating guidewire according to one embodiment.

A light cable 1032 optically connects connector 1120 with light source 1030 to deliver light from the light source 1030 through connector 1120 and illumination fibers 110i. The light cable 1032 must transmit enough light to allow the illuminating guidewire 110 to transilluminate the sinuses, but at the same time, not transmit so much light that the light fibers become damaged. Research has shown that very bright light sources 1030 (e.g., 300 Watt Xenon, new bulb) can damage the light fibers 110i with a light cable surrounding a glass illumination fiber bundle wherein the light cable has a diameter of greater than about 2 mm. One way to concentrate the light coming from light cable 1032 down to a size more nearly matching that needed for the illumination fibers 110i is to provide a taper (which may be made of glass, for example) 1126 as illustrated in phantom in FIG. 32. For example, taper 1126 may taper the diameter of the incoming light from about 2 mm down to about 1 mm. While the taper 1032 can concentrate or focus the light down, as noted, there are light losses that result in heat generation at the location of the taper 1126.

Alternatively, a light cable 1032, in this embodiment, has a connector 1320 at the distal end of light cable 1032 which is provided with a male luer 1322, for connection to the connector 1020 of illumination guidewire 110. The provision of a male luer is non-standard, as most operating room light cables are provided connectors specific to the manufacturer of the light cable, which are often proprietary to that manufacturer and which do not include a luer connector.

Accordingly, when the connector 1020 of illuminating guidewire 110 is configured to mate with this male luer 1322, this prevents a standard operating room light cable from accidentally being connected to the guidewire 110. The light fiber bundle in light cable 1032 is sized to provide sufficient illumination through illuminating guidewire 110 to transilluminated the sinuses, but an insufficient amount of light to damage the illumination fibers 110*i*. Also, a taper 1026 is not required since the light cable 1032 is sized to substantially match the illumination fibers 110*i*, and therefore the heat generation problem caused by tapering does not arise with this embodiment. In one example, the light fiber bundle 1324 has a diameter of about 1 mm.

Figure 33:
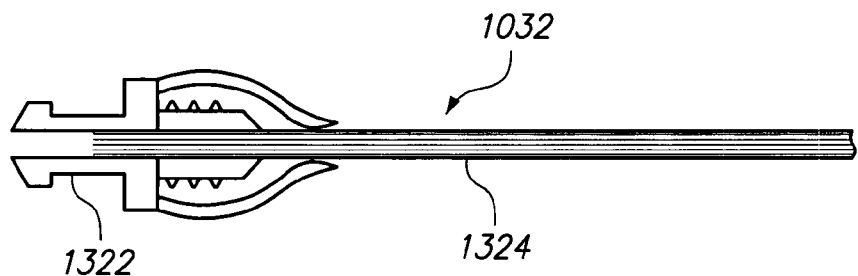
FIG. 33 illustrates a light cable having another connector embodiment.
Figure 34:
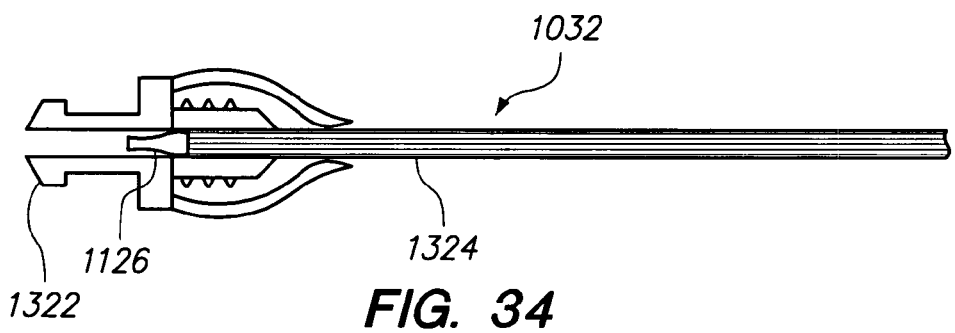
FIG. 34 illustrates a light cable having another connector embodiment.

Alternatively, the embodiment shown in FIG. 33 may also be provided with a taper 1126 to further funnel the light from light bundle 1324 down to a smaller diameter, as illustrated in FIG. 34.

Figure 35:
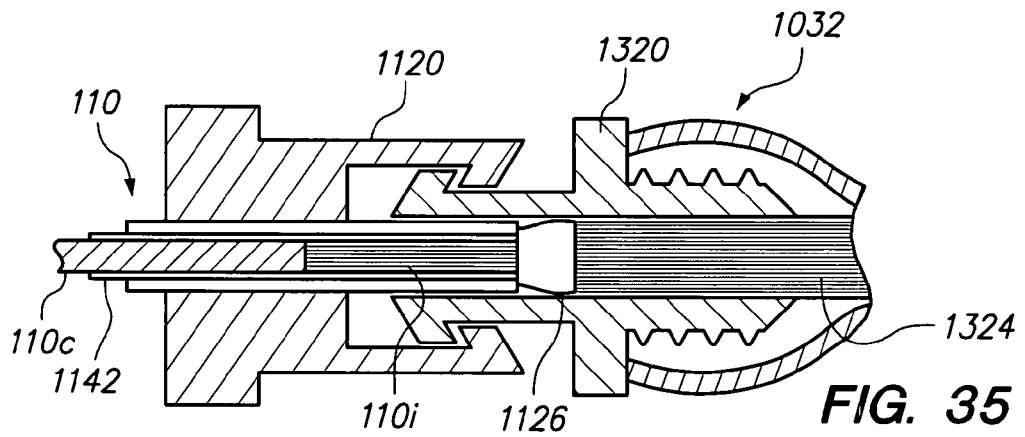
FIG. 35 illustrates connection of a light cable to an illuminating guidewire according to another embodiment.

FIG. 35 shows connector 1320 of light cable 1302 provided with a female luer mated with a male luer of connector 1020 of the illuminating guidewire 110. This arrangement allows the proximal ends of illumination fibers 110*i* to be placed flush in abutment with the light bundle 1324 or taper 1126 (as shown) when connector 120 is screwed or snapped onto connector 1320.

Any of the devices 110 described herein may optionally include one or more radiopaque markers and/or electromagnetic coils on the tip of the device 110 and/or elsewhere along the device for enhancing visibility by fluoroscopy systems, image guided surgery (IGS) systems, or other visualization systems.

Figure 36:
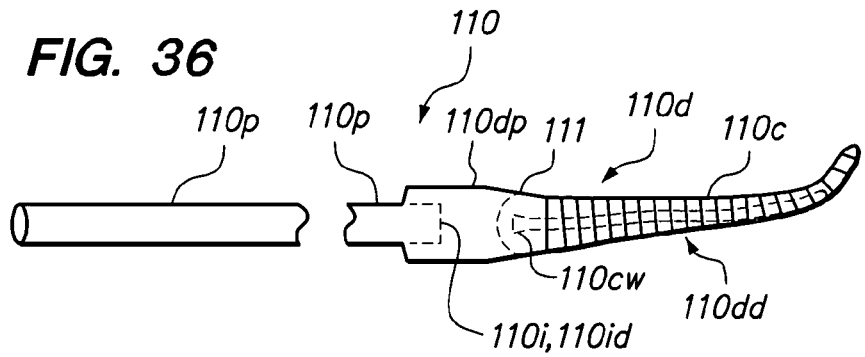
FIG. 36 shows an illuminating guidewire according to another embodiment of the present invention.

FIG. 36 shows an alternative design of device 110 in which light is emitted proximally of the distal end of the device. This configuration may employ any of the various light transmission means described above (e.g., illumination fibers, laser fibers, LED). The proximal portion 110*p* may be constructed in any of the manners described above with regard to other embodiments of device 110. The distal portion 110*d* includes a transparent proximal end portion 110*dp* that mounts over the distal end of proximal end portion 110*p* of the device 110. The transparent portion 110*dp* permits the illumination emitted from illumination member 110*i* or 110*id* to pass out of the device 110 at the location of transparent portion 110*dp*. The illumination member(s) 110*i* or 110*id* thus terminate at the proximal end portion 110*dp* of the distal end portion of device 110. Distally of this transparent portion 110*dp*, the distal portion 110*dd* of distal end portion 110*d* of device 110 extends as a floppy guidewire leader or tip. This floppy guidewire leader or tip 110*dd* may include a coiled section 110*c* and may optionally include a core support 110*cw*. The light emitted from illumination fibers will disperse naturally through the transparent portion 110*dp*. Optionally, a deflector 111, such as a convex mirror (e.g., parabolic or other convex) shape or other reflective surface may be provided distally of illumination fibers/light emitting portion 110*i*, 110*id* of device 110 to deflect light rays out of the transparent portion. Additionally, or further alternatively, illumination fibers 110*i* may be angled at the distal end portions thereof to direct the emitted light out through the transparent portion.

This configuration may be beneficial in further protecting the illumination emitter(s) 110*i* from foreign materials inside the body, as well as from trauma that may be induced by bumping the illumination emitter up against structures within the body. Further, a floppy guidewire leader 110*dd* of this type may provide more flexibility and maneuverability than a device in which the illumination emitter is located on the distal tip of the device.

Figure 37:
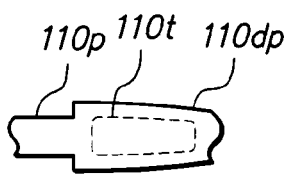
FIG. 37 illustrates an alternative transparent portion that may be included in a device shown in FIG. 36.
Figure 38:
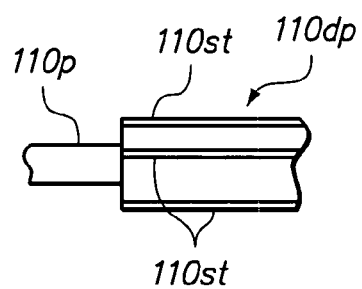
FIG. 38 illustrates another alternative transparent portion that may be included in a device shown in FIG. 36.

Transparent portion 110*dp* may be provided as a clear plastic or glass integral tube, or may have openings or windows 110*t* provided therein (see the partial view of FIG. 37). Further alternatively, transparent portion may be formed by a plurality of struts 110*st* circumferentially arranged to interconnect the distal floppy tip 110*dd* with the proximal end portion 110*p* of device 110 as shown in the partial illustration of FIG. 38. Alternatively members 110*st* may be intersecting in a criss-crossing cage like configuration or other cage configuration. In any of these alternative configurations, members 110*st* may be transparent, but need not be and could be formed of non-transparent materials, such as metals or opaque plastics, for example.

Figure 39A:
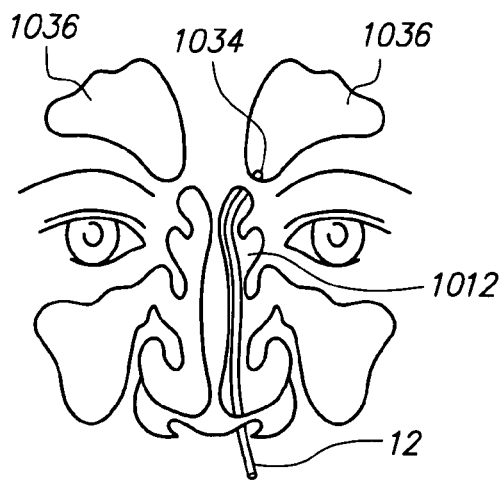
FIGS. 39A-39C are illustrations of partial coronal sectional views through a human head showing various steps of a method for inserting an illuminating guidewire into an ostium that opens to a frontal sinus.
Figure 39B:
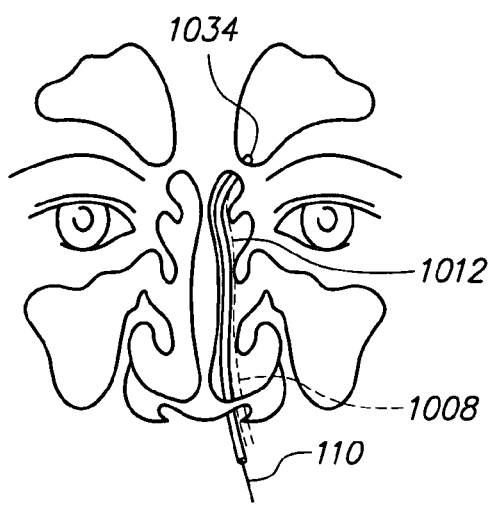
Figure 39C:
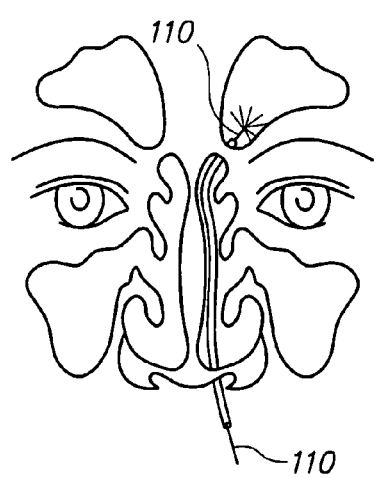

Turning now to FIGS. 39A-39C, illustrations of partial coronal sectional views through a human head showing various steps of a method for inserting an illuminating guidewire 110 into an ostium that opens to a frontal sinus are shown. The methods described here, and all other methods disclosed herein may also comprise a step of cleaning or lavaging anatomy within the nose, paranasal sinus, nasopharynx or nearby structures including but not limited to irrigating and suctioning. The step of cleaning the target anatomy can be performed before and/or after a diagnostic or therapeutic procedure. The methods of the present invention may also include one or more preparatory steps for preparing the nose, paranasal sinus, nasopharynx or nearby structures for the procedure, such as spraying or lavaging with a vasoconstricting agent (e.g., 0.025-0.5% phenylephyrine or Oxymetazoline hydrochloride (Neosynephrine or Afrin) to cause shrinkage of the nasal tissues, an antibacterial agent (e.g., provodine iodine (Betadine), etc. to cleanse the tissues, etc.

In FIG. 39A, a first introducing device in the form of a sinus guide 12 is introduced through a nostril and through a nasal cavity 1012 to a location close to an ostium 1034 of a frontal sinus 1036. Sinus guide 12 may be as described previously herein, or as described in the applications incorporated herein by reference. The advancement of sinus guide 12 can be visualized with a scope inserted into the nasal cavity 1012 (e.g., through channel 28, not shown in FIG. 39A) and advanced as close to the ostium 1034 as possible without causing significant trauma to the tissues therein.

Once the surgeon is satisfied that the distal end of the sinus guide 12 is positioned close enough to the appropriate ostium 1034, illuminating guidewire 110, connected to a light source as described by any of the techniques mentioned above, is inserted through sinus guide 12 and advanced therethrough, see FIG. 39B. There may be some transillumination from the light emitted from the scope which can be used to confirm that the sinus guide 12 is positioned in the correct general area, which confirmation can be made even before the distal tip of guidewire 110 exits the distal end of sinus guide 12. However, much more specific transillumination effects are produced when the tip of guidewire 110 exits the distal end of guide 12 and especially when the light emitting portion of guidewire 110 touches or approximates an intended target surface, such as an inner wall of a sinus, for example. As the guidewire 110 is advanced, transillumination on the face of the patient can be observed as a glowing spot that moves as the distal end portion of device 110 moves, thereby making it possible to visibly track the location of the light emitting portion of device 110 without the need to use radiographic imaging, such as by fluoroscopy, for example.

While there may be some diffuse transillumination on the forehead of the patient overlying the frontal sinus 1036 as the light emitting portion of device 110 approaches the ostium 1034, the glow on the forehead becomes brighter and smaller in dimension (more focused) as the light emitting portion passes through the ostium 1034 and enters the frontal sinus 1036, FIG. 39C. As device 110 is further advanced, the glowing spot becomes most defined and brightest as the light emitting portion approaches and contacts a wall of the frontal sinus 1036. Further, as noted, the movement of the transilluminated spot can be visibly followed to confirm that the guidewire 110 is indeed moving within the location of the frontal sinus, as can be confirmed by the surgeon's knowledge of the particular anatomy of the patient being treated. In this regard, a CAT scan or other image of the sinus anatomy can be performed prior to this procedure and studied by the surgeon, to apprise the surgeon of any distinctive or unusual patterns in the individual patient's sinus anatomy which might be useful in tracking and confirmation of where the guidewire is located, as indicated by the transillumination.

Figure 40:
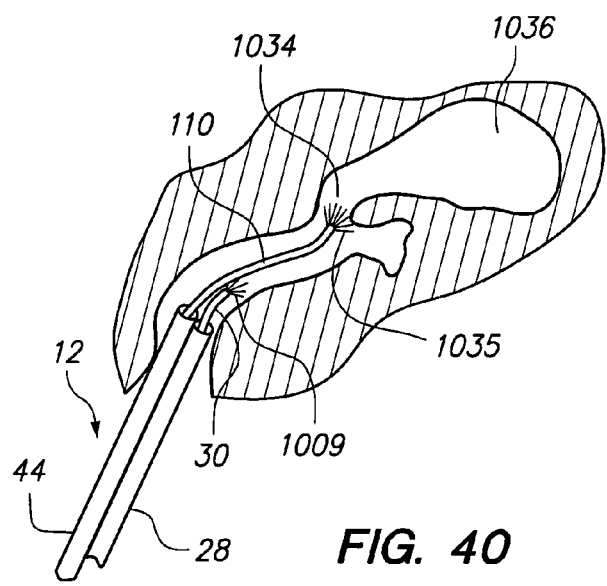
FIG. 40 illustrates a situation where a scope has been inserted as far as possible without causing significant trauma to the patient.

Illuminating guidewire device 110 can also be used to facilitate visualization and placement of the sinus guide 12 in the procedure described above with regard to FIGS. 39A-39C, or in another procedure in which a sinus guide, sinus guide or guide tube is placed in the sinus pathways. FIG. 40 illustrates a situation where scope 30 has been inserted as far as possible without causing significant trauma to the patient. The range of visibility in this case does not extend all the way to ostium 1034, as indicated schematically by the rays 1009 shown extending distally from scope 30. By inserting illuminating guidewire 110 through sinus guide 12 (tube 44) as shown in FIG. 30, additional illumination can be provided distally of the illuminating range of scope 30. This additional illumination can be received by scope 30 to enable visualization up to the illumination portion of device 110 and potentially even extending to illumination range of device 110, as long as there is a straight pathway of the field of view. Thus, placement of the guidewire 110 can be visualized up to and into the desired ostium 1034 via scope 30 in this case. Alternatively, this can be carried out without the sinus guide 12, wherein the guidewire 110 is inserted and the scope 30 can be used to visualize placement of guidewire 110 into the target ostium with the assistance of the light emitted by the scope 30 in addition to the light emitted by guidewire 110.

In any of these procedures where a scope 30 is used for visualization and an illuminating guidewire 110 is inserted, some transillumination of the target sinus may occur from the light emitted by the scope 30 alone. However, this transillumination will be diffuse and show a rather dim, large area of transillumination on the patient's skin. When the illumination guidewire 110 is inserted and advanced, as noted earlier, a smaller, brighter transillumination spot will be visible when the illuminating portion of the guidewire has entered the sinus. Additionally, even before entering the sinus, the light emitted from the guidewire 110 will produce a moving transillumination spot as guidewire 110 is advanced, which also helps distinguish the location of the distal portion of the guidewire 110, relative to any diffuse transillumination produced by the scope light.

If the guidewire 110 is advanced into an ostium other than the target ostium (e.g., ostium 1035 shown in FIG. 40), this may be possible to be viewed by scope 30, depending upon the line of sight. However, even if it is not, the transillumination resulting from entrance into a different sinus than the target sinus will be evident by the different location on the patient's face. Also, in the example shown, guidewire 110 would not be able to be advanced very far through ostium 135 before it was diverted and curled by the relatively small sinus space that ostium 135 leads into. Thus, by tracking the movement of the illumination spot produced by guidewire 110, the surgeon could confirm that guidewire 110 was misplaced as the guidewire would be diverted by a much smaller space then that characterized by the target frontal sinus 1036.

Thus, by using an illuminating guidewire device 110 in the methods as described above, the use of fluoroscopy or other X-ray visualization can be reduced as it is not required to confirm proper placement of the guidewire in some cases.

Guide Systems with Removable Endoscope/Guidewire Sheaths

Figure 41:
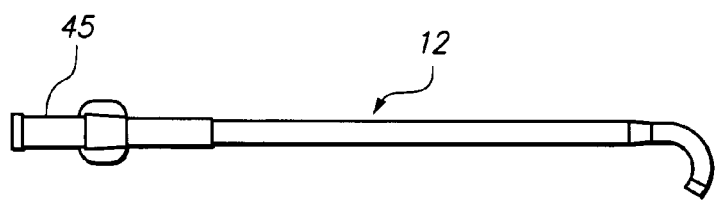
FIGS. 41-43 show additional embodiments of transnasally insertable guide systems useable to position an endoscope.
Figure 42:
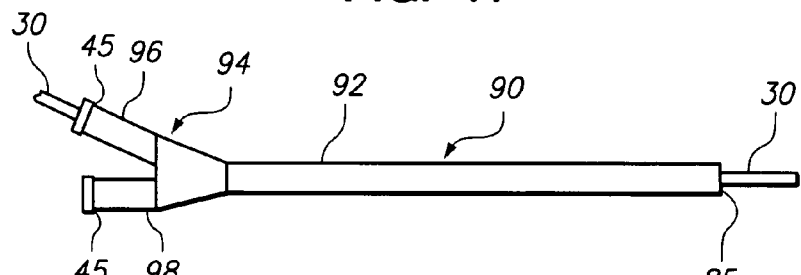
Figure 43:
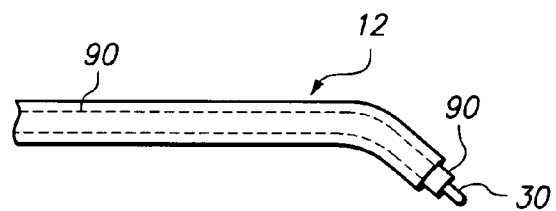

FIGS. 41-43 show additional embodiments of transnasally insertable guide systems useable to position an endoscope 30 at a desired location within the ear, nose, throat or cranium of a human or animal subject, to view anatomy for diagnostic purposes or for confirmation that a procedure has been successfully accomplished. In FIG. 41, guide device 12 includes a single tube 28 having a lumen sized to receive endoscope 30. Guide 12 may be preshaped to be straight or curved, or may be configured to be deflectable or steerable.

FIGS. 42-43 illustrate a guide system comprising a straight or curved transnasal sinus guide 12 and a sheath 90 that is insertable through the sinus guide 12. The sheath 90 has a single lumen sized and configured to receive endoscope 30 therethrough. Thus, endoscope 30 may be inserted through sheath 90 to extend distally of the distal end of guide 12, as illustrated in the partial view of FIG. 43, to view anatomy or visually verify the results of a procedure, for example. Examples of transnasal sinus guides 12 useable in this system include those described in U.S. patent application Ser. No. 11/193,020, published as U.S. Pub. No. 2006/0063973 on Mar. 23, 2006 and herein, as well as those currently available commercially as Relieva™ Sinus Guide Catheters from Acclarent, Inc., Menlo Park, Calif.

Sheath 90, illustrated in FIG. 42, an elongate flexible shaft 92 through which the endoscope lumen 85 extends. A proximal hub 94 may be provided with having two arms 96, 98, and is mounted on the proximal end of the flexible shaft 92. Arm 96 leads into the endoscope lumen 85 and arm 98 also leads to the endoscope lumen 85 and can be used, for example to attach a suction or irrigation source thereto. Alternatively, hub 94 may be provide with only a single arm 96.

It is to be appreciated that the invention has been described hereabove with reference to certain examples or embodiments of the invention but that various additions, deletions, alterations and modifications may be made to these examples and embodiments and or equivalents may be substituted without departing from the intended spirit and scope of the invention. For example, any element or attribute of one embodiment or example may be incorporated into or used with another embodiment or example, unless to do so would render the embodiment or example unsuitable for its intended use. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for locating a sinus ostium, said method comprising the steps of:
   (a) inserting a sinus guide and an endoscope through a nostril of a patient;
   (b) advancing the sinus guide toward a location of the sinus ostium under the guidance of the endoscope;
   (c) inserting an illuminating guidewire through the sinus guide and into the nostril and advancing a distal end portion of the illuminating guidewire distally of a distal end of the endoscope and distally of a distal end of the sinus guide, wherein the distal end of the illuminating guidewire includes a light emitting feature;

(d) viewing, through the endoscope, the advancement of the distal end portion of the illuminating guidewire to facilitate guidance of the advancement of the illuminating guidewire along a desired path;

(e) identifying a location of the sinus ostium by observing a transillumination region, wherein the transillumination region is provided by illumination from the light emitting feature of the guidewire;

(f) advancing a working device through the sinus guide to position the working device through a distal end of the sinus guide and into the sinus ostium after identifying the location of the sinus ostium by observing the transillumination region; and (h) actuating the working device to thereby perform a diagnostic or therapeutic function in one or both of the sinus ostium or an adjacent sinus cavity.

2. The method of claim 1, further comprising directing the distal end portion of the illuminating guidewire, under guidance facilitated by visualization of the distal end portion via the endoscope, into the sinus ostium.

3. The method of claim 2, wherein visualization through the endoscope is enhanced by light emitted by the illuminating guidewire.

4. The method of claim 2, further comprising confirming that the distal end portion of the illuminating guidewire has been inserted into a desired sinus by observing transillumination effects produced by the illumination from the distal end portion of the illuminating guidewire having been inserted through the sinus ostium and into the sinus.

5. A method for locating a sinus ostium, said method comprising the steps of:

(a) inserting a guide catheter and an endoscope through a nostril of a patient;

(b) advancing the guide catheter using the endoscope to guide the guide catheter toward a location of the sinus ostium;

(c) inserting an illuminating guidewire through the guide catheter and into the nostril and advancing a distal end portion of the illuminating guidewire distally of a distal end of the endoscope, wherein the illuminating properties of the guidewire are provided by an illuminating tip on the distal end of the illuminating guidewire;

(d) advancing the illuminating guide wire relative to the guide catheter such that at least a portion of the illuminating guidewire extends out of the distal end of the guide catheter and into the sinus ostium;

(e) viewing, through the endoscope, the advancement of the distal end portion of the illuminating guidewire to facilitate guidance of the advancement of the illuminating guidewire into the sinus ostium;

(f) identifying a location of the sinus ostium by observing a transillumination region created by the illuminating tip of the illuminating guidewire; and (g) inserting a working device through the guide catheter to position the working device inside the sinus ostium to perform a therapeutic procedure after identifying the location of the sinus ostium by observing the transillumination region.

\* \* \* \* \*